United States Patent
Franz et al.

(10) Patent No.: US 10,233,159 B2
(45) Date of Patent: Mar. 19, 2019

(54) MATERIALS FOR ORGANIC ELECTROLUMINESCENT DEVICES

(71) Applicant: Merck Patent GmbH, Darmstadt (DE)

(72) Inventors: Adam W. Franz, Kelkheim (DE); Rémi M. Anémian, Seoul (KR)

(73) Assignee: Merck Patent GmbH, Darmstadt (DE)

( * ) Notice: Subject to any disclaimer, the term of this patent is extended or adjusted under 35 U.S.C. 154(b) by 451 days.

(21) Appl. No.: 14/885,345

(22) Filed: Oct. 16, 2015

(65) Prior Publication Data

US 2016/0096809 A1    Apr. 7, 2016

Related U.S. Application Data

(63) Continuation of application No. 13/510,476, filed as application No. PCT/EP2010/006343 on Oct. 18, 2010, now Pat. No. 9,187,456.

(30) Foreign Application Priority Data

Nov. 17, 2009   (DE) .................. 10 2009 053 644

(51) Int. Cl.
| | |
|---|---|
| *H01L 51/50* | (2006.01) |
| *C07D 251/24* | (2006.01) |
| *C07D 251/16* | (2006.01) |
| *C07D 251/22* | (2006.01) |
| *C07D 403/10* | (2006.01) |
| *C07D 403/14* | (2006.01) |
| *C07D 405/10* | (2006.01) |

(Continued)

(52) U.S. Cl.
CPC ......... *C07D 251/24* (2013.01); *C07D 251/16* (2013.01); *C07D 251/22* (2013.01); *C07D 403/10* (2013.01); *C07D 403/14* (2013.01); *C07D 405/10* (2013.01); *C07D 405/14* (2013.01); *C07D 409/10* (2013.01); *C07D 409/14* (2013.01); *C09B 57/00* (2013.01); *C09K 11/025* (2013.01); *H01L 51/0052* (2013.01); *H01L 51/0065* (2013.01); *H01L 51/0067* (2013.01); *H01L 51/0068* (2013.01); *H05B 33/20* (2013.01); *C09K 2211/1007* (2013.01); *C09K 2211/1011* (2013.01); *C09K 2211/1059* (2013.01); *H01L 51/0003* (2013.01); *H01L 51/0085* (2013.01); *H01L 51/5016* (2013.01); *H01L 51/5072* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| | | |
|---|---|---|
| 6,653,438 B1 | 11/2003 | Spreitzer et al. |
| 2006/0186797 A1 | 8/2006 | Nishiyama et al. |
| | (Continued) | |

FOREIGN PATENT DOCUMENTS

| | | |
|---|---|---|
| JP | 2007-049055 A | 2/2007 |
| JP | 2007-223904 A | 9/2007 |
| | (Continued) | |

*Primary Examiner* — Gregory D Clark
(74) *Attorney, Agent, or Firm* — Drinker Biddle & Reath LLP

(57) ABSTRACT

The present invention relates to fluorene derivatives and to electronic devices in which these compounds are used as matrix material in the emitting layer and/or as hole-transport material and/or as electron-blocking or exciton-blocking material and/or as electron-transport material.

17 Claims, 1 Drawing Sheet

(51) Int. Cl.
*C07D 405/14* (2006.01)
*C07D 409/10* (2006.01)
*C07D 409/14* (2006.01)
*H01L 51/00* (2006.01)
*H05B 33/20* (2006.01)
*C09B 57/00* (2006.01)
*C09K 11/02* (2006.01)

(56) References Cited

U.S. PATENT DOCUMENTS

| | | |
|---|---|---|
| 2007/0141390 A1 | 6/2007 | Coggan et al. |
| 2011/0037027 A1 | 2/2011 | Stoessel et al. |
| 2011/0210322 A1 | 9/2011 | Ishii et al. |
| 2012/0056171 A1 | 3/2012 | Kim et al. |

FOREIGN PATENT DOCUMENTS

| | | |
|---|---|---|
| JP | 2009-516652 A | 4/2009 |
| JP | 2009-182088 A | 8/2009 |
| JP | 2009-210149 A | 9/2009 |
| JP | 2010-111851 A | 5/2010 |
| JP | 2012-510757 A | 5/2012 |
| JP | 2012-526804 A | 11/2012 |
| WO | WO-00/22026 A1 | 4/2000 |
| WO | WO-2007069847 A1 | 6/2007 |
| WO | WO-2009124627 A1 | 10/2009 |
| WO | WO-2010131930 A2 | 11/2010 |

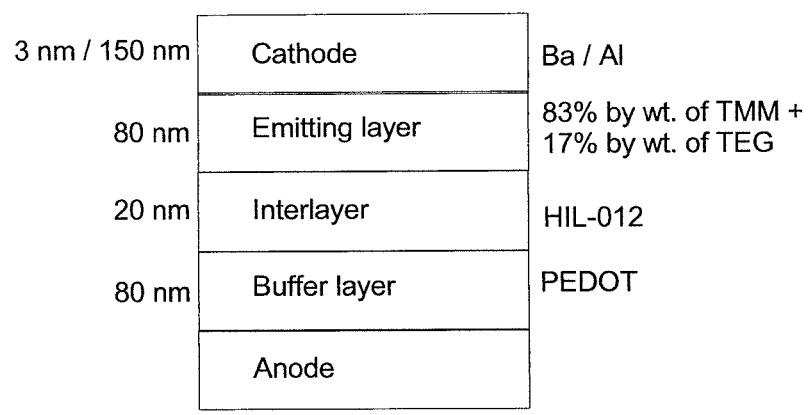

MATERIALS FOR ORGANIC ELECTROLUMINESCENT DEVICES

RELATED APPLICATIONS

This application is a continuation of U.S. patent application Ser. No. 13/510,476, filed May 17, 2012, which is a national stage application (under 35 U.S.C. § 371) of PCT/EP2010/006343, filed Oct. 18, 2010, which claims benefit of German Patent Application No. 10 2009 053 644.2, filed Nov. 17, 2009.

The present invention relates to organic semiconductors and to the use thereof in electronic devices, in particular in organic electroluminescent devices.

BACKGROUND OF THE INVENTION

Organic semiconductors are being developed for a number of different electronic applications. The structure of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136. However, further improvements are still desirable for use of these devices for high-quality and long-lived displays. Thus, there is currently still a need for improvement, in particular, in the lifetime and efficiency of blue-emitting organic electroluminescent devices. Furthermore, it is necessary for the compounds to have high thermal stability and a high glass-transition temperature and to be sublimable without decomposition. In particular for use at elevated temperature, a high glass-transition temperature is essential for achieving long lifetimes.

There therefore continues to be a demand for improved materials, for example host materials for fluorescent and phosphorescent emitters, but further improvements are also desirable, in particular, in charge-transport materials, i.e. hole- and electron-transport materials, charge-blocking materials and exciton-blocking materials. The properties of these materials in particular are frequently limiting for the lifetime and efficiency of the organic electroluminescent device.

BRIEF SUMMARY OF THE INVENTION

Surprisingly, it has been found that the combination of substituted 9,9-diarylfluorenes with nitrogen-containing 6-membered heteroaromatic groups, in particular triazine, enables high efficiencies and long lifetimes to be achieved.

The present invention therefore relates to these compounds and to the use thereof in electronic devices, in particular in organic electroluminescent devices. Depending on the substitution, the compounds according to the invention are suitable, in particular, as matrix materials for fluorescent or phosphorescent compounds, exciton-blocking materials, hole-blocking materials and electron-transport materials. The materials according to the invention enable an increase in the efficiency with the same or improved lifetime of the electronic device compared with materials in accordance with the prior art. Furthermore, these compounds have high thermal stability. In general, these materials are very highly suitable for use in electronic devices since they have a high glass-transition temperature. The corresponding extended structures, in particular indenofluorene structures and indenocarbazole structures, likewise have very good properties. The good solubility and good film-formation properties make the compounds also particularly suitable for processing from solution.

DETAILED DESCRIPTION OF THE INVENTION

The invention thus relates to compounds of the formula (1)

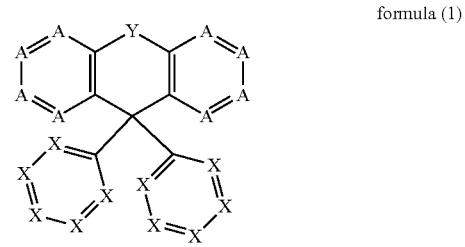

formula (1)

where the following applies to the symbols and indices used:

Y is a single covalent bond, $C(R^1)_2$, CO, O, S, SO, $SO_2$, $NR^3$, $PR^3$ or $P(O)R^3$;

X is on each occurrence, identically or differently, $CR^1$ or N, where a maximum of three groups X in each ring stand for N;

A is on each occurrence, identically or differently, $CR^2$ or N, where a maximum of three groups A in each ring stand for N;

$R^1$, $R^2$ are on each occurrence, identically or differently, H, D, F, Cl, Br, I, CN, $NO_2$, $N(R^4)_3$, $Si(R^4)_3$, $B(OR^4)_2$, $C(=O)R^4$, $P(=O)(R^4)_2$, $S(=O)R^4$, $S(=O)_2R^4$, $-CR^4=CR^4-$, $OSO_2R^4$, a straight-chain alkyl, alkoxy or thioalkoxy group having 1 to 40 C atoms or a branched or cyclic alkyl, alkoxy or thioalkoxy group having 3 to 40 C atoms or an alkenyl or alkynyl group having 2 to 40 C atoms, each of which may be substituted by one or more radicals $R^4$, Where one or more non-adjacent $CH_2$, groups may be replaced by $R^4C=CR^4$, C≡C, $Si(R^4)_2$, $Ge(R^4)_2$, $Sn(R^4)_2$, C=O, C=S, C=Se, $C=NR^4$, $P(=O)(R^4$, SO, $SO_2$, $NR^4$, O, S or $CONR^4$ and where one or more H atoms may be replaced by D, F, Cl, Br, I, CN or $NO_2$, Or an aromatic or heteroaromatic ring system having 5 to 60 aromatic ring atoms, which may in each case be substituted by one or more radicals $R^4$, Or an aryloxy or heteroaryloxy group having 5 to 60 aromatic ring atoms, which may be substituted by one or more radicals $R^4$, Or aralkyl or heteroaralkyl group having 5 to 60 aromatic ring atoms, which may be substituted by one or more radicals $R^4$; two of more adjacent substituents $R^1$ together with the atoms to which they are bonded or two or more adjacent substituents $R^2$ together with the atoms to which they are bonded may also form a mono- or polycyclic, aliphatic or aromatic ring system with one another;

characterised in that at least one substituent $R^1$ which is bonded to X stands for triazine, which may be substituted by one or more radicals $R^4$, or in that at least one substituent $R^2$ stands for a 6-membered heteroaromatic group, which may be substituted by one or more radicals $R^4$, and at least one radical $R^1$ simultaneously stands for an aromatic or heteroaromatic ring system having 5 to 60 aromatic ring atoms, which may be substituted by one or more radicals $R^4$;

$R^3$ is on each occurrence, identically or differently, an aromatic or heteroaromatic ring system having 5 to 60 ring atoms, which may in each case be substituted by one or more radicals $R^4$, Or an aryloxy or heteroaryloxy group having 5 to 60 aromatic ring atoms, which may be substituted by one or more radicals $R^3$, or a combination of these systems;

$R^4$ is on each occurrence, identically or differently, H, D, F, Cl, Br, I, CN, $NO_2$, $N(R^5)_3$, $Si(R^5)_3$, $B(OR^5)_2$, $C(=O)R^5$, $P(=O)(R^5)_2$, $S(=O)R^5$, $S(=O)_2R^5$, $-CR^5=CR^5-$, $OSO_2R^5$, a straight-chain alkyl, alkoxy or thioalkoxy group having 1 to 40 C atoms or a branched or cyclic alkyl, alkoxy or thioalkoxy group having 3 to 40 C atoms or an alkenyl or alkynyl group having 2 to 40 C atoms, each of which may be substituted by one or more radicals $R^5$, where one or more non-adjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^5$, or an aryloxy or heteroaryloxy group having 5 to 60 aromatic ring atoms, which may be substituted by one or more radicals $R^5$, or aralkyl or heteroaralkyl group having 5 to 60 aromatic ring atoms, which may be substituted by one or more radicals $R^5$; two or more radicals $R^4$ here may also form a mono- or polycyclic, aliphatic or aromatic ring system with one another together with the atoms to which they are bonded;

$R^5$ is on each occurrence, identically or differently, an aliphatic, aromatic and/or heteroaromatic hydrocarbon radical having 1 to 20 C atoms; two or more radicals $R^5$ here may also form a mono- or polycyclic, aliphatic or aromatic ring system with one another together with the atoms to which they are bonded.

For clarity, the structure and numbering of 9,9-diphenyl-fluorene is depicted below:

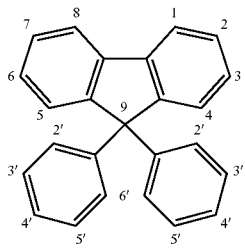 [SMILES: c1ccc(C2(c3ccccc3)c3ccccc3-c3ccccc32)cc1]

An aryl group in the sense of this invention contains 6 to 60 C atoms; a heteroaryl group in the sense of this invention contains 1 to 59 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, pyrene, quinoline, isoquinoline, etc.

An aromatic ring system in the sense of this invention contains 6 to 60 C atoms in the ring system. A heteroaromatic ring system in the sense of this invention contains 1 to 59 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to be aromatic ring systems in the sense of this invention. An aromatic or heteroaromatic ring system is likewise taken to mean systems in which a plurality of aryl or heteroaryl groups are linked to one another by single bonds, for example biphenyl, terphenyl or bipyridine.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl and 2,2,2-trifluoroethyl. An alkenyl group in the sense of this invention is taken to mean, in particular, ethenyl, propenyl, butenyl, pentenyl, cyclopentenyl, hexenyl, cyclohexenyl, heptenyl, cycloheptenyl, octenyl or cyclooctenyl. An alkynyl group in the sense of this invention is taken to mean, in particular, ethynyl, propynyl, butynyl, pentynyl, hexynyl, heptynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and which may be linked to the aromatic or heteroaromatic group via any desired positions, is taken to mean, in particular, groups derived from benzene, naphthalene, anthracene, phenanthrene, benzophenanthrene, benzanthracene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In an embodiment, the compound of the formula (1) corresponds to a compound of the formula (2), (3), (4), (5), (6), (7), (8), (9), (10), (11), (12), (13), (14) or (15):
formula (2)
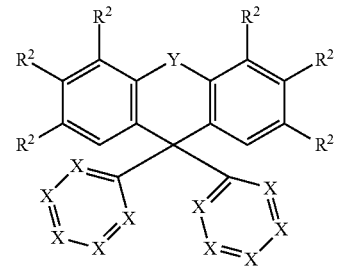
formula (3)
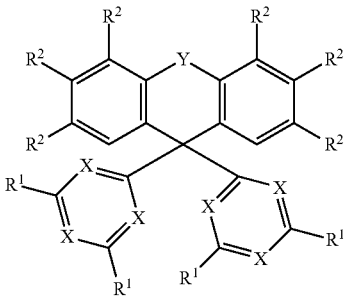
formula (4)
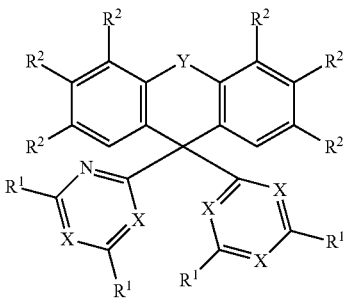
formula (5)
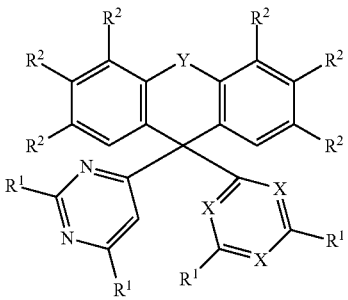
formula (6)
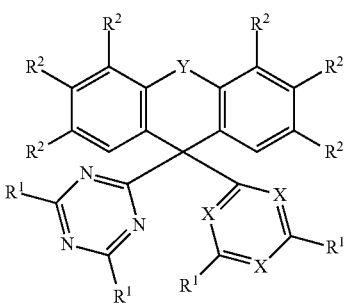
formula (7)
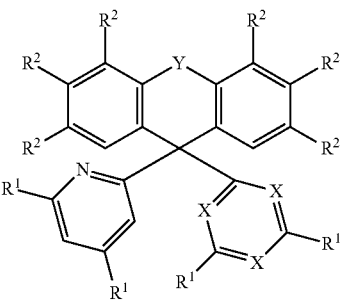
formula (8)
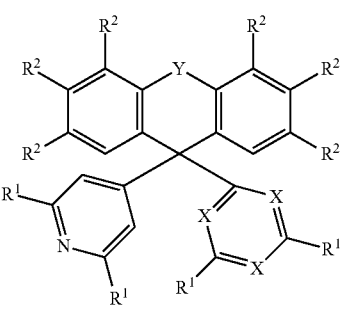
formula (9)
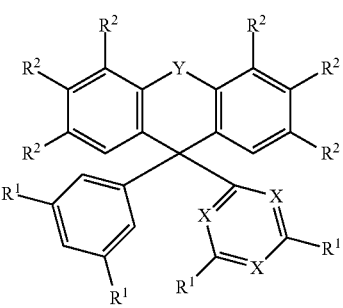
formula (10)
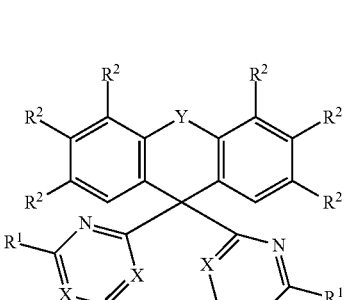
formula (11)
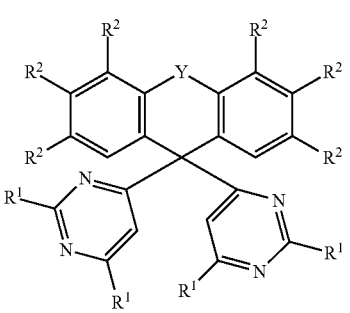

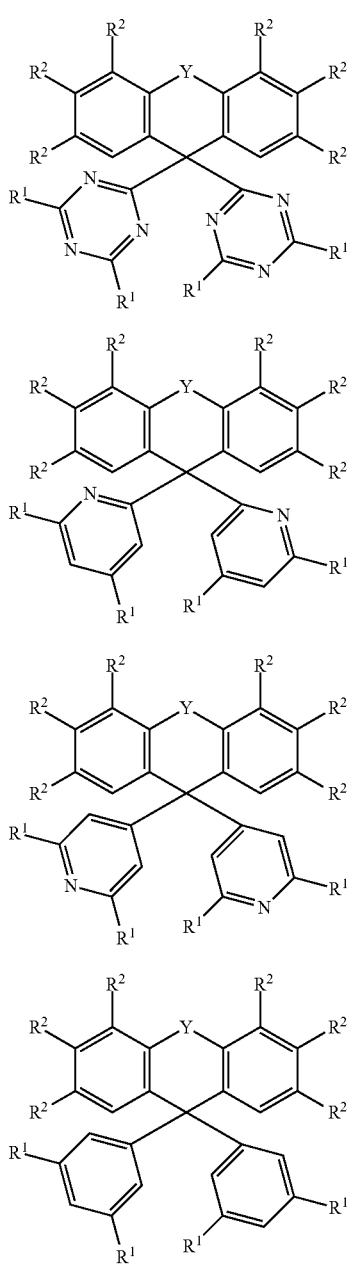

formula (12)

formula (13)

formula (14)

formula (15)

where the symbols and indices used have the meanings indicated above.

In the formulae (2) to (15), X preferably stands, identically or differently on each occurrence, for $CR^1$.

As already described above, the invention is characterised in that at least one group $R^1$ stands for triazine or in that at least one group $R^2$ stands for a 6-membered heteroaromatic group and in that at the same time at least one group $R^1$ stands for an aromatic or heteroaromatic ring system. These may each be substituted by one or more radicals $R^4$.

If at least one group $R^1$ stands for triazine, this is preferably 1,3,5-triazine or 1,2,4-triazine, particularly preferably 1,3,5-triazine, which may in each case be substituted by one or more radicals $R^4$. The radicals $R^4$ which are not equal to hydrogen or deuterium preferably stand for an aromatic or heteroaromatic ring system, particularly preferably for phenyl, biphenyl, terphenyl or quaterphenyl.

If at least one group $R^2$ stands for a 6-membered heteroaromatic group, this is preferably selected from triazine, pyrimidine, pyrazine, pyridazine or pyridine, particularly preferably 1,3,5-triazine or pyrimidine, each of which may be substituted by one or more radicals $R^4$. The radicals $R^4$ which are not equal to hydrogen or deuterium preferably stand for an aromatic or heteroaromatic ring system, particularly preferably for phenyl, biphenyl, terphenyl or quaterphenyl.

Particularly preferred triazine substituents $R^1$ and $R^2$ and pyrimidine substituents $R^2$ are the structures depicted below:

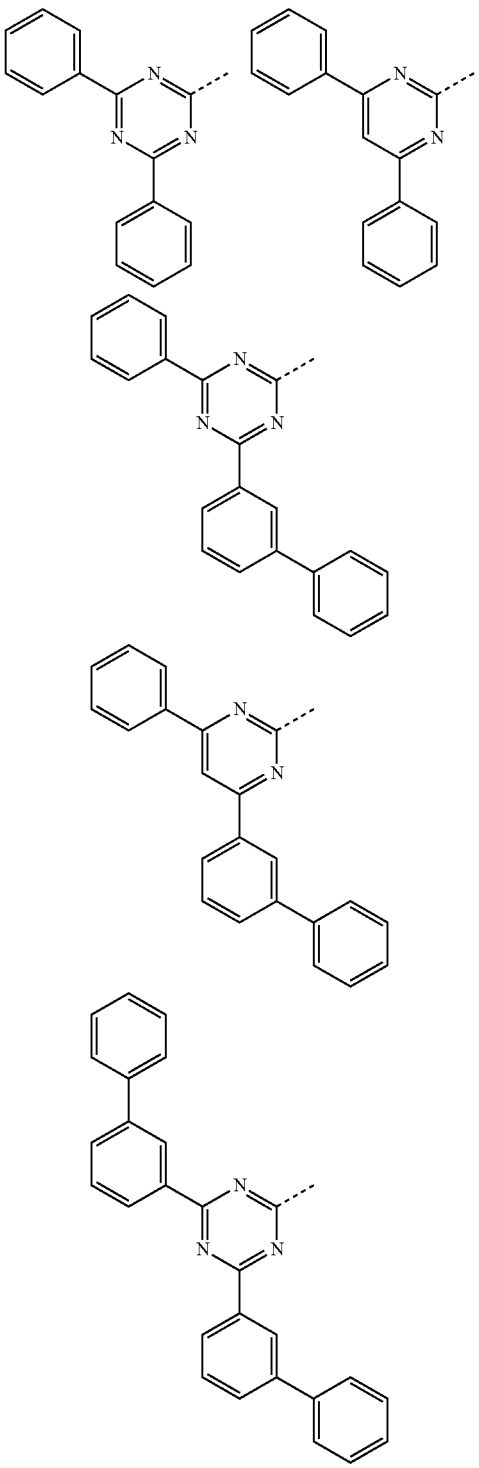

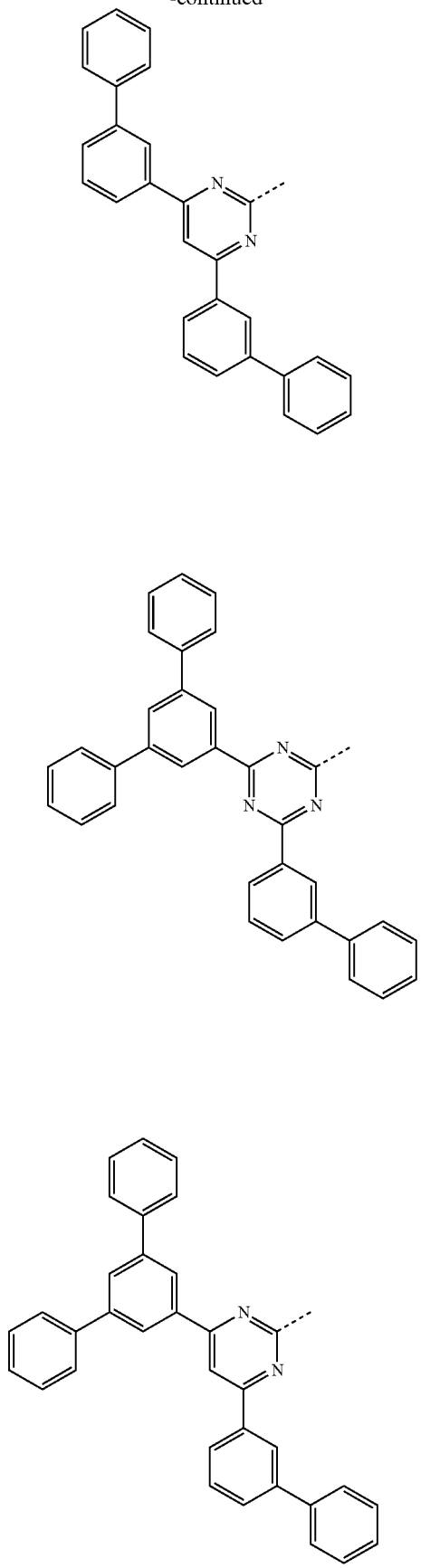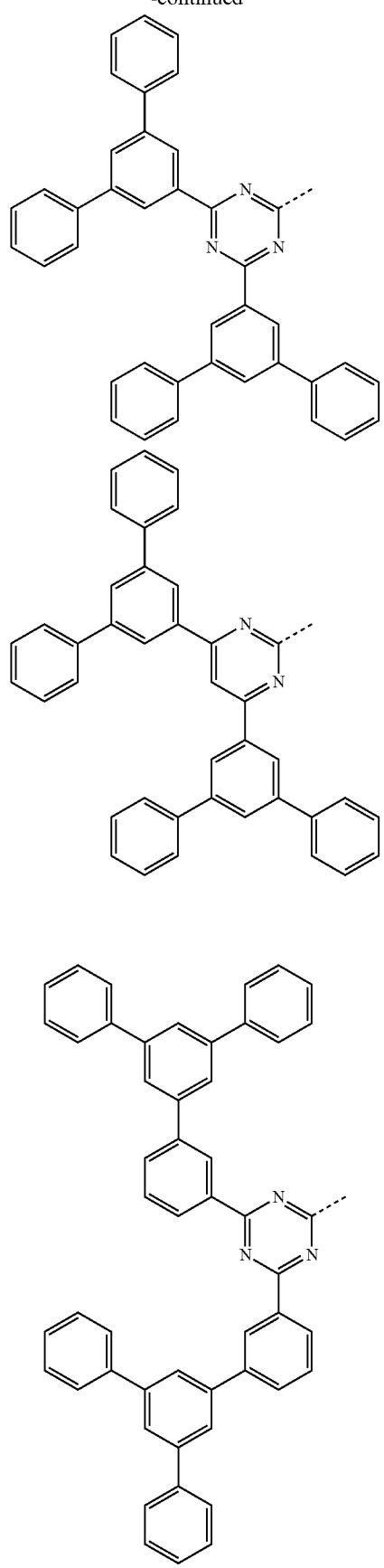

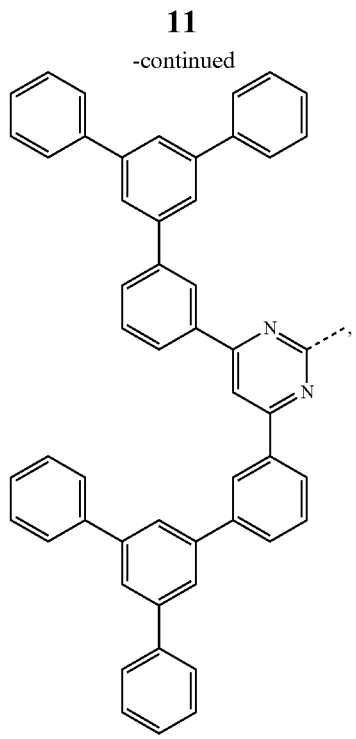

where the dashed bond indicates the link from this group to the skeleton.

In a further preferred embodiment of the invention, the compound of the formula (1) corresponds to the compound of the formula (16) or (17):

formula (16)

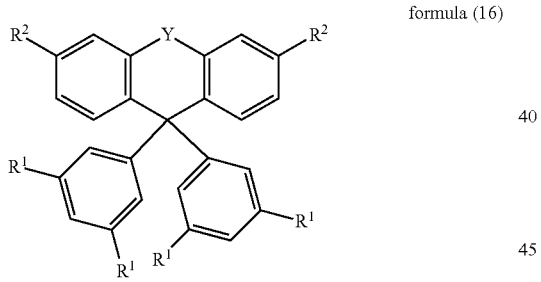

formula (17)

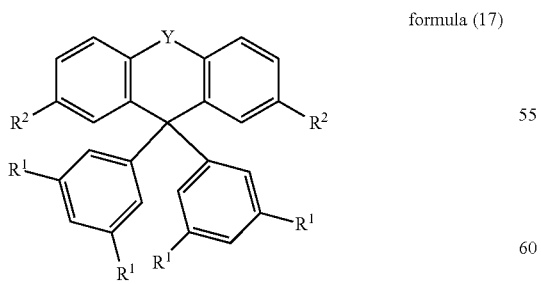

where the symbols and indices used have the meanings indicated above.

Particularly preferred structures for the compound of the formula (1) are compounds (18) to (27):

formula (18)

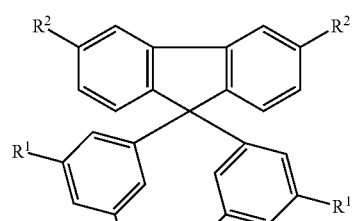

formula (19)

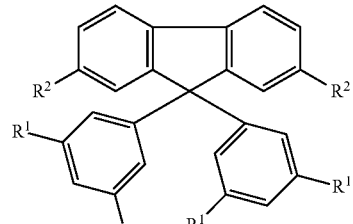

formula (20)

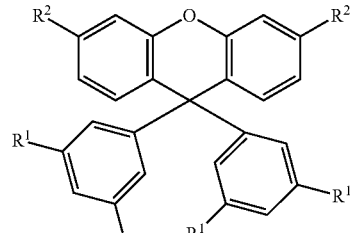

formula (21)

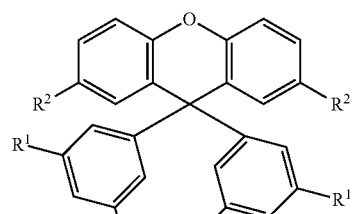

formula (22)

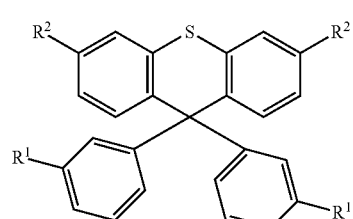

formula (23)

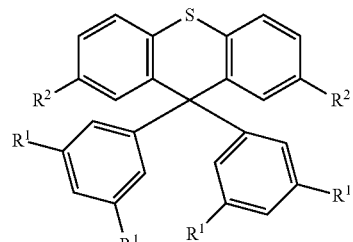

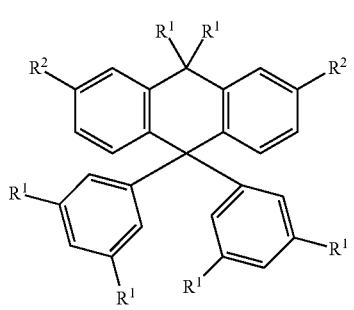

formula (24)

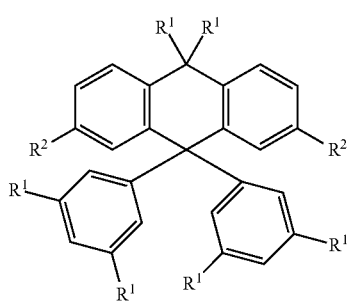

formula (25)

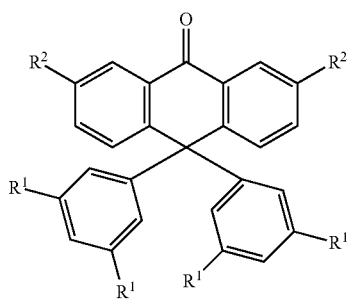

formula (26)

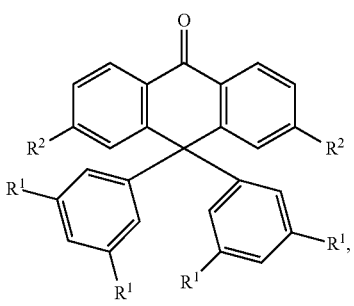

formula (27)

where the symbols and indices used have the meanings indicated above. In the formulae (24) and (25), the radical $R^1$, which is bonded to the carbon bridge, i.e. to the group Y, is in each case, independently of one another, preferably an aliphatic or aromatic hydrocarbon radical, particularly preferably methyl, ethyl, propyl or phenyl, where two phenyl groups may form a ring with one another and may thus form a spiro system.

Further particularly preferred compounds are compounds (28) to (34) shown below:

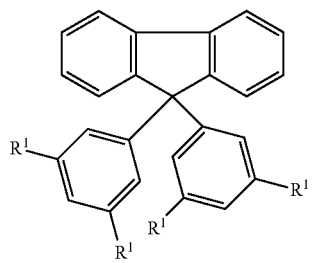

formula (28)

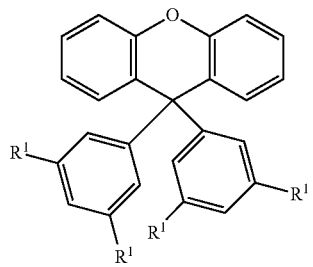

formula (29)

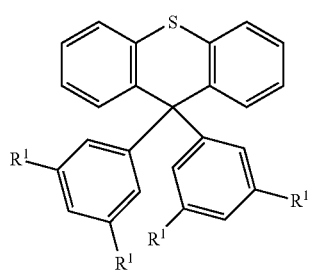

formula (30)

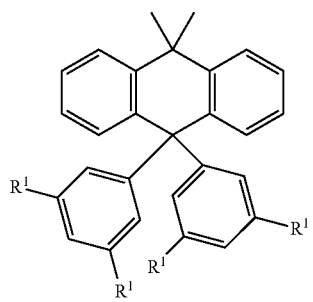

formula (31)

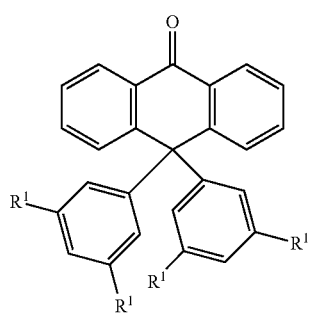

formula (32)

formula (33)

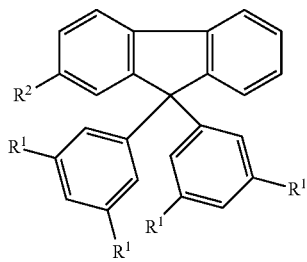

formula (34)

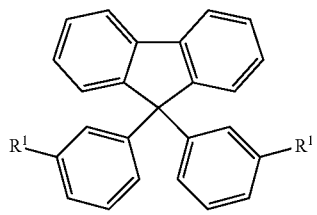

where the symbols and indices used have the meanings indicated above. In compound (33), the radicals $R^1$ are particularly preferably selected in such a way that $R^1$ denotes an aromatic ring system and the radical $R^2$ contains a nitrogen-containing 6-membered heteroaromatic group, in particular substituted or unsubstituted 1,3,5-triazine. Substituents on the triazine are preferably aromatic groups.

Examples of preferred compounds of the formula (1) are structures (1) to (122) depicted below.

(1)

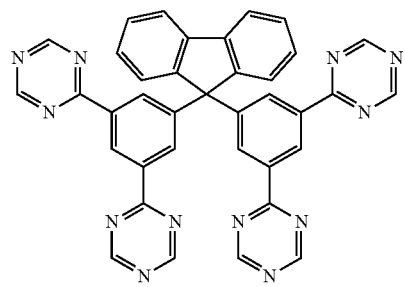

(2)

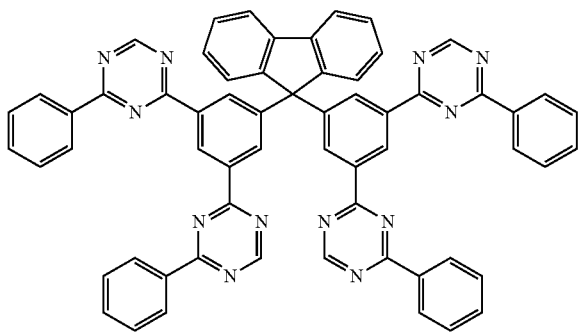

(3)

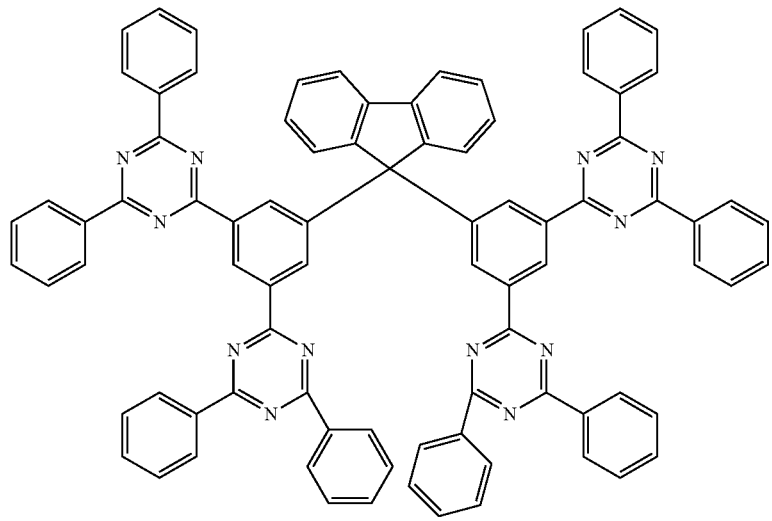

(4)
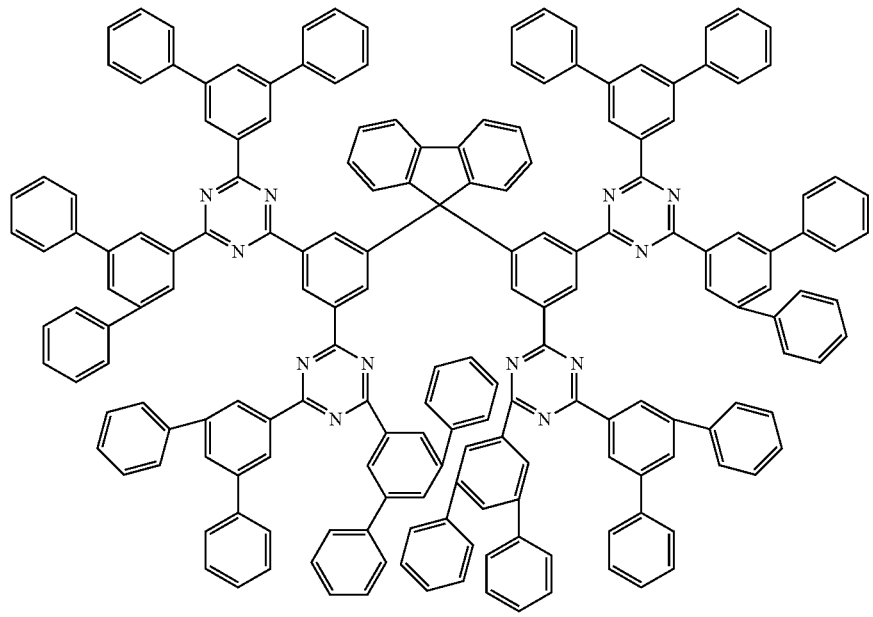
(5)
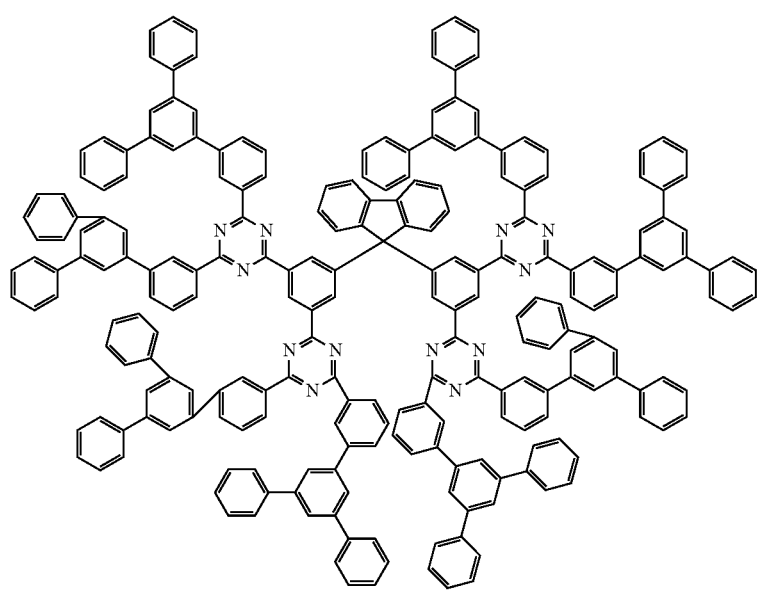

-continued
(6)
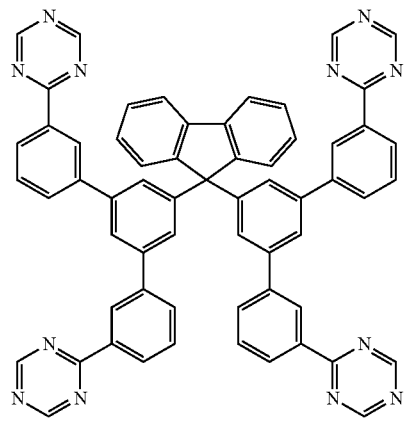
(7)
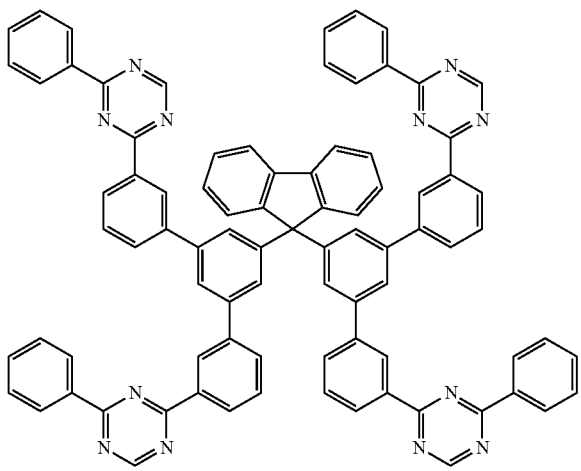
(8)
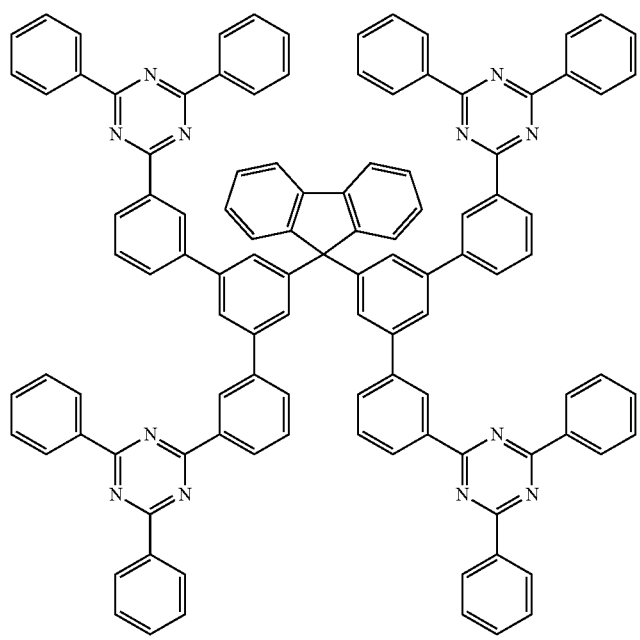

(9)
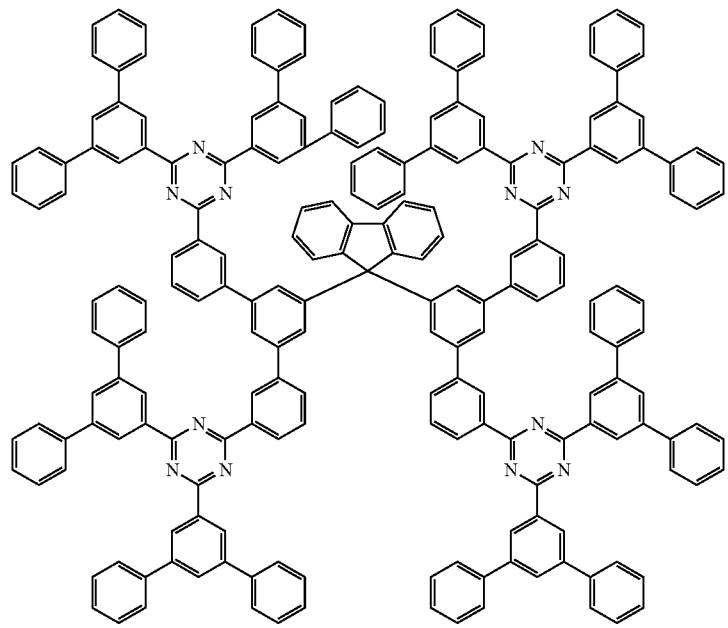
(10)
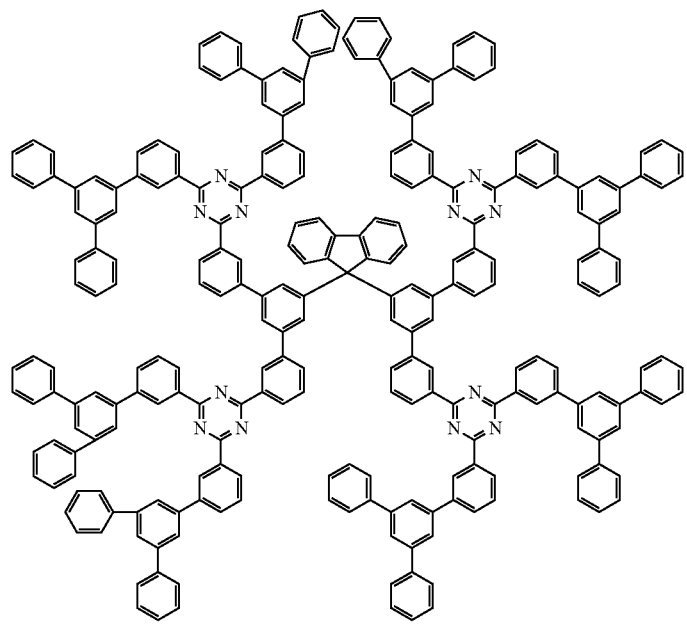
(11)
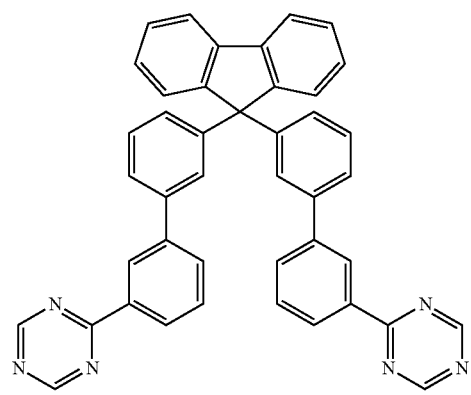
(12)
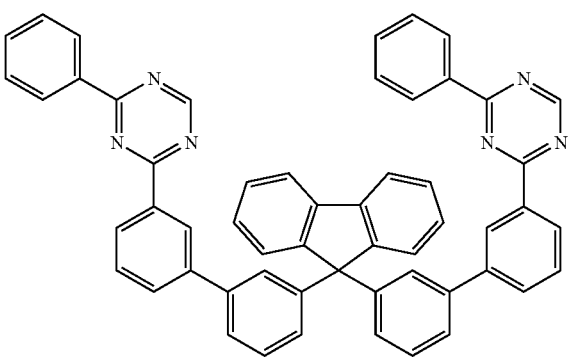

(13)
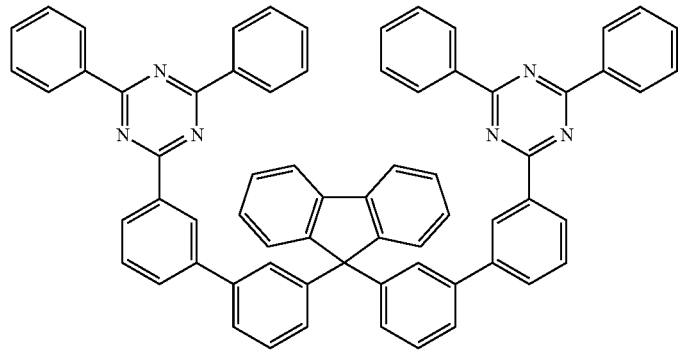
(14)
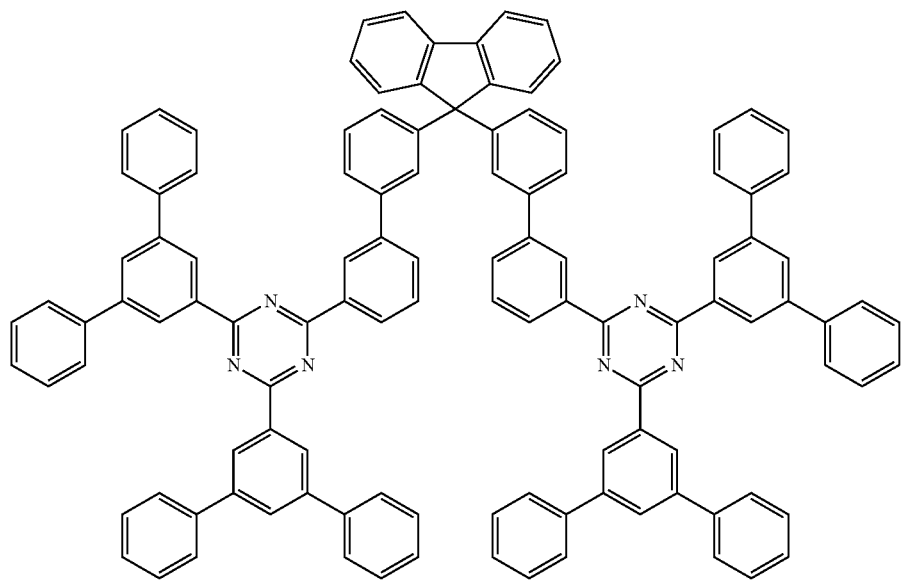
(15)
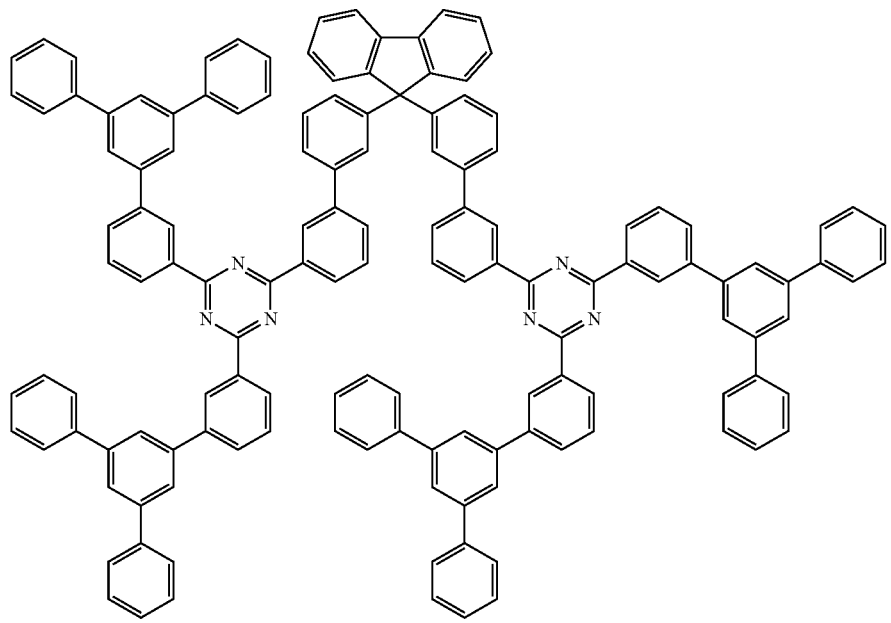

-continued
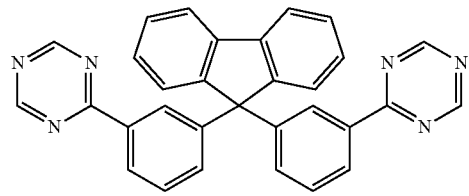
(16)
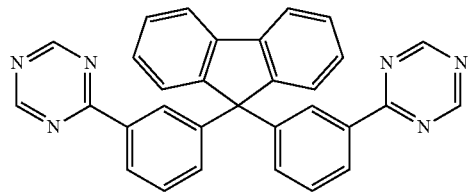
(17)
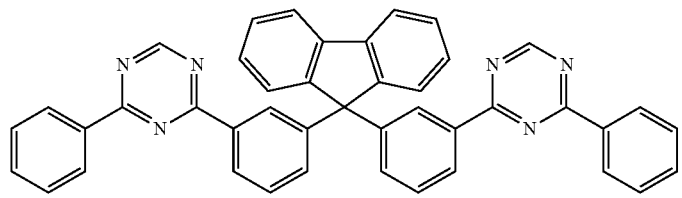
(18)
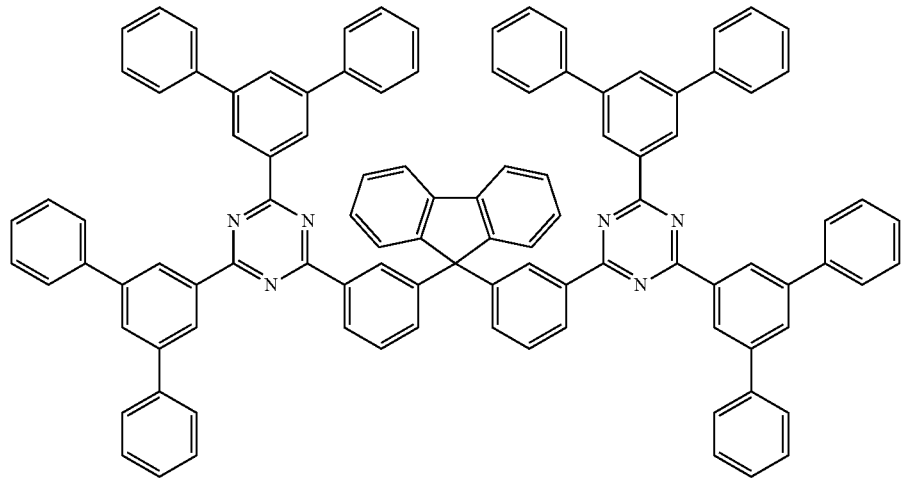
(19)
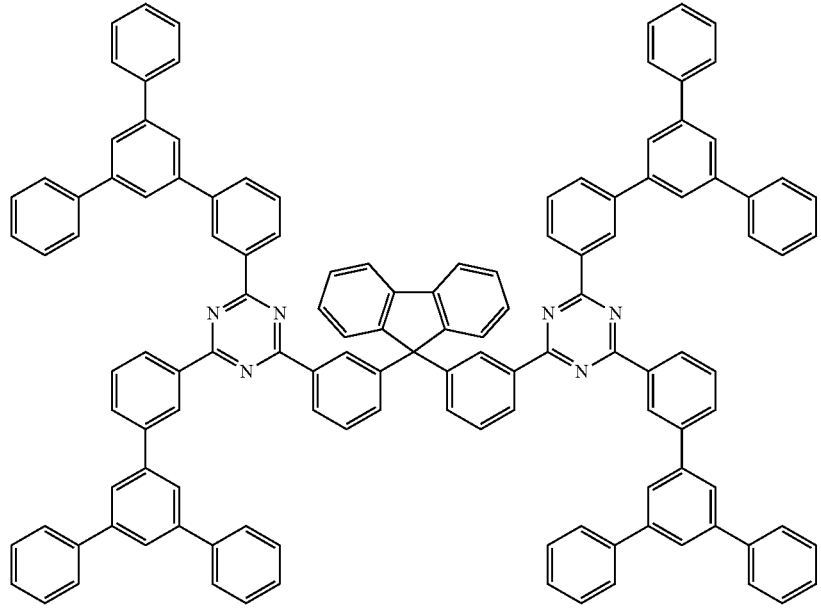
(20)

-continued
(21)
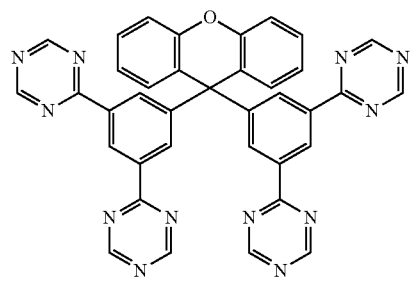
(22)
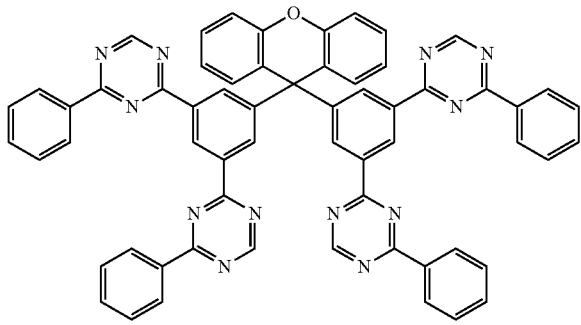
(23)
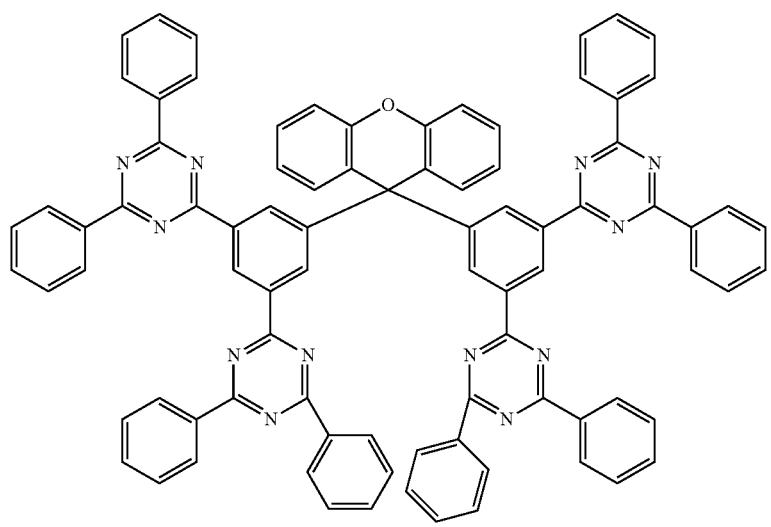
(24)
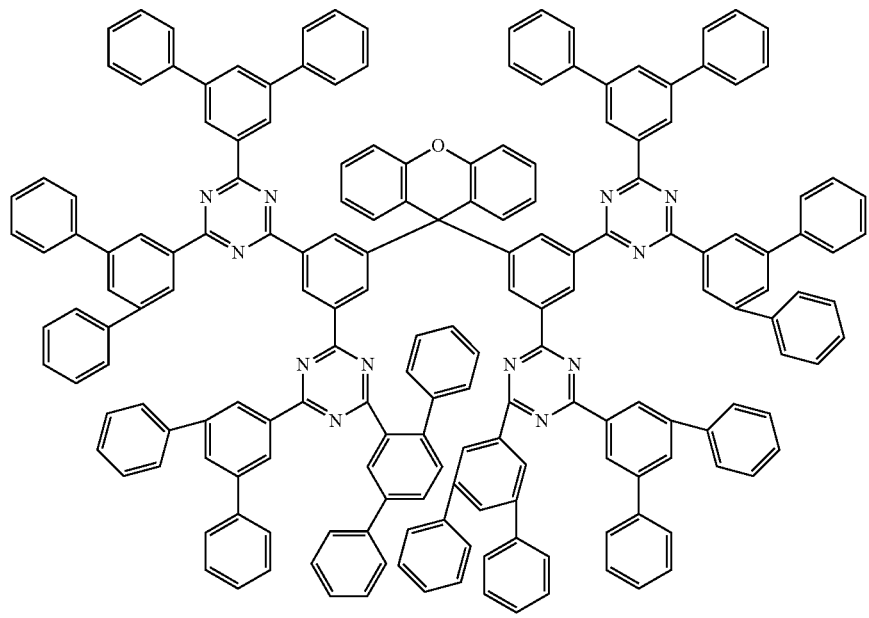

(25)
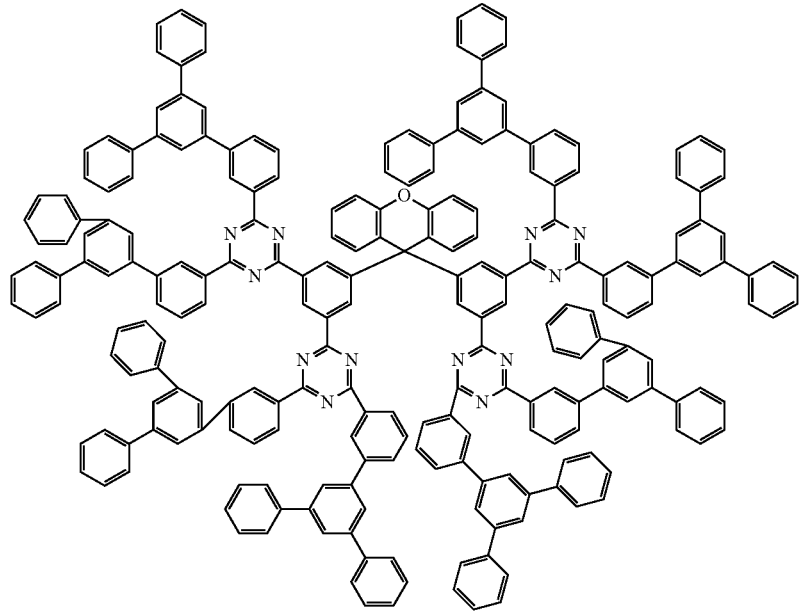
(26) (27)
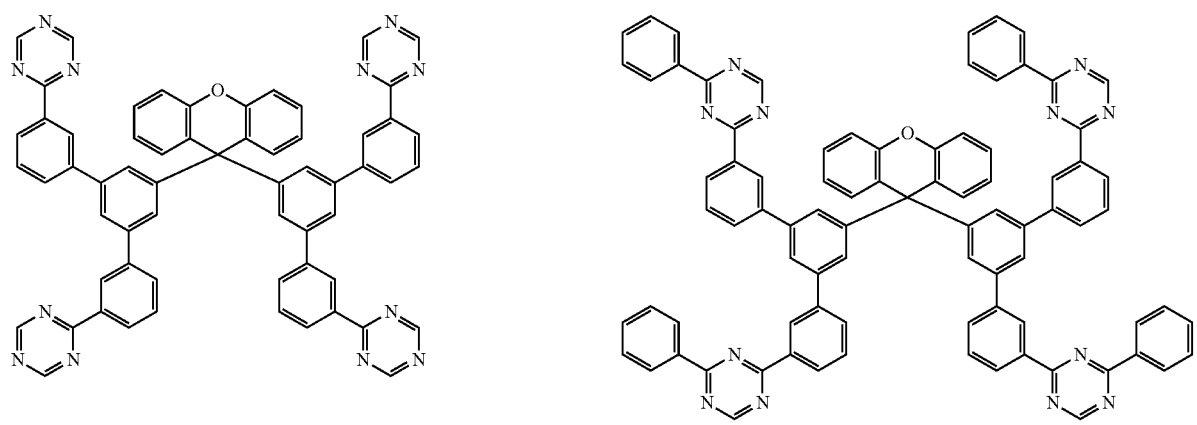
(28)
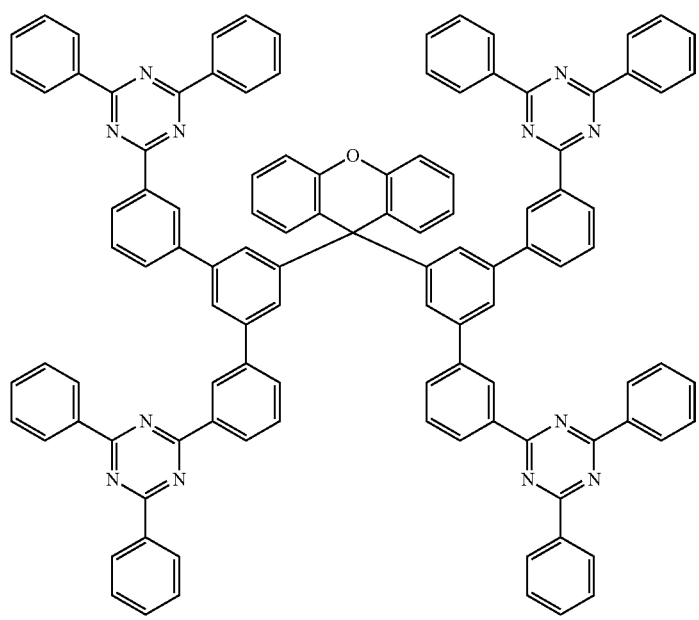

-continued
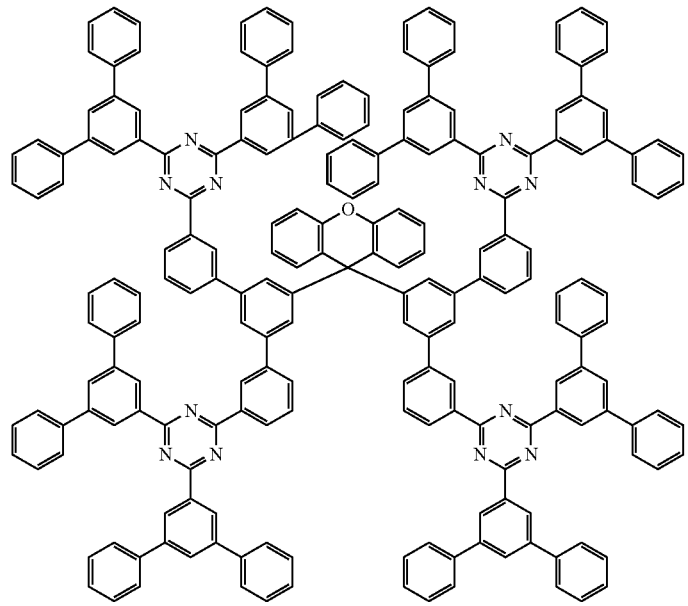
(29)
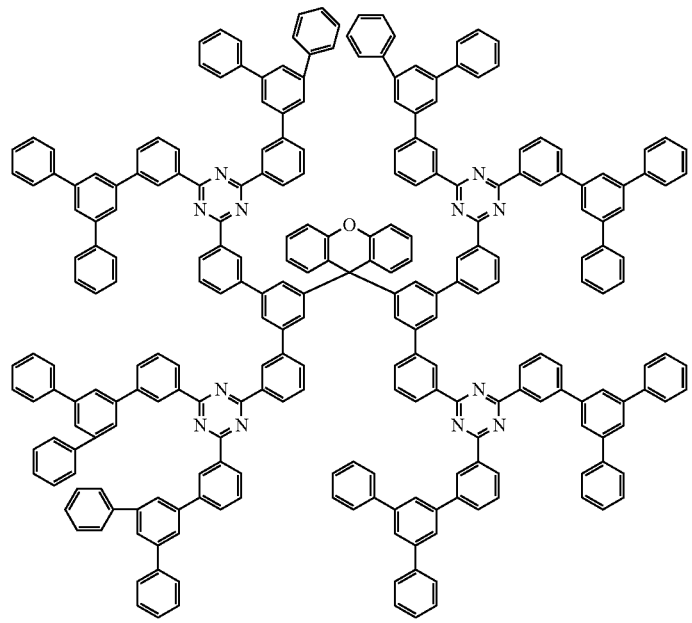
(30)
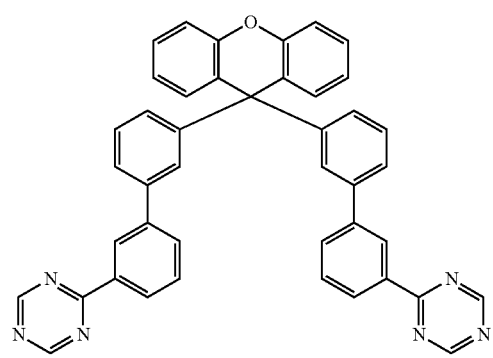
(31)
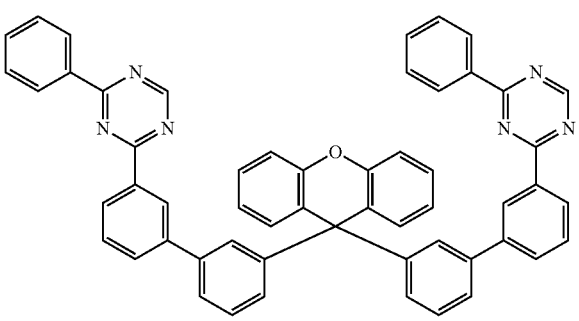
(32)

(33)
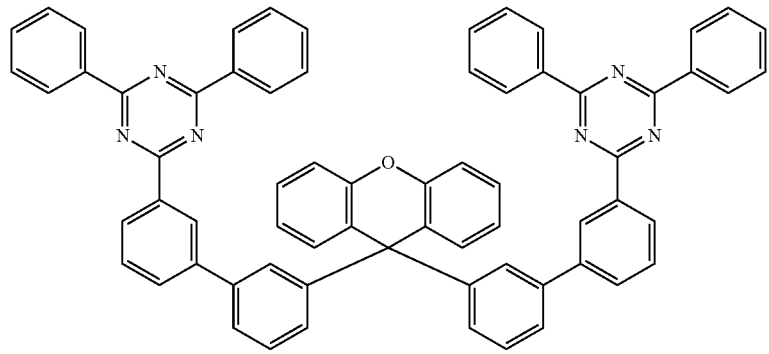
(34)
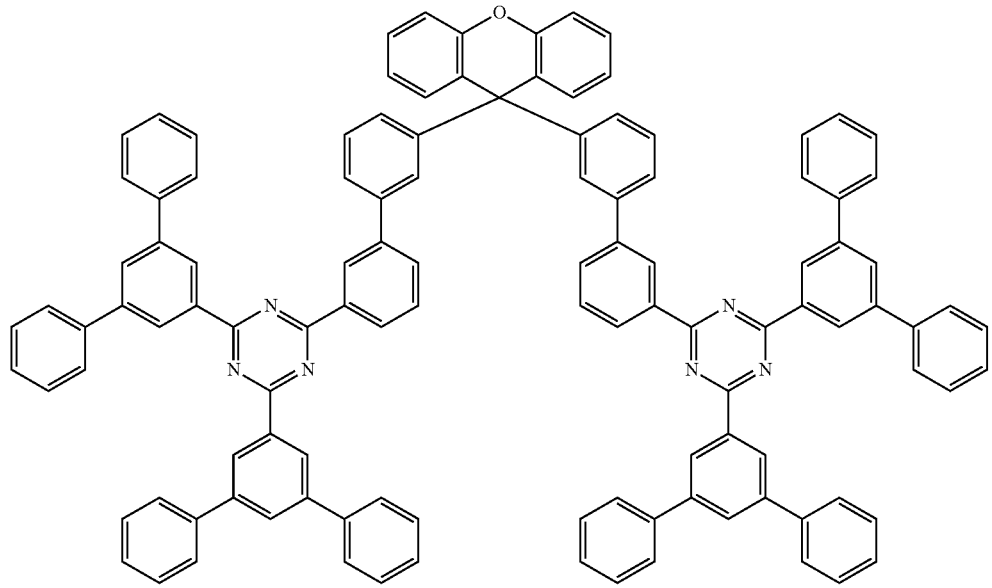
(35)
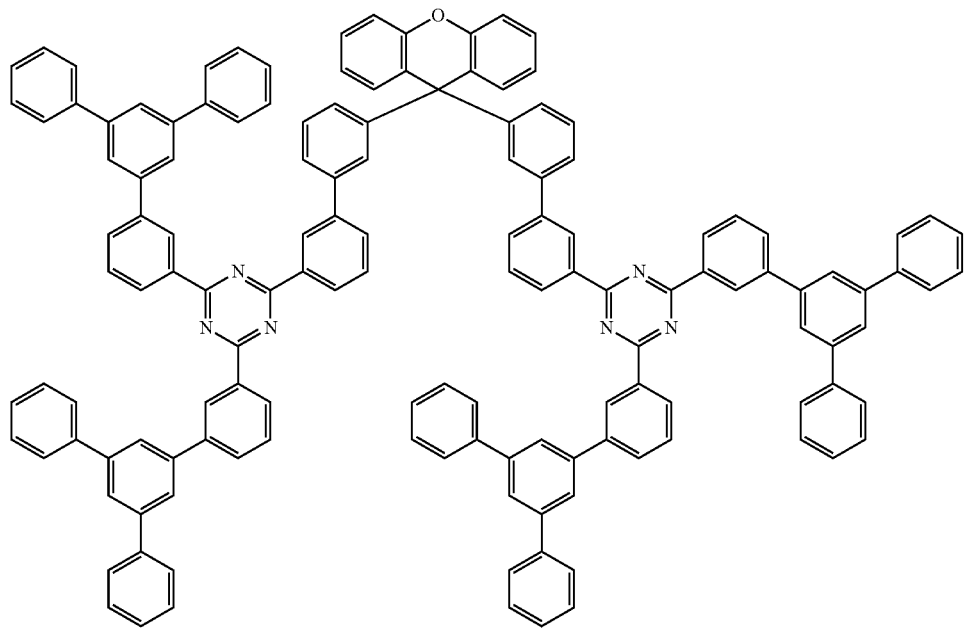

-continued
(36)
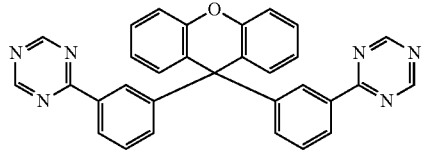
(37)
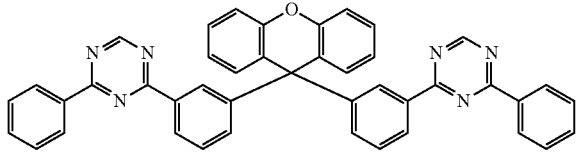
(38)
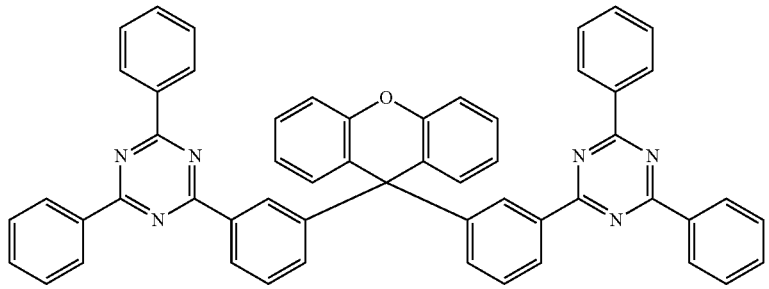
(39)
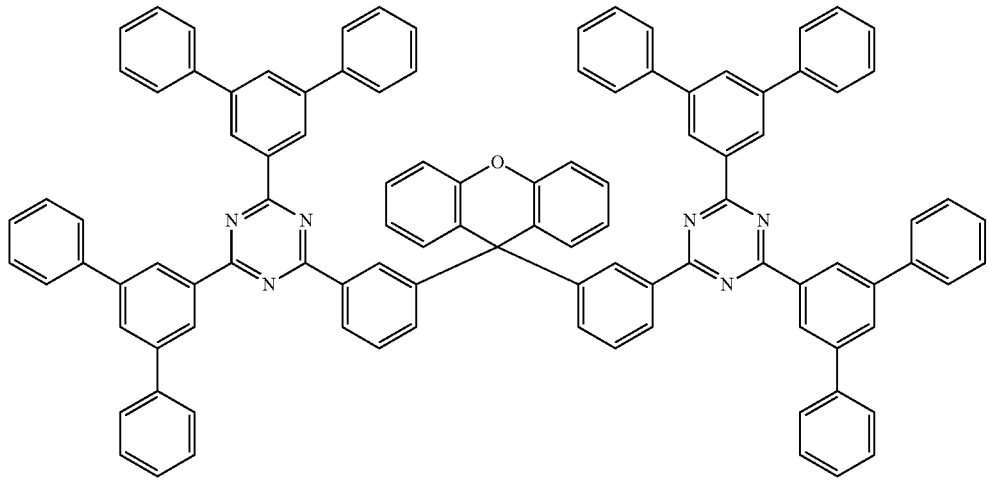
(40)
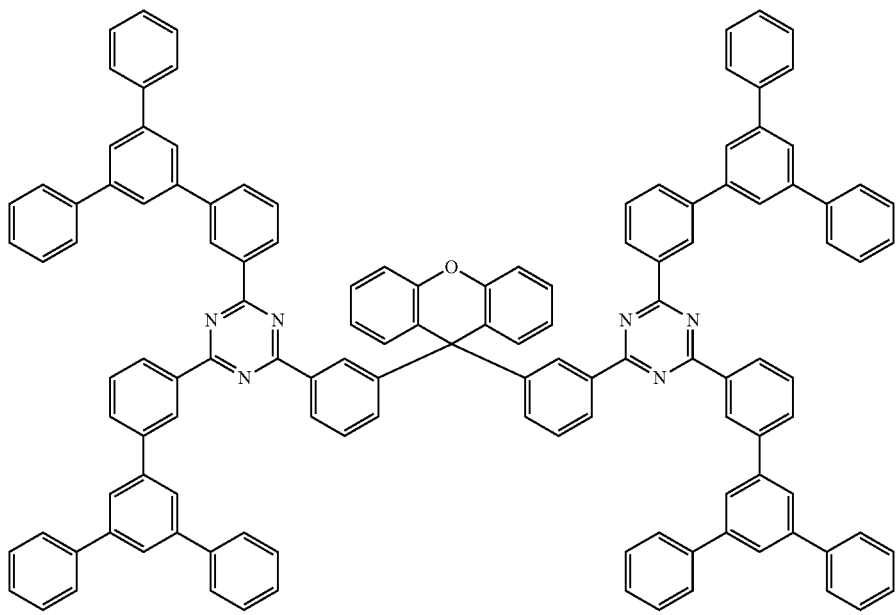

(41)
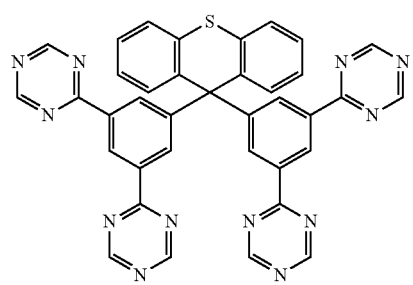
(42)
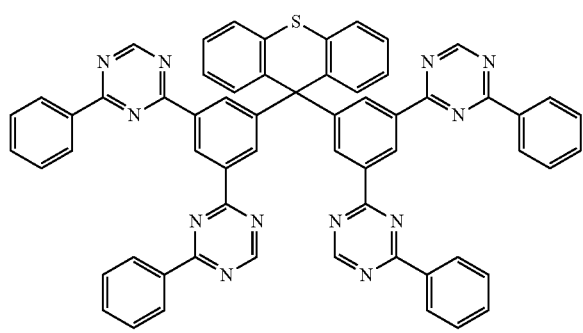
(43)
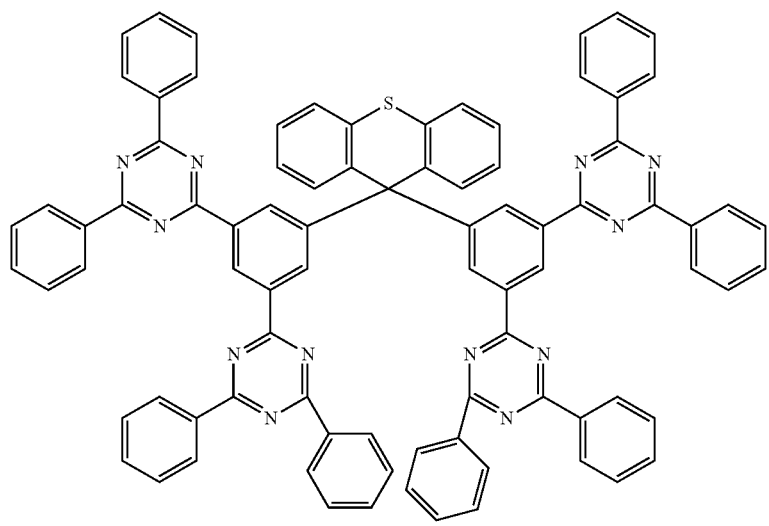
(44)
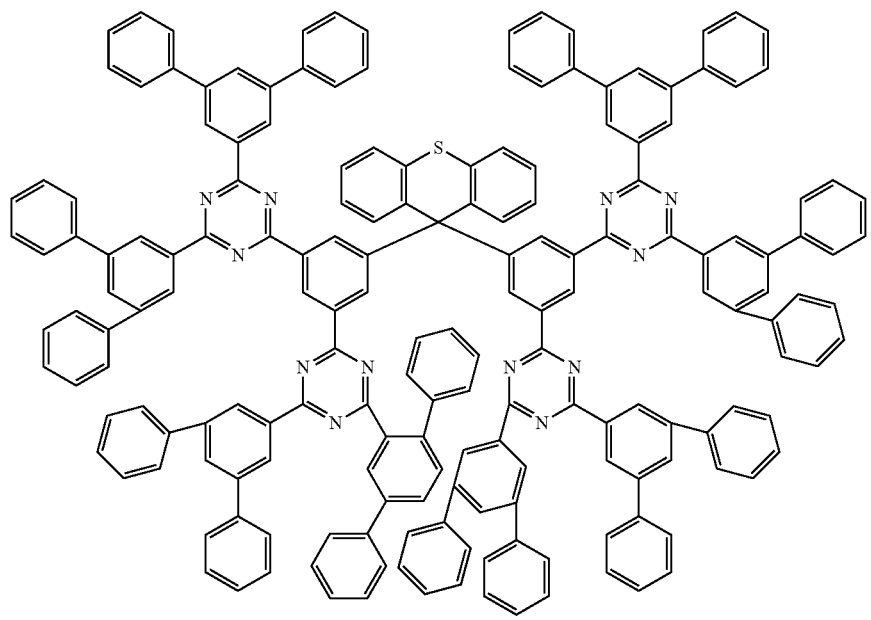

(45)
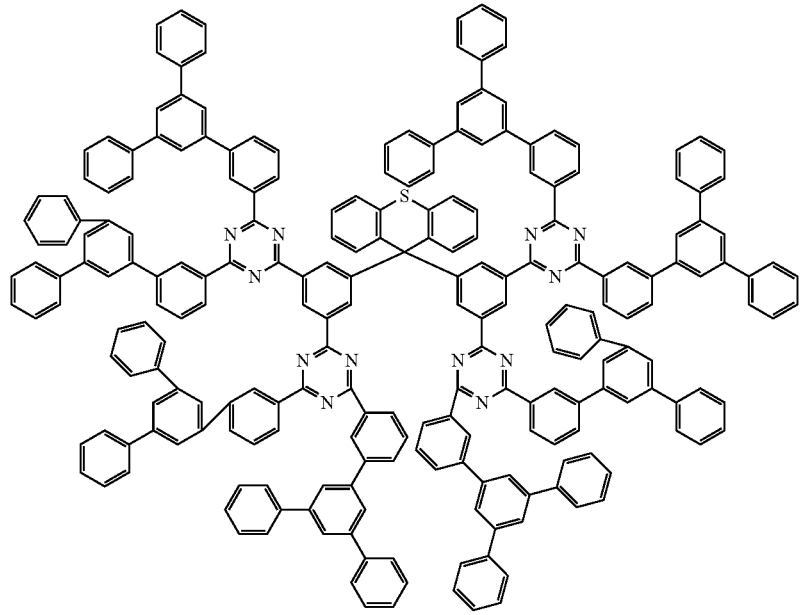
(46)
(47)
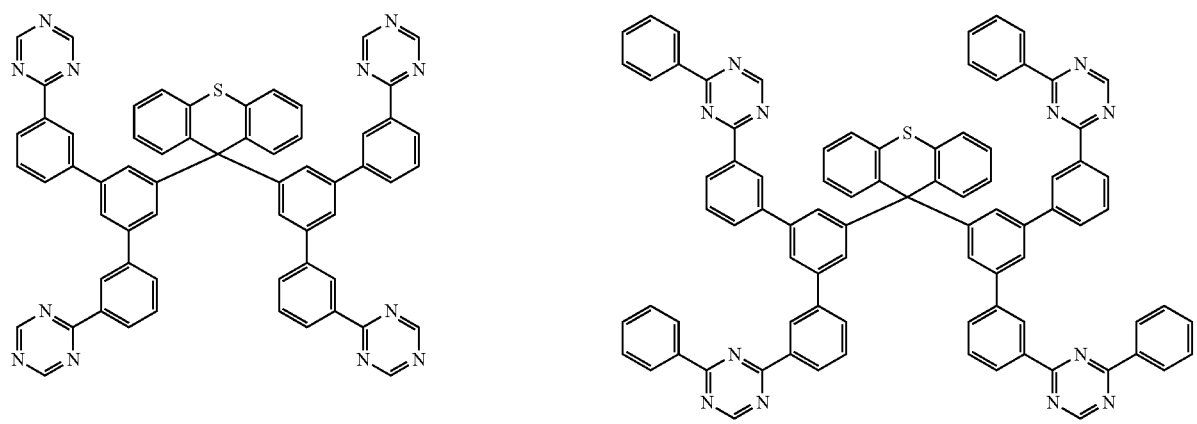
(48)
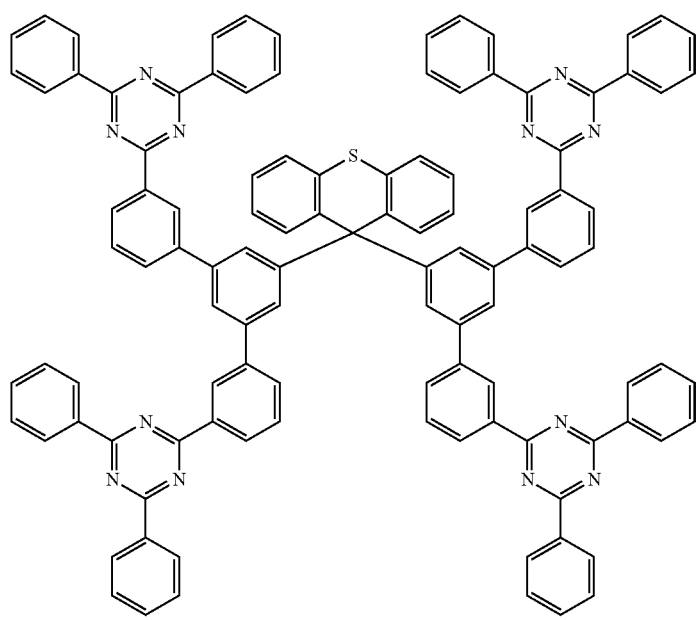

(49)
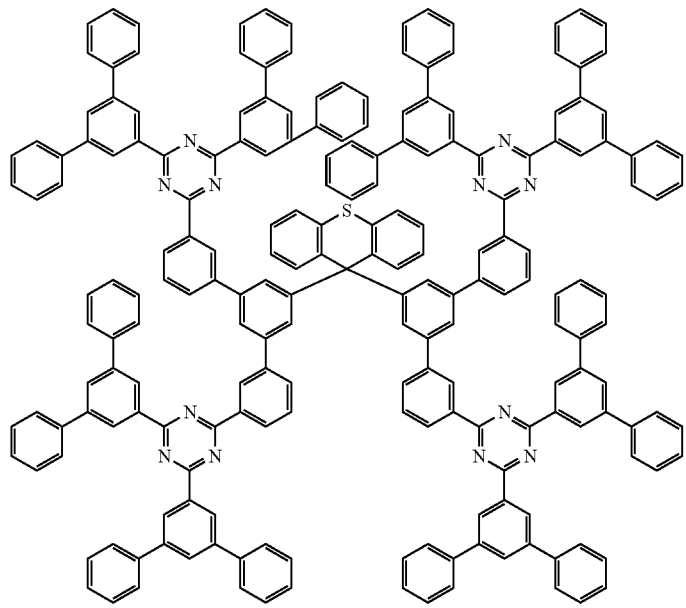
(50)
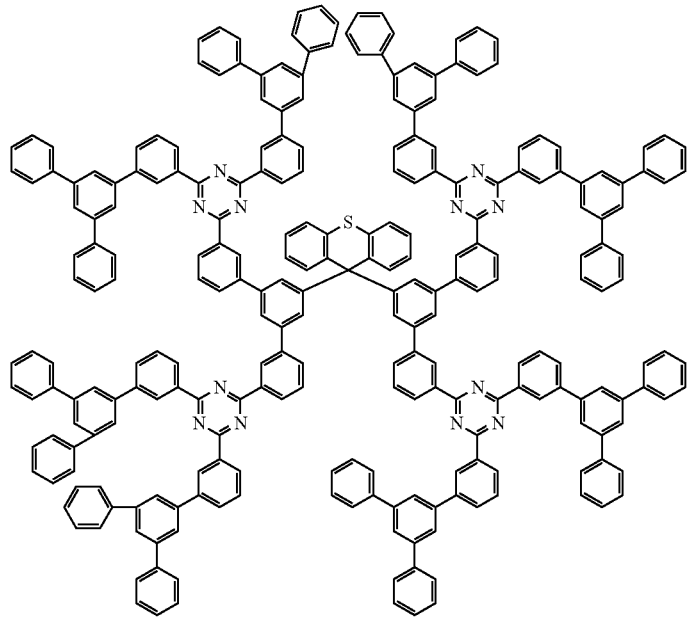
(51)
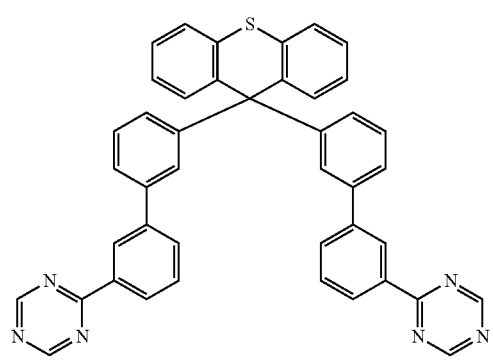
(52)
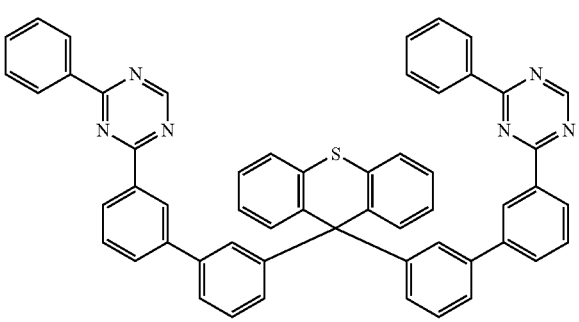

(53)
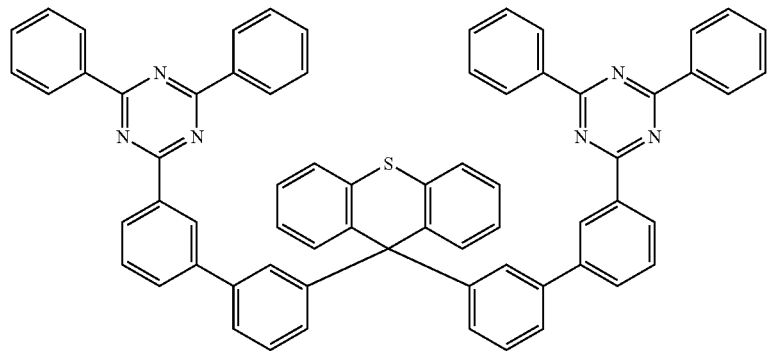
(54)
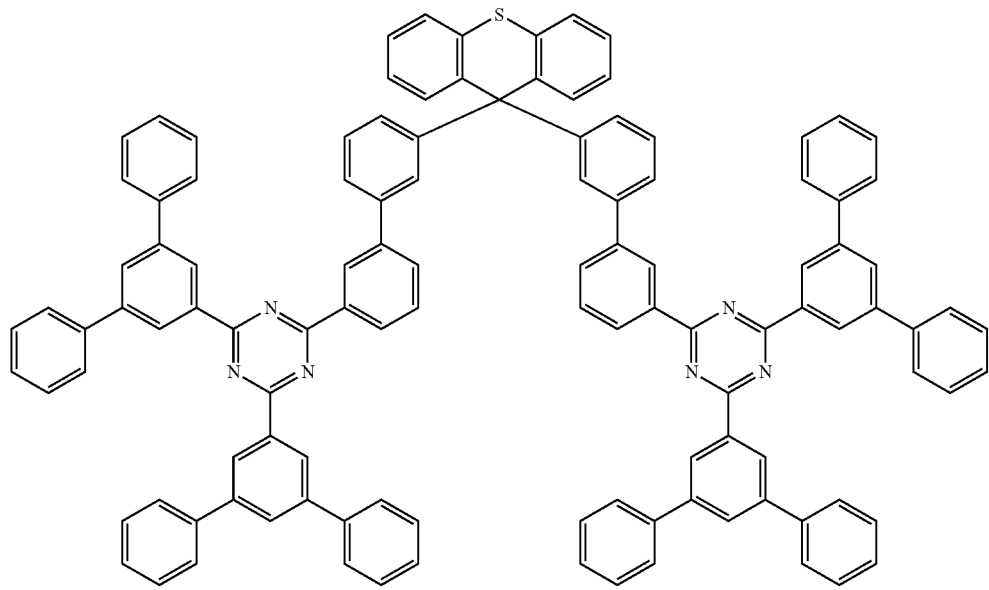
(55)
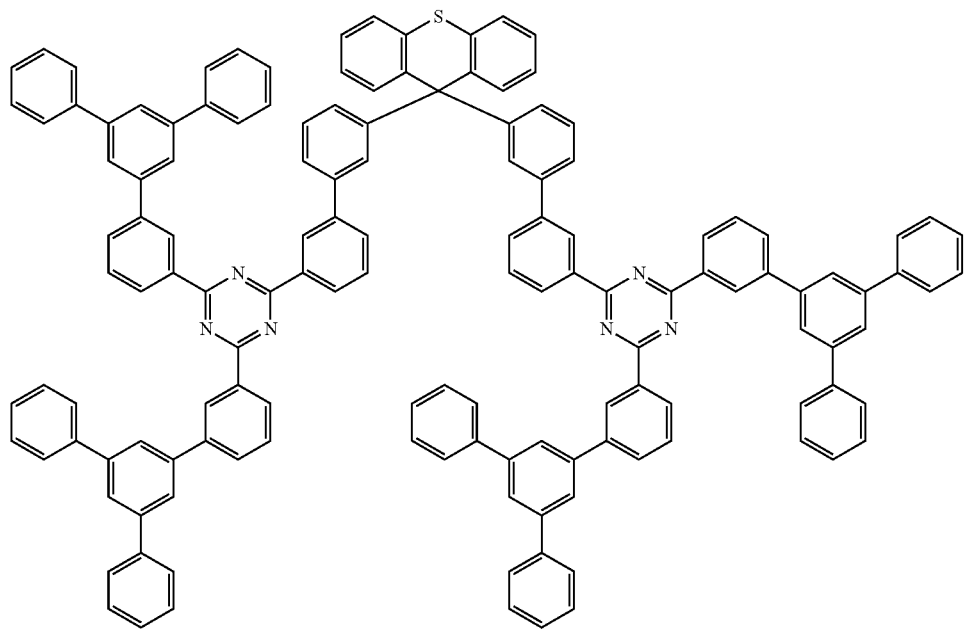

-continued
(56)
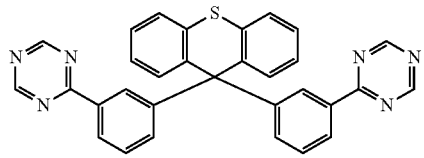
(57)
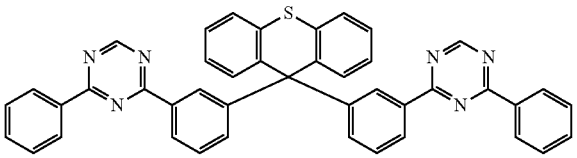
(58)
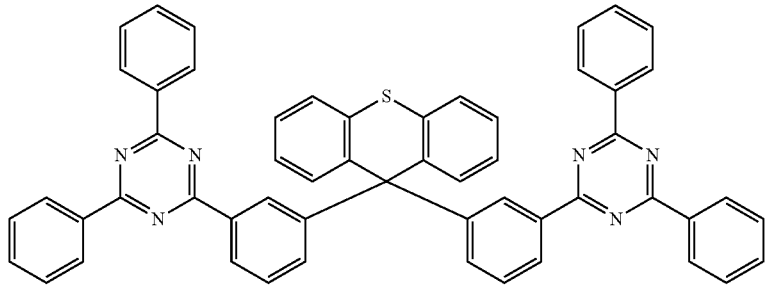
(59)
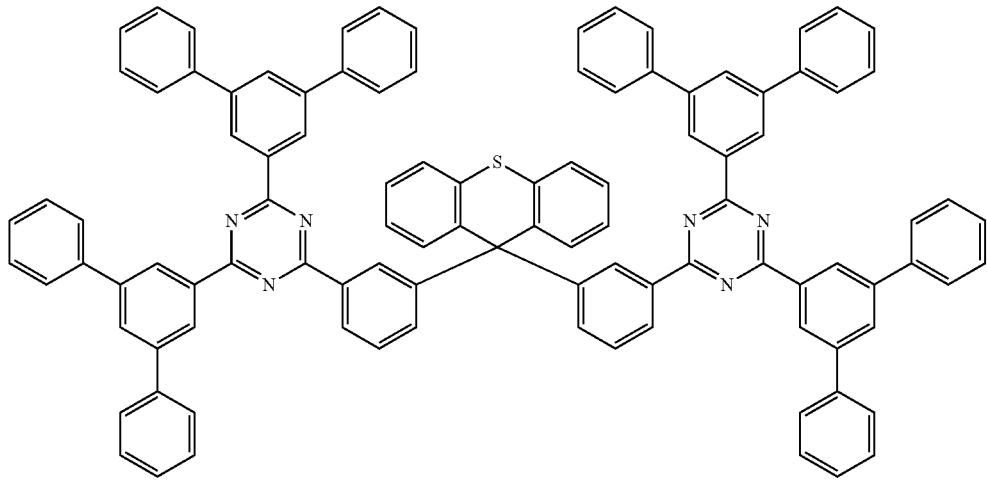
(60)
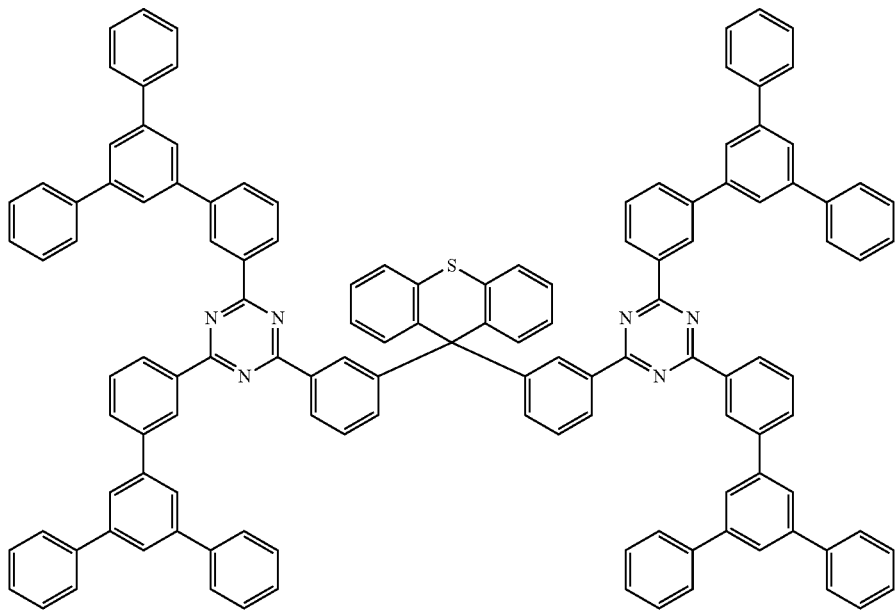

-continued
(61)
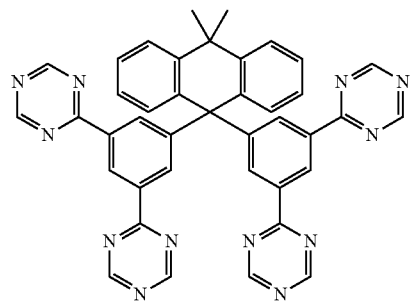
(62)
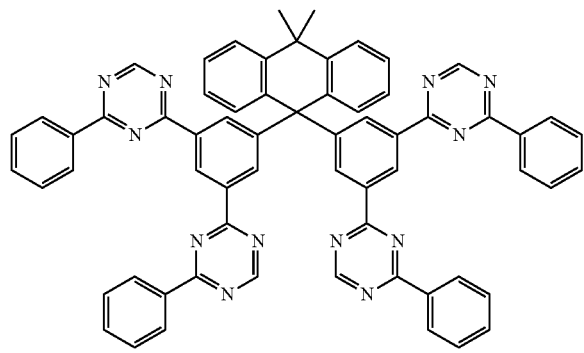
(63)
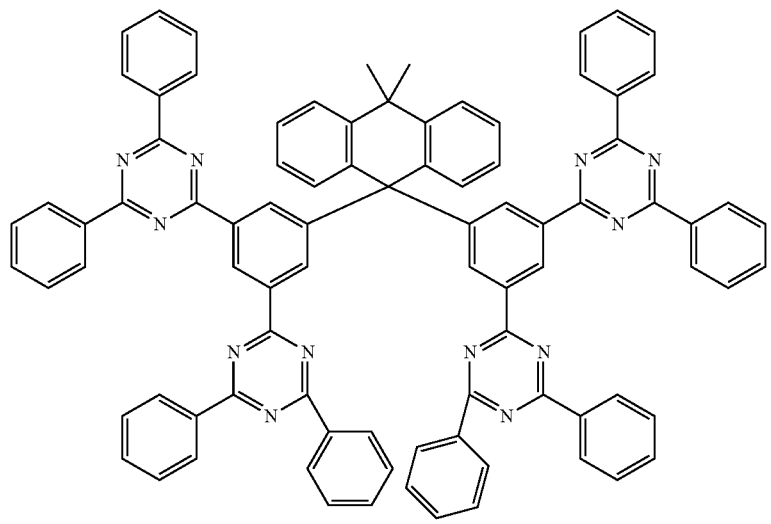
(64)
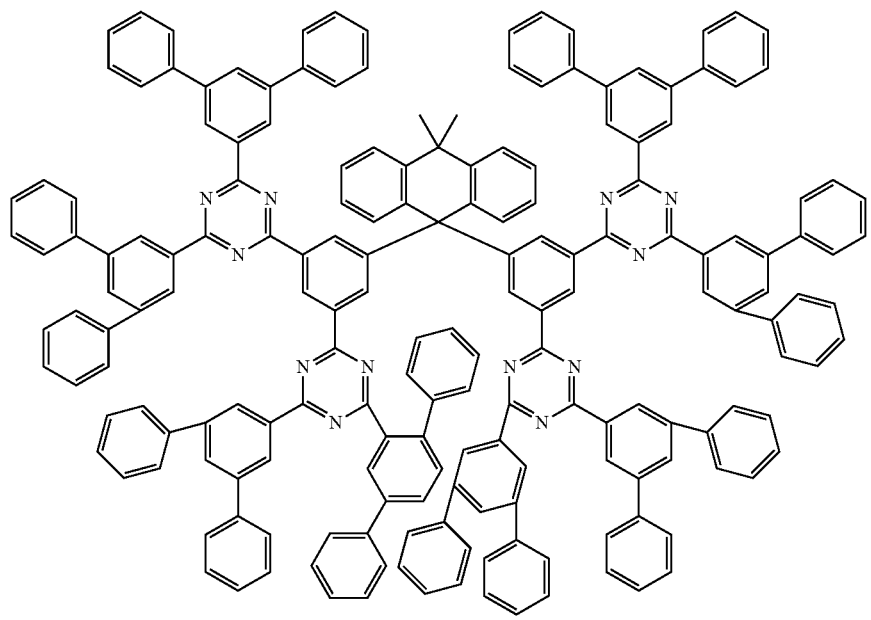

(65)
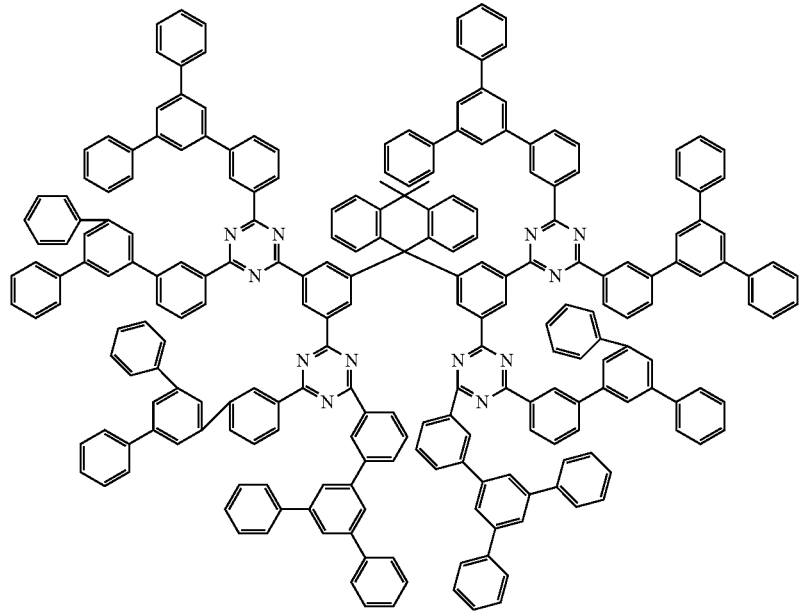
(66)
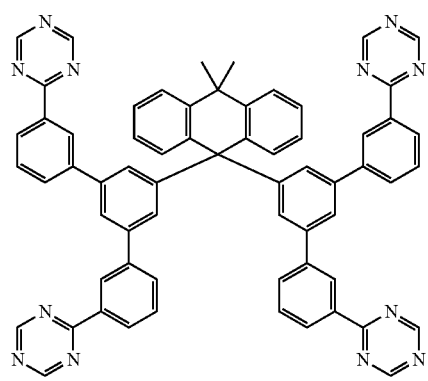
(67)
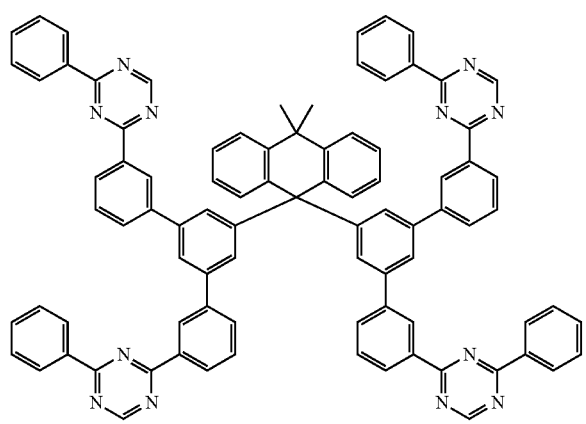
(68)
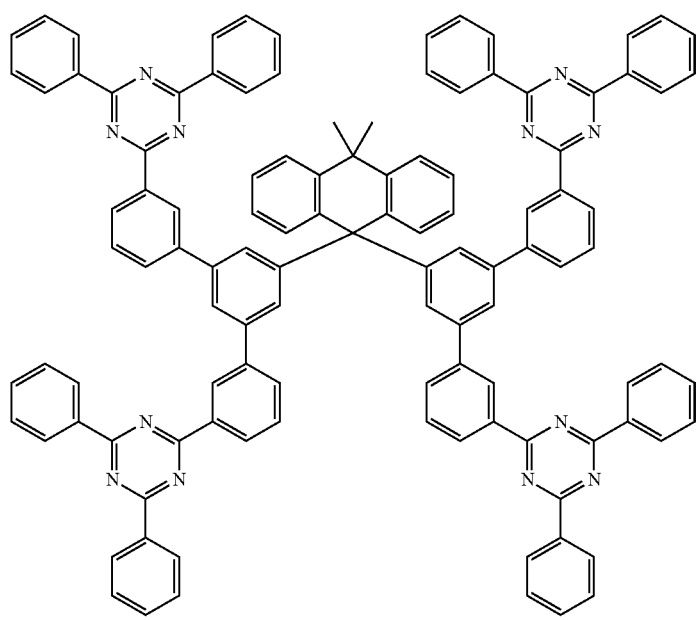

-continued
(69)
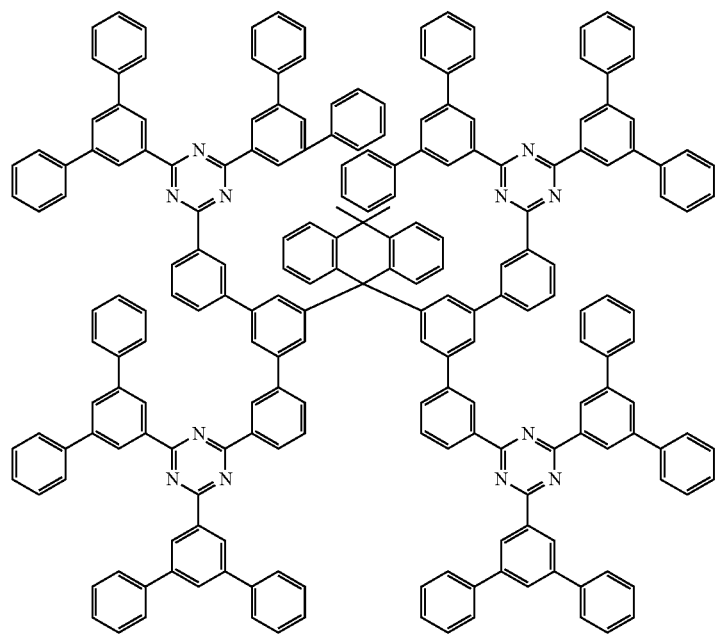
(70)
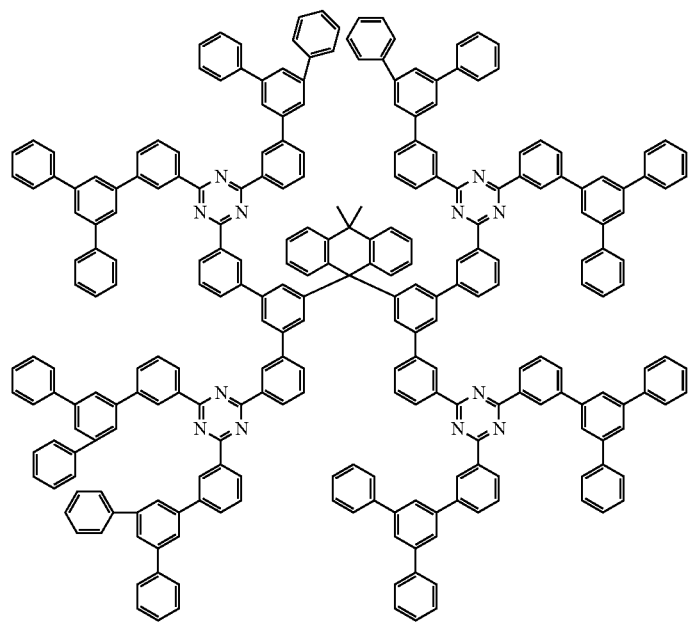
(71)
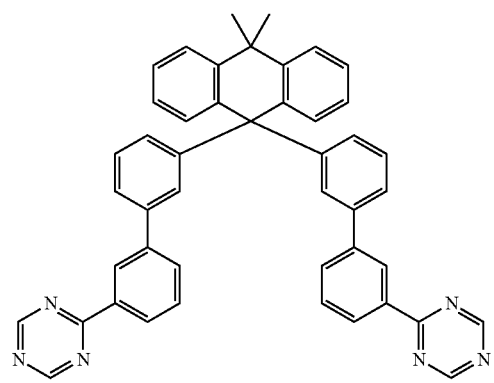
(72)
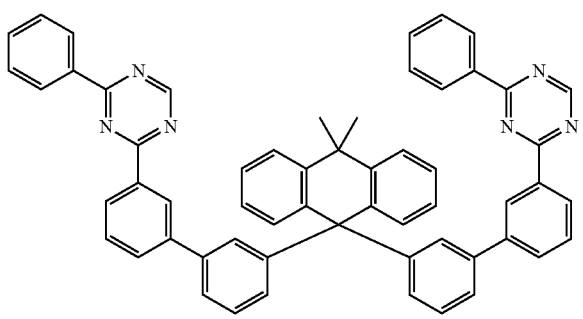

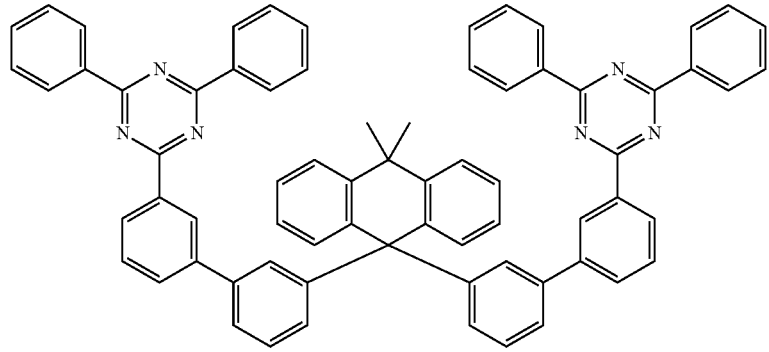
(73)
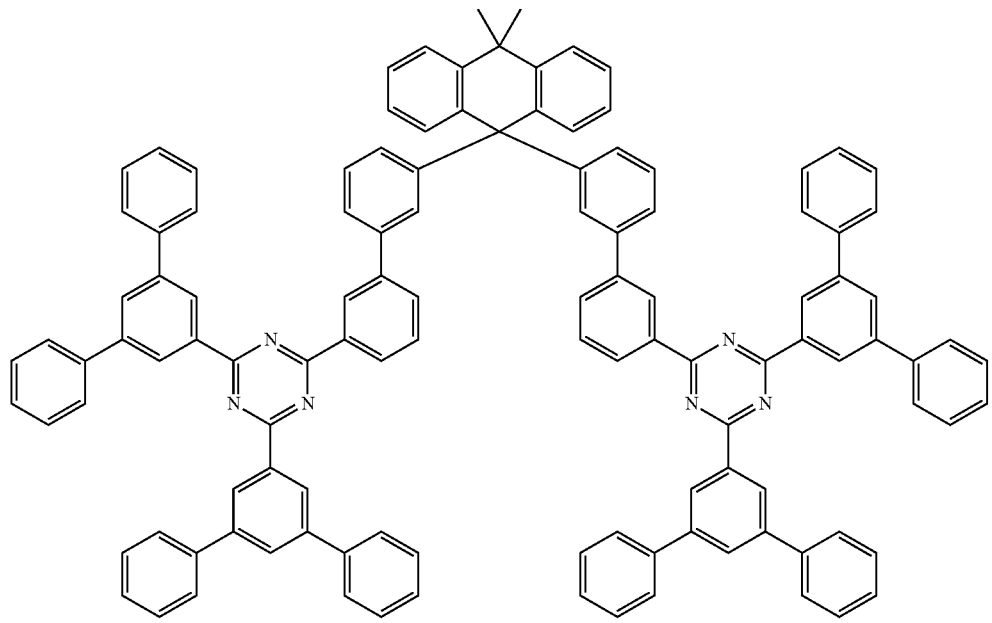
(74)
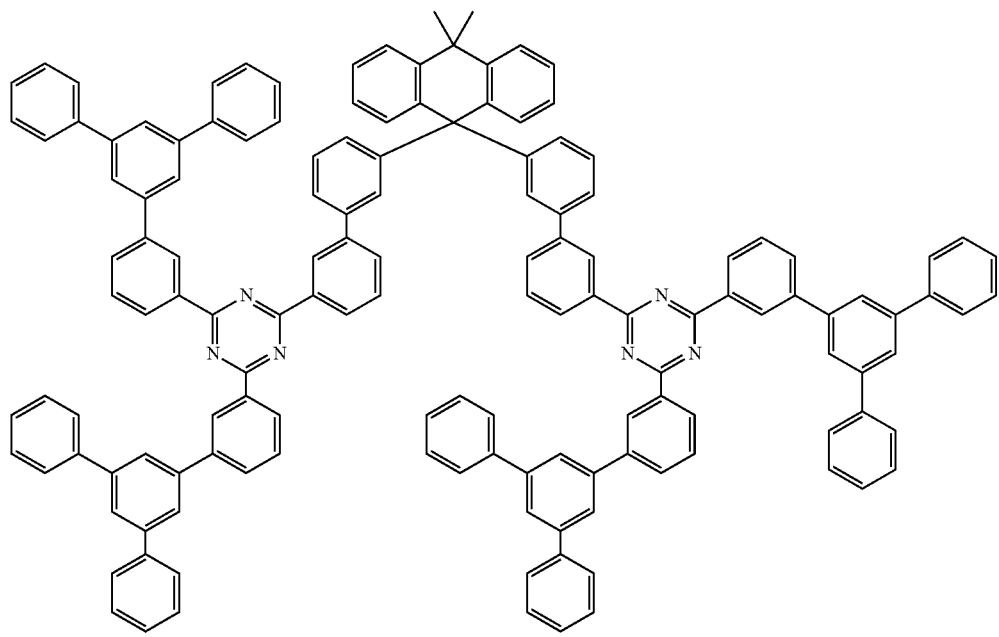
(75)

-continued
(76)
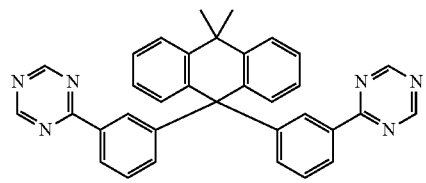
(77)
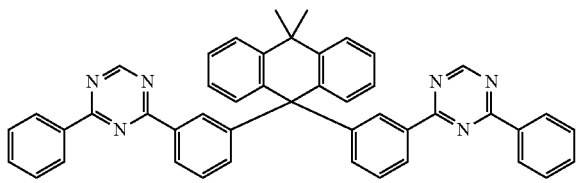
(78)
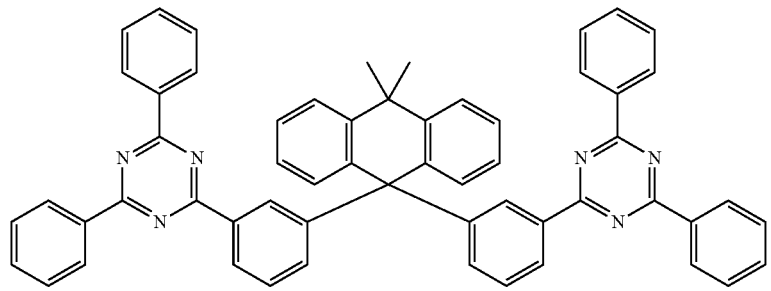
(79)
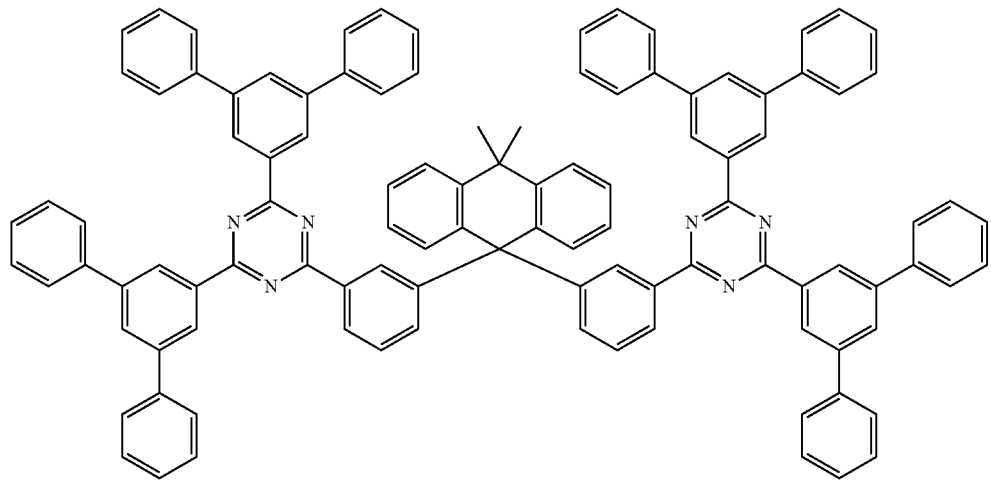
(80)
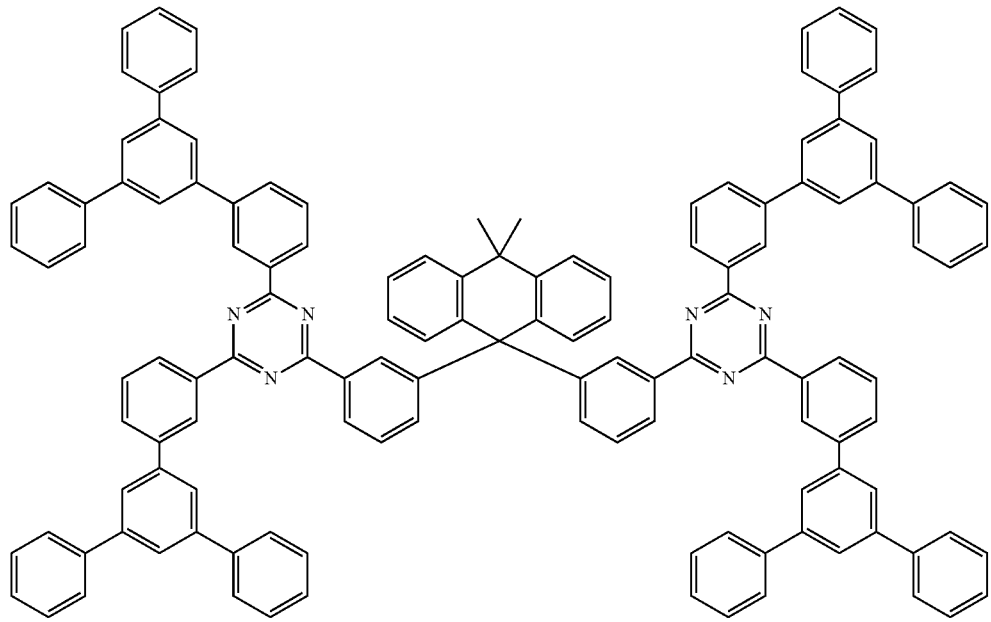

-continued
(81)
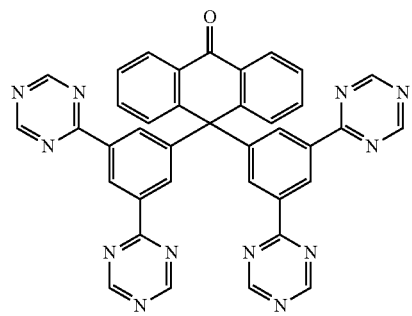
(82)
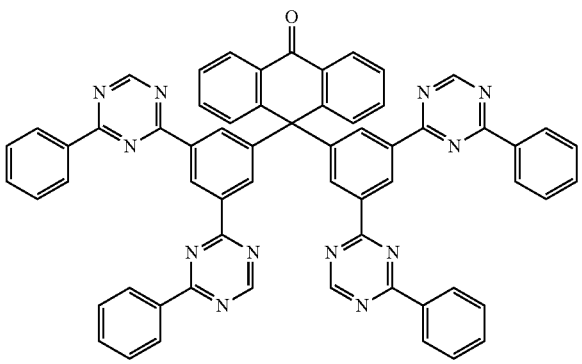
(83)
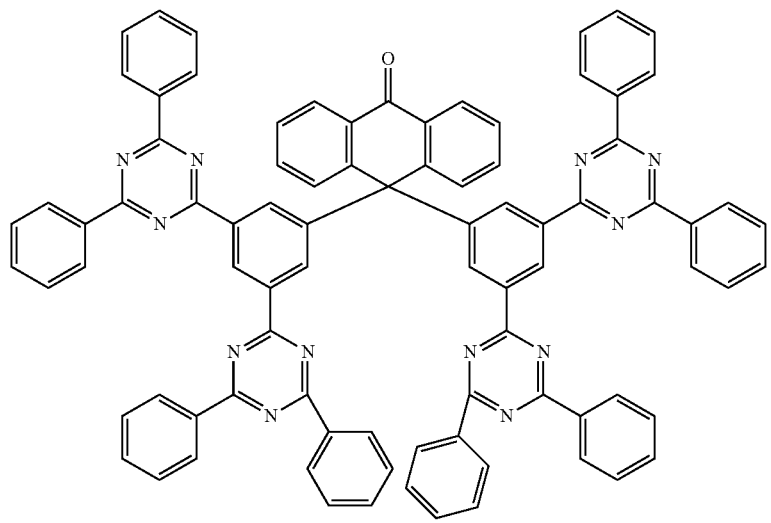
(84)
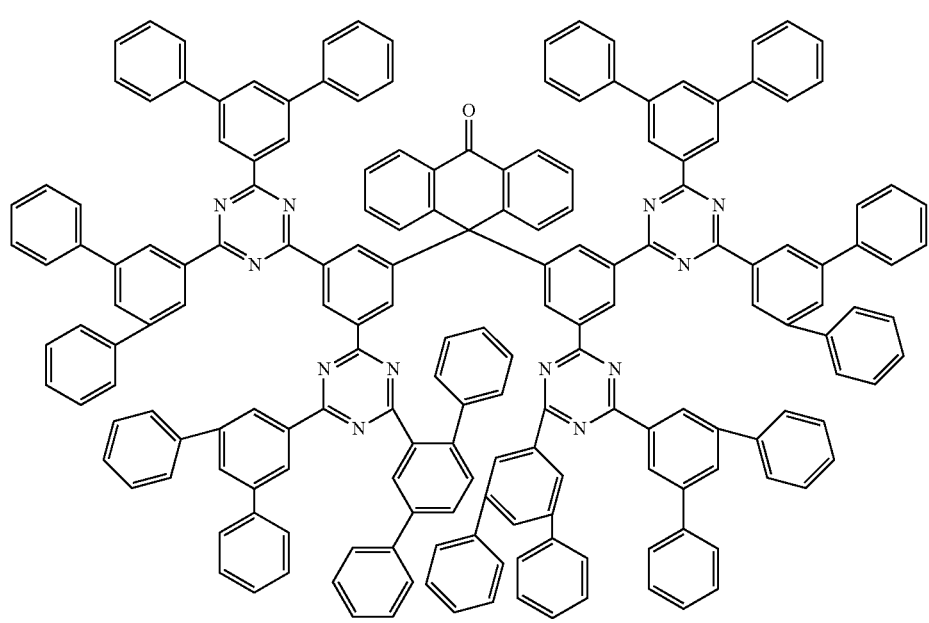

(85)
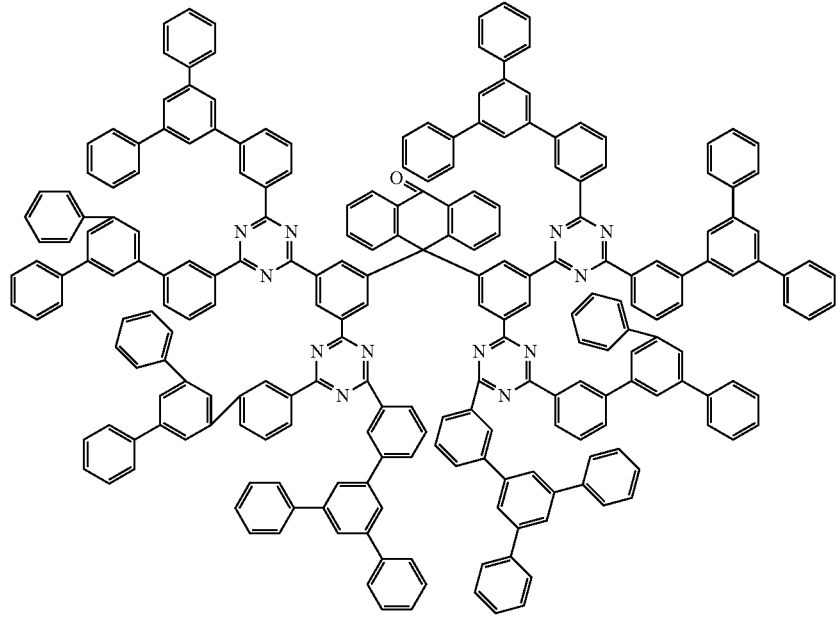
(86)
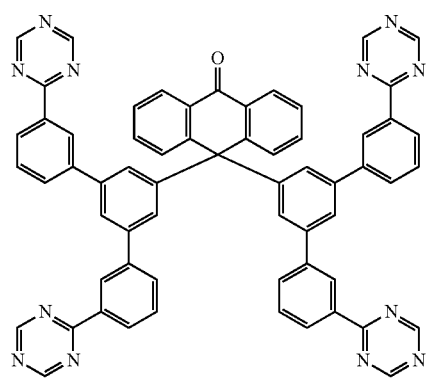
(87)
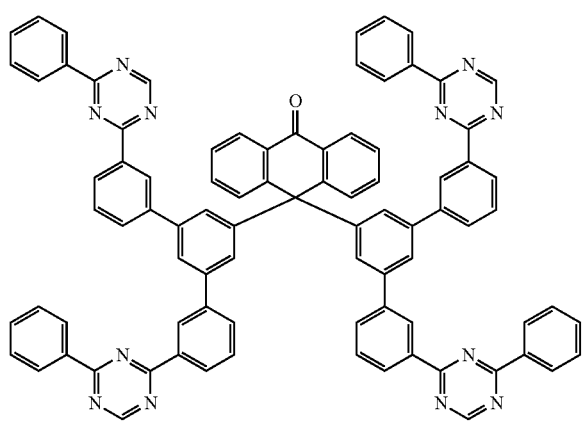

(88)
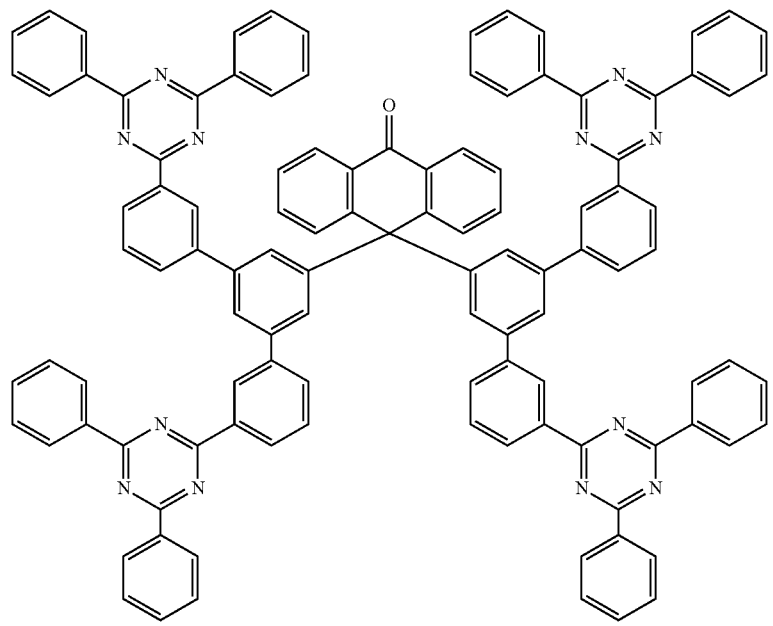
(89)
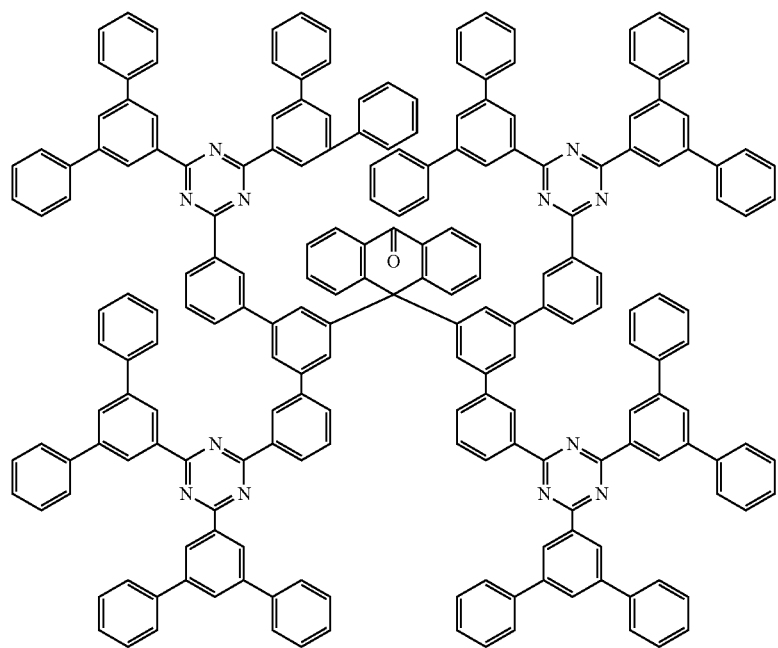

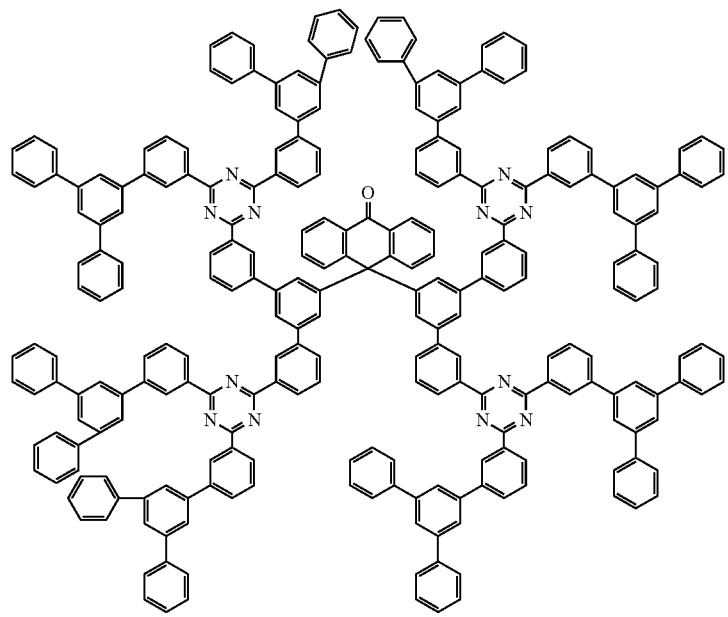
(90)
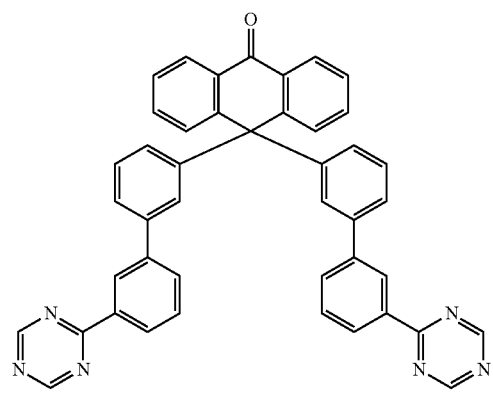
(91)
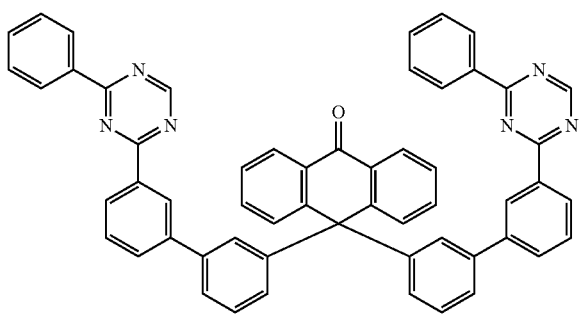
(92)
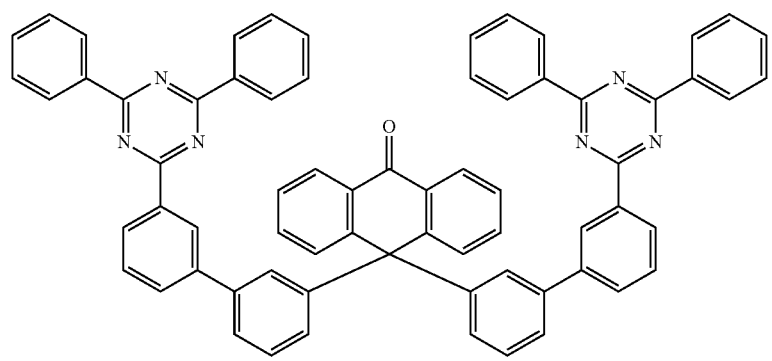
(93)

(94)
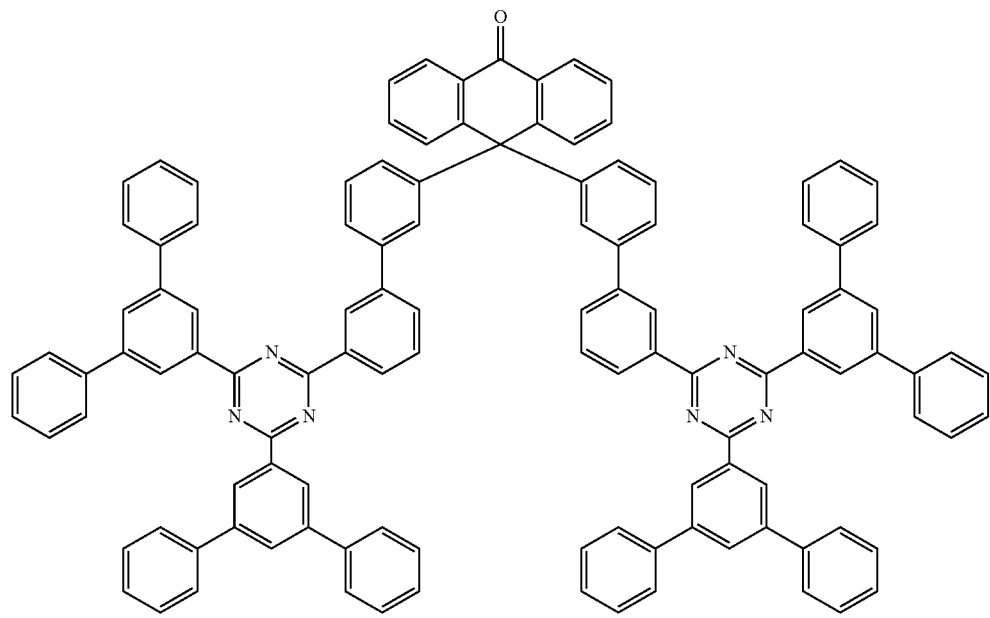
(95)
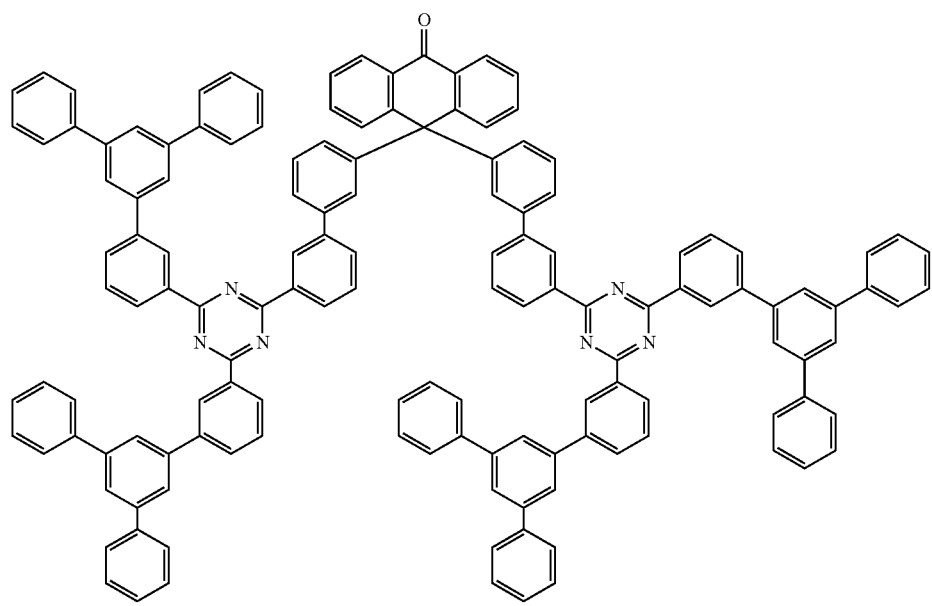
(96)
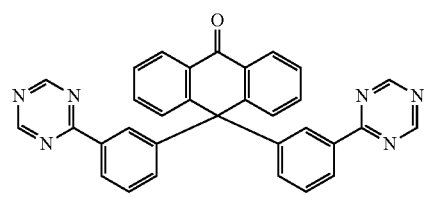
(97)
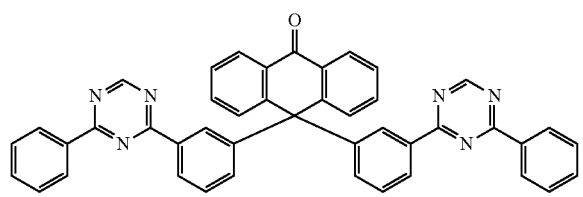

-continued
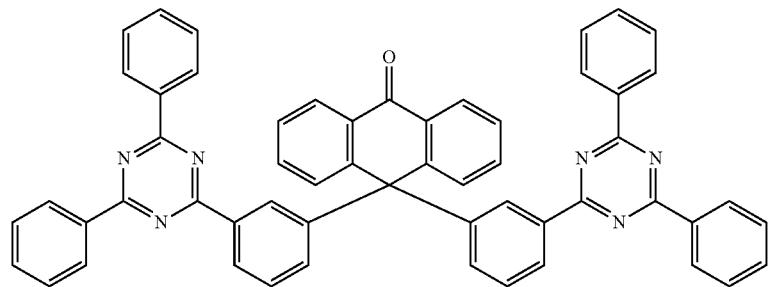
(98)
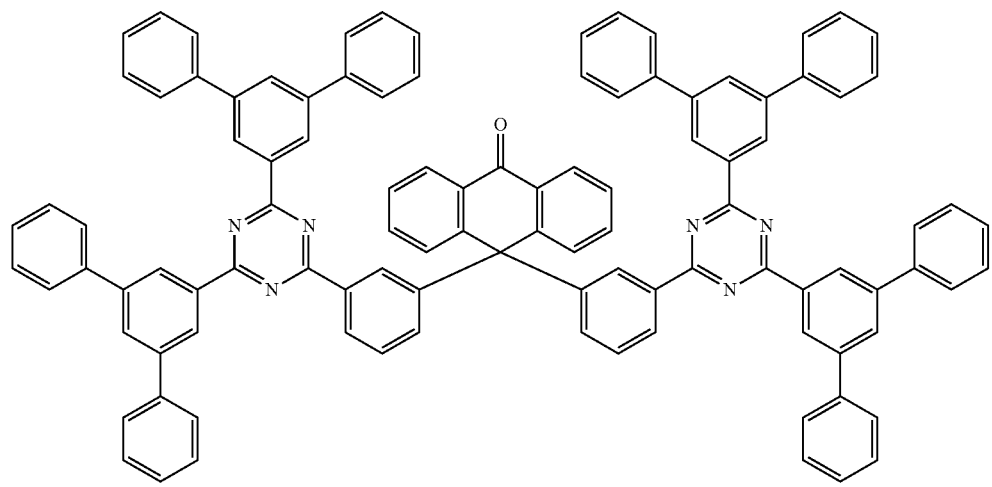
(99)
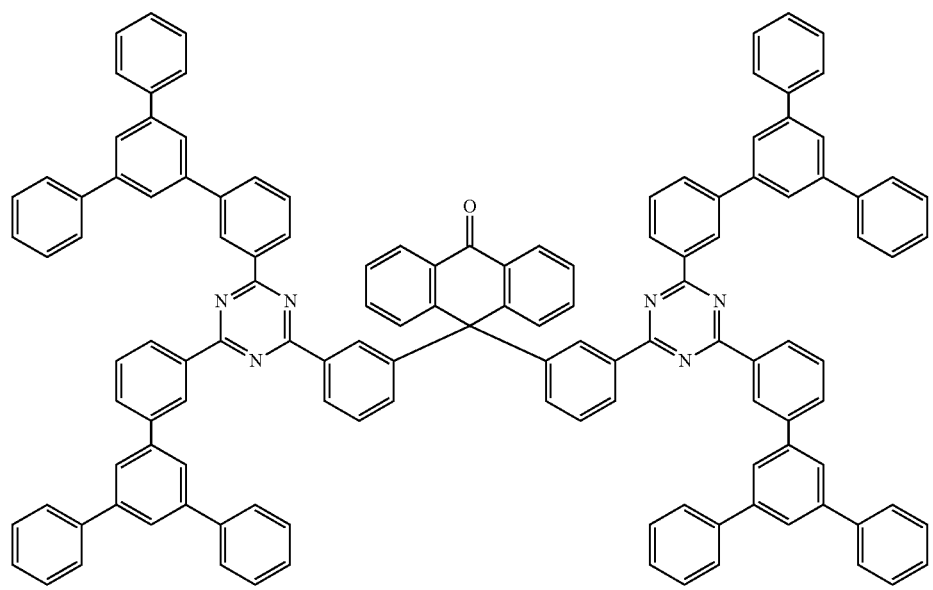
(100)

-continued
(101)
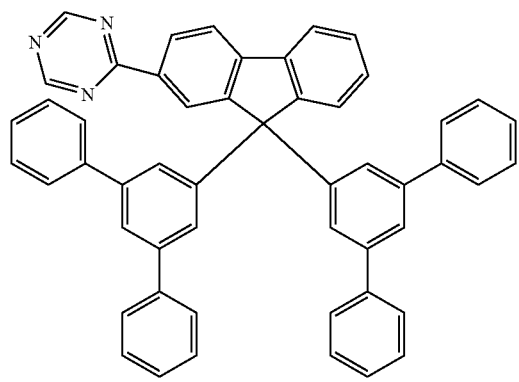
(102)
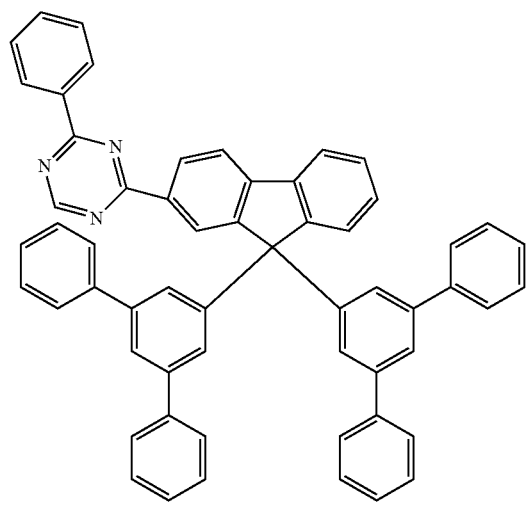
(103)
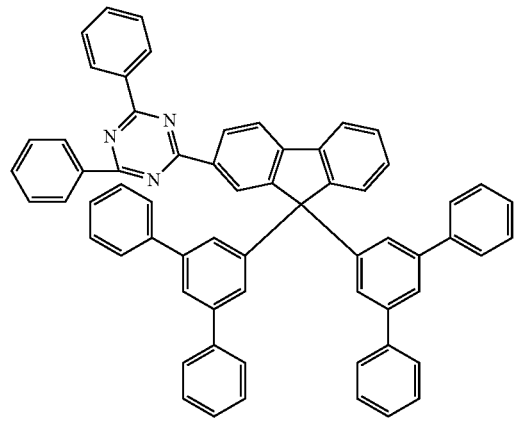
(104)
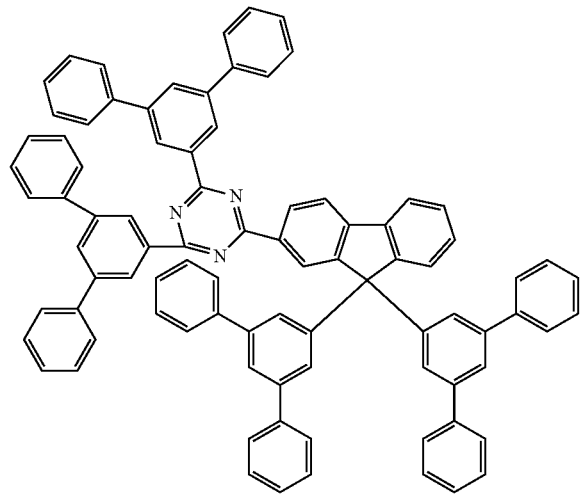
(105)
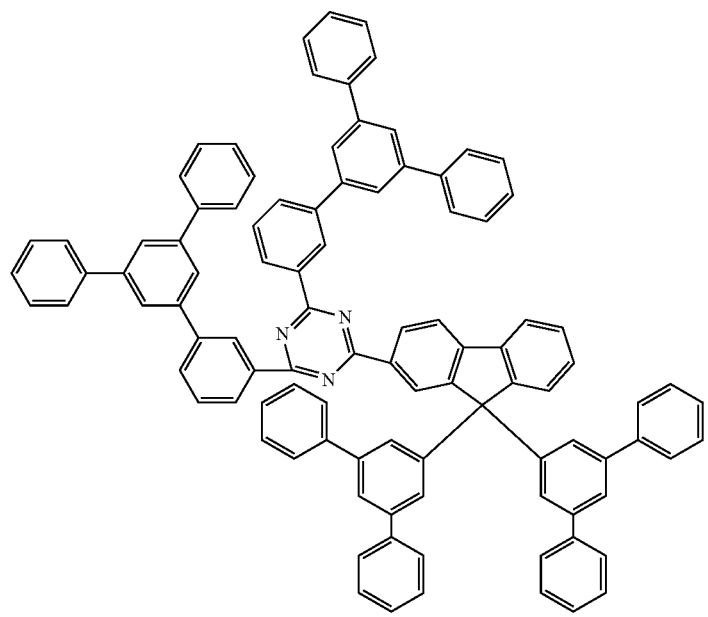

-continued
(106)
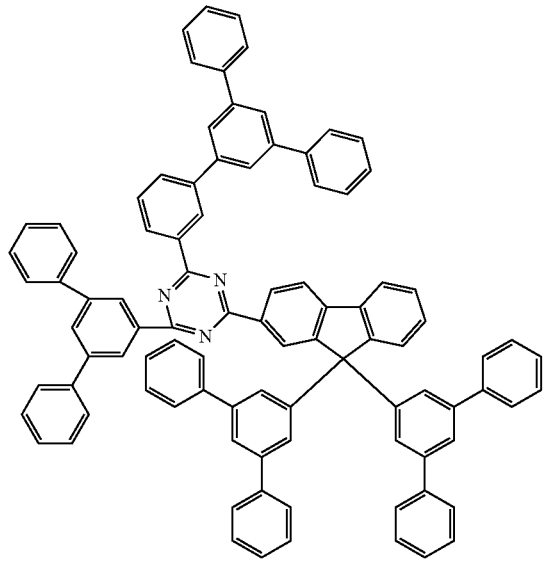
(107)
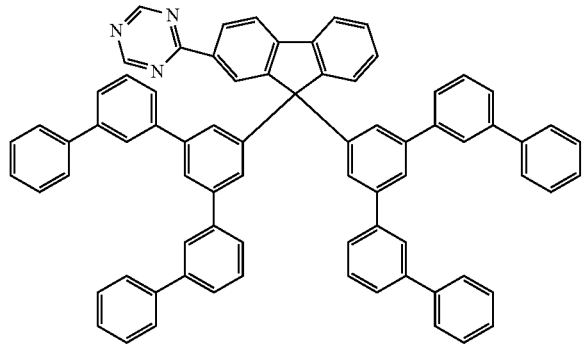
(108)
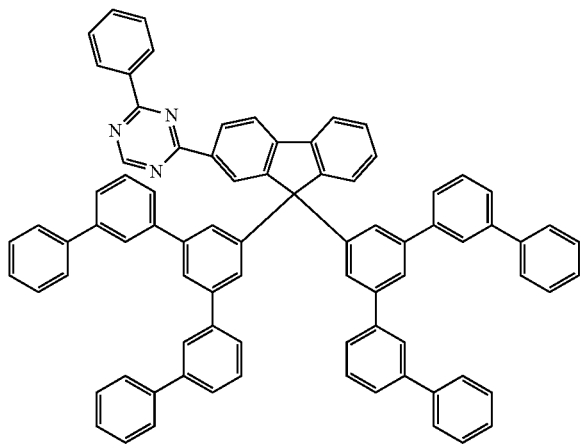
(109)
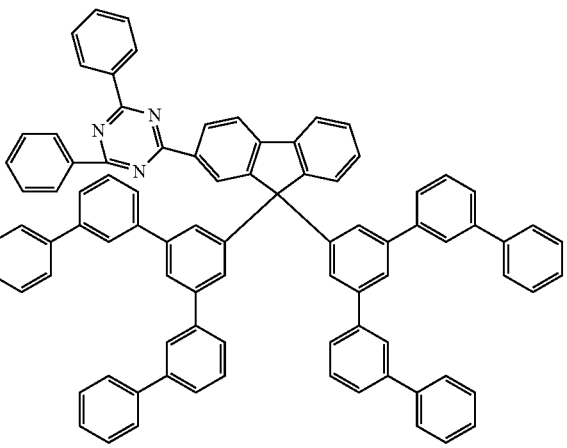
(110)
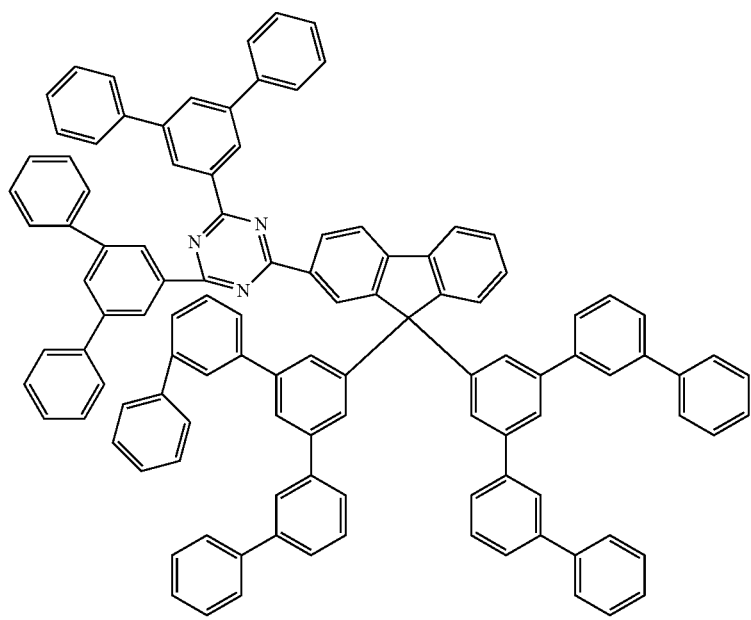

(111)
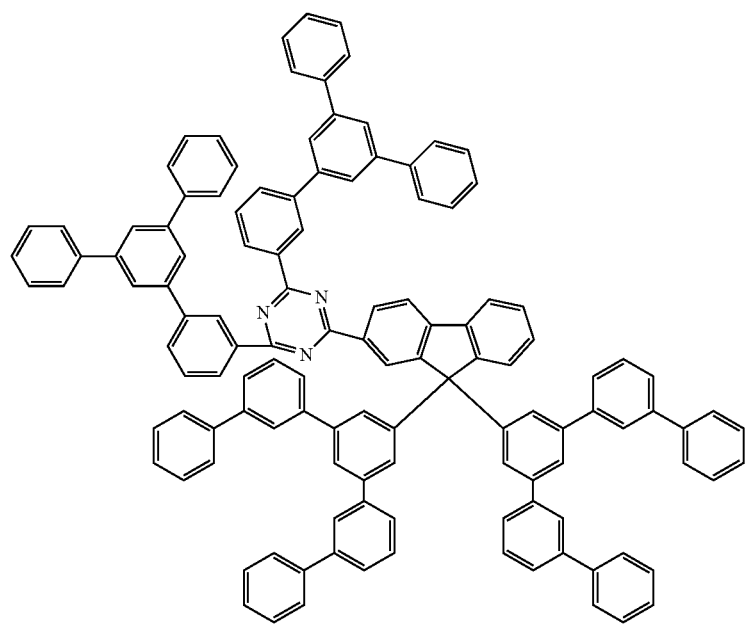
(112)
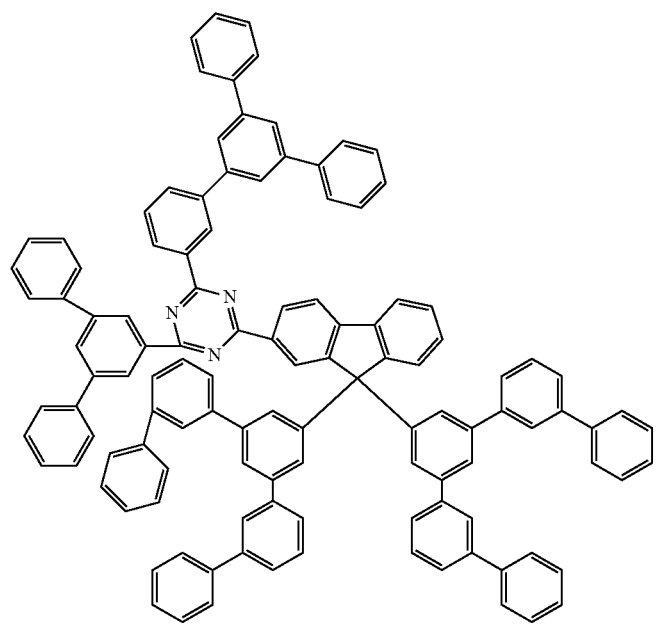

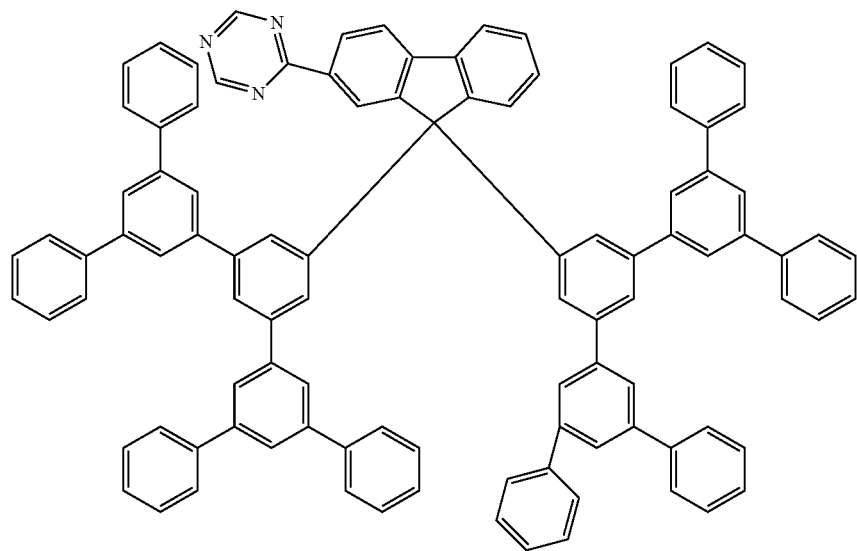
(113)
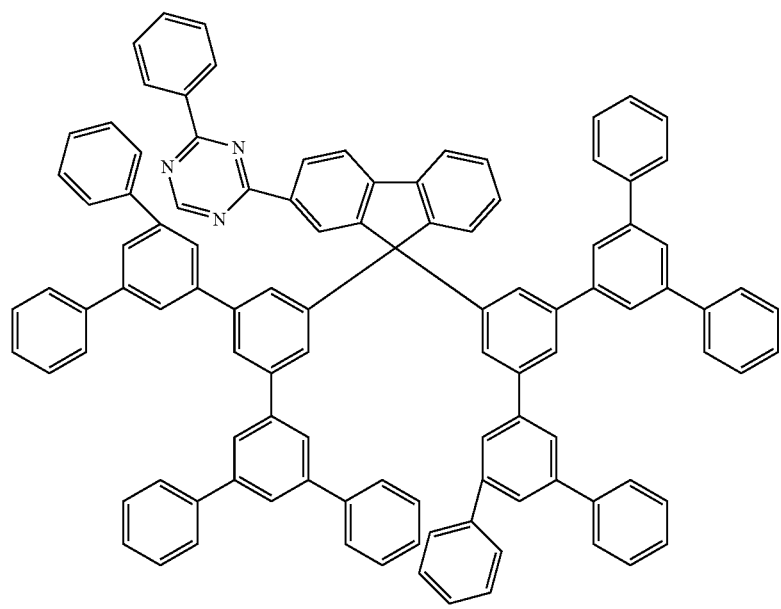
(114)

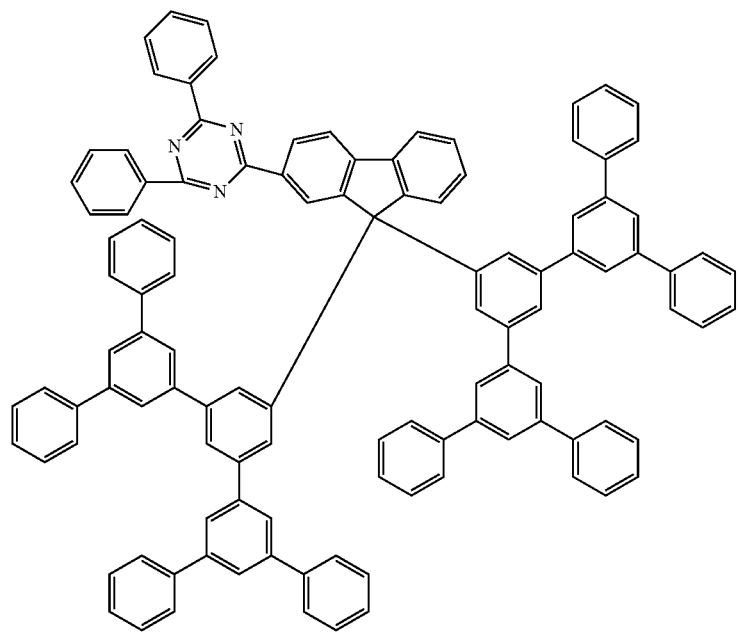
(115)
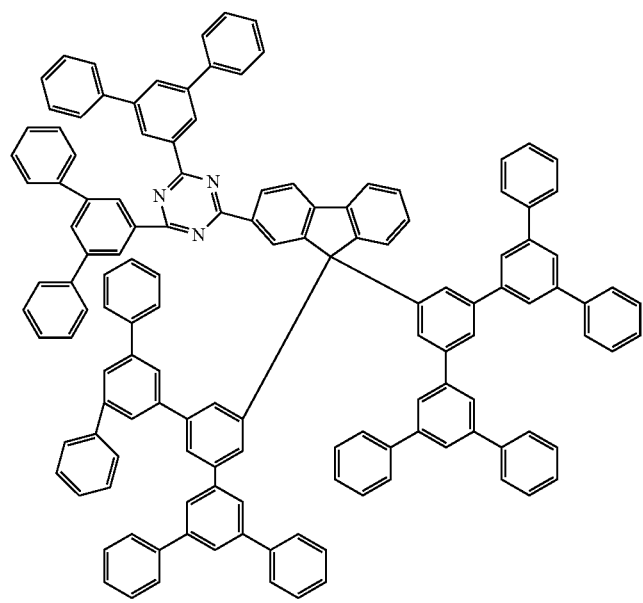
(116)

(117)
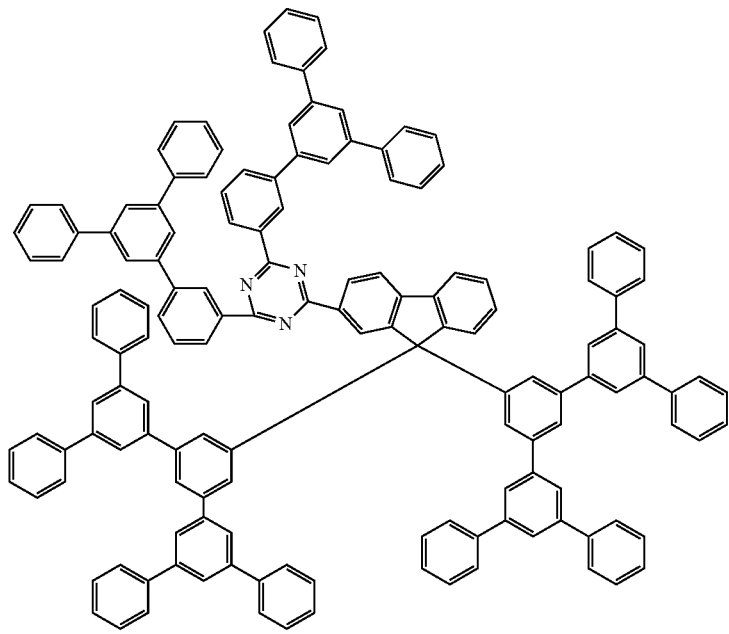
(118)
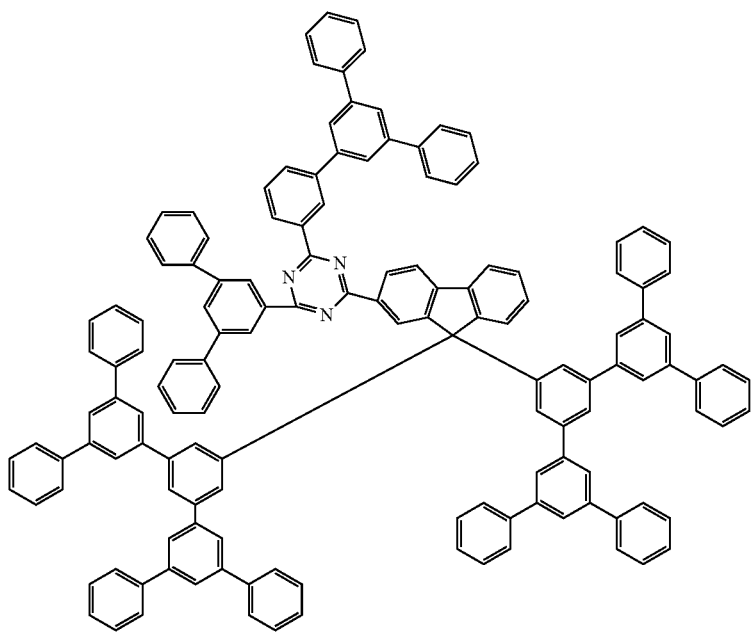

(119)
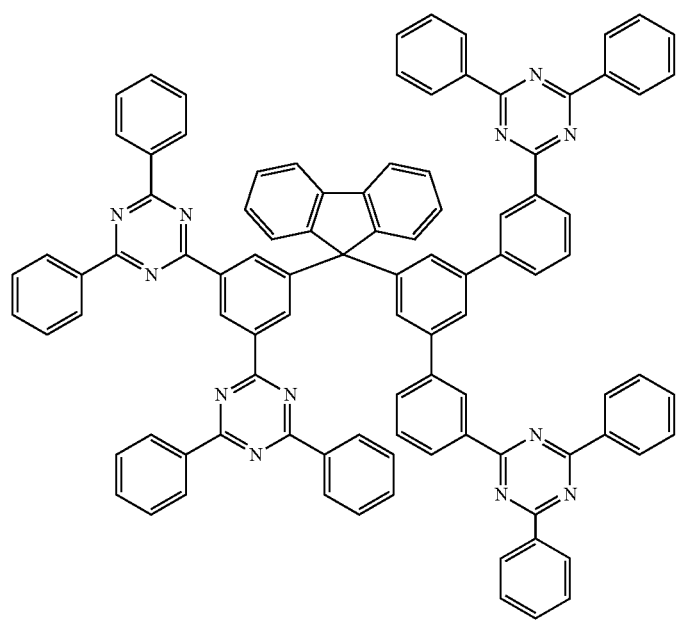
(120)
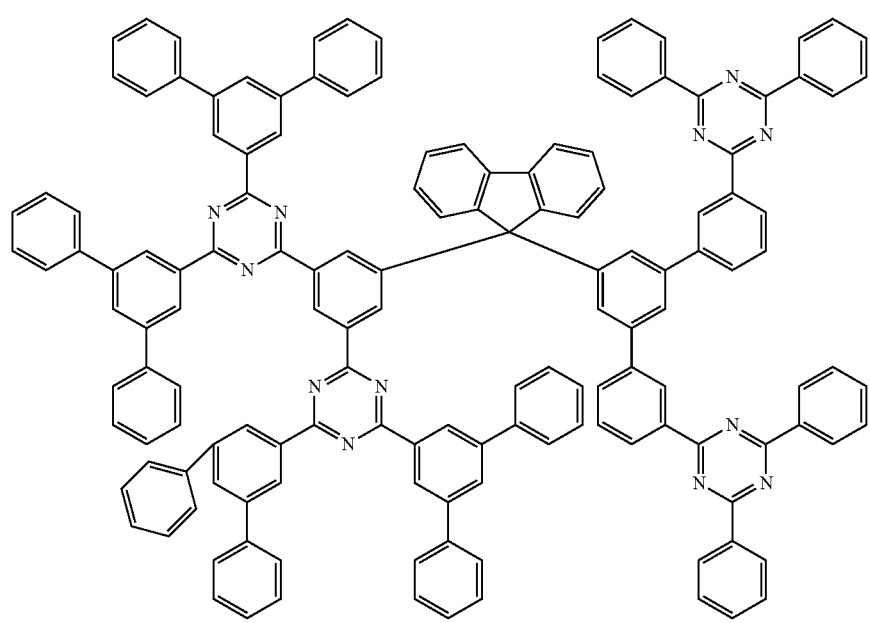

(121)

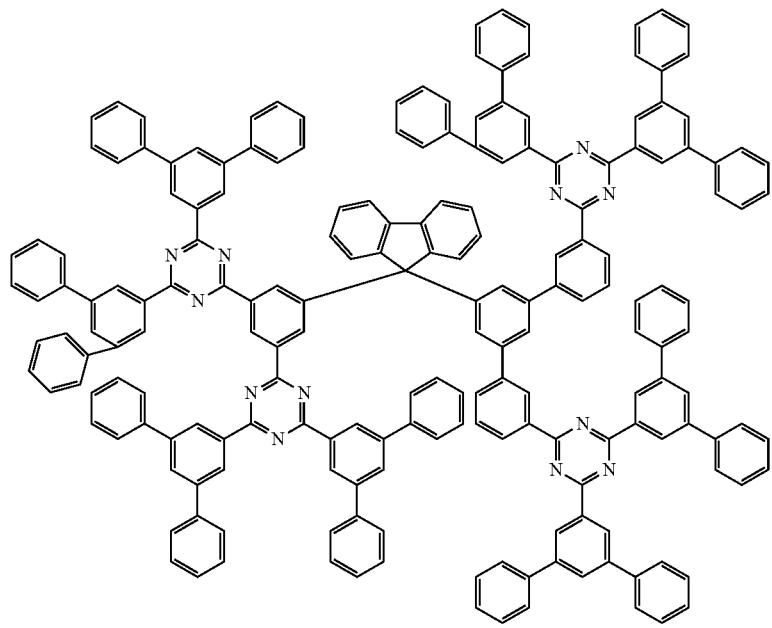

(122)

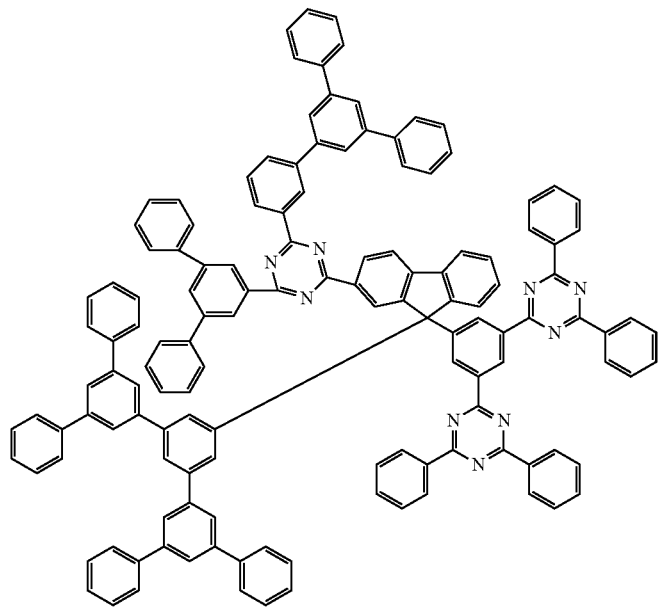

The compounds of the formula (1) according to the invention can be prepared by synthesis steps which are generally known to the person skilled in the art. The starting compound used for symmetrically substituted compounds according to the invention can be, for example, 3,3',5,5'-tetrabromobenzophenone (*Eur. J. Org. Chem.* 2006, 2523-2529). This can be reacted, for example, in accordance with Scheme 1 with a substituted or unsubstituted 2-lithiobiphenyl, 2-lithiodiphenyl ether, 2-lithiodiphenyl thioether, 2-(2-lithiophenyl)-2-phenyl-1,3-dioxolane or 2-lithiophenyldiphenylamine to give the corresponding triarylmethanols, which are then cyclised under acidic conditions, for example in the presence of acetic acid and a mineral acid, such as hydrogen bromide. The organolithium compounds required for this reaction can be prepared by transmetallation of the corresponding aryl bromides (2-bromobiphenyl, 2-bromodiphenyl ether, 2-bromodiphenyl thioether, 2-(2-bromophenyl)-2-phenyl-1,3-dioxolane, 2-bromophenyldiphenylamine, etc.) using alkyllithium compounds, such as n-butyllithium. Analogously, it is possible to employ the corresponding Grignard compounds.

Scheme 1

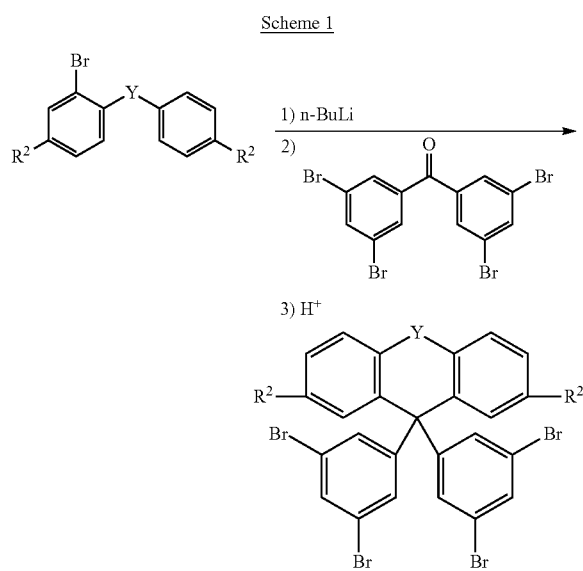

The tetrabromides produced in this way can be converted further by methods known to the person skilled in the art. Palladium-catalysed reaction with boronic acids (Suzuki coupling) or with organozinc compounds (Negishi coupling) results in aromatic or heteroaromatic compounds according to the invention (Scheme 2). At least one radical $R^2$ here contains a nitrogen-containing 6-membered heterocycle, or at least one Br is substituted by a group which contains a triazine group.

Scheme 2

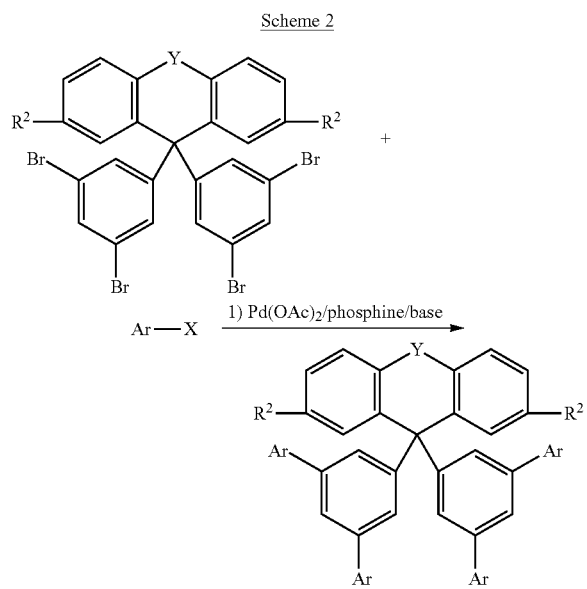

Ar = aromatic/heteroaromatic hydrocarbon
X = B(OH)₂, ZnBr, MgBr, etc.

The invention furthermore relates to a process for the preparation of the compounds of the formula (1), comprising the reaction of bis(3,5-dibromo)benzophenone with a substituted or unsubstituted 2-lithiobiphenyl, 2-lithiodiphenyl ether, 2-lithiodiphenyl thioether, 2-(2-lithiophenyl)-2-phenyl-1,3-dioxolane, 2-lithiophenyldiphenylamine or a corresponding Grignard compound to give a triarylmethanol, followed by cyclisation under acidic conditions and optionally followed by further reaction of the bromine groups. At least one radical $R^2$ here contains a nitrogen-containing 6-membered heterocycle, or at least one Br is substituted by a group which contains a triazine group.

The compounds according to the invention described above, in particular compounds which are substituted by reactive leaving groups, such as bromine, iodine, triflate, tosylate, boronic acid or boronic acid ester, can be used as monomers for the production of corresponding dimers, trimers, tetramers, pentamers, oligomers, polymers or as the core of dendrimers. The oligomerisation or polymerisation here preferably takes place via the halogen functionality or the boronic acid functionality. This applies, in particular, to compounds of the formulae (2) to (15) in which at least one radical $R^1$ or $R^2$, preferably two radicals $R^1$ and/or $R^2$, each stand(s) for a reactive leaving group, in particular selected from the groups mentioned above.

The invention therefore furthermore relates to dimers, trimers, tetramers, pentamers, oligomers, polymers or dendrimers comprising one or more compounds of the formula (1), where one or more radicals $R^1$ or $R^2$ or one or more H atoms of the compound of the formula (1) represent bonds between the compounds of the formula (1) in the dimer, trimer, tetramer or pentamer or bonds from the compound of the formula (1) to the polymer, oligomer or dendrimer.

An oligomer in the sense of this invention is taken to mean a compound which has at least six units of the formula (1). A polymer in the sense of this invention is taken to mean a compound which has at least about 10 units of the formula (1). The polymers, oligomers or dendrimers may be conjugated, partially conjugated or non-conjugated. The trimers, tetramers, pentamers, oligomers or polymers may be linear or branched. In the linearly linked structures, the units of the formula (1) can be linked directly to one another or linked to one another via a divalent group, for example via a substituted or unsubstituted alkylene group, via a heteroatom or via a divalent aromatic or heteroaromatic group. In branched structures, for example, three or more units of the formula (1) may be linked via a trivalent or polyvalent group, for example via a trivalent or polyvalent aromatic or heteroaromatic group, to give a branched trimer, tetramer, pentamer, oligomer or polymer.

For the recurring units of the formula (1) in dimers, trimers, tetramers, pentamers, oligomers and polymers, the same preferences apply as described above. Preferred recurring units are therefore again the units of the formulae given above.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The polymers, oligomers and dendrimers usually also contain further units, for example emitting (fluorescent or phosphorescent) units, such as, for example, vinyltriarylamines (for example in accordance with WO 07/068325) or phosphorescent metal complexes (for example in accordance with WO 06/003000), and/or charge-transport units. The recurring units according to the invention are particularly suitable as charge-transport units for electrons.

The present invention furthermore relates to mixtures comprising at least one compound of the formula (1) or a corresponding dimer, trimer, tetramer, pentamer, oligomer or polymer and at least one further compound. The further compound can be, for example, a fluorescent or phosphorescent dopant if the compound of the formula (1) is used as matrix material. Suitable fluorescent and phosphorescent dopants are mentioned below in connection with the organic electroluminescent devices and are also preferred for the mixtures according to the invention. The further compound can also be a dopant if the compound of the formula (1) is a hole-transport or electron-transport compound. Suitable dopants are mentioned below in connection with the organic electroluminescent devices.

For processing from solution or the liquid phase, for example by spin coating or by printing processes, solutions or formulations of the compounds of the formula (1) are necessary. It may also be preferred to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation comprising at least one compound of the formula (1) and one or more solvents, in particular organic solvents. These are preferably solutions, suspensions or mini emulsions, in particular solutions. The way in which solutions of this type can be prepared is known to the person skilled in the art and is described, for example, in WO 02/072714, WO 03/019694 and the literature cited therein.

The compounds of the formula (1) according to the invention and corresponding dimers, trimers, tetramers, pentamers, oligomers, polymers or dendrimers are suitable for use in electronic devices, in particular in organic electroluminescent devices (OLEDs, PLEDs). Depending on the substitution, the compounds are employed in different functions and layers. The preferred embodiments here conform to the formulae given above.

The invention therefore furthermore relates to the use of compounds of the formula (1) or corresponding dimers, trimers, tetramers, pentamers, oligomers, polymers or dendrimers in electronic devices, in particular in organic electroluminescent devices.

The invention still furthermore relates to electronic devices comprising at least one compound of the formula (1) or a corresponding dimer, trimer, tetramer, pentamer, oligomer, polymer or dendrimer. The electronic device here is preferably selected from the group consisting of organic electroluminescent devices (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

Particular preference is given to organic electroluminescent devices comprising an anode, a cathode and at least one emitting layer, characterised in that at least one organic layer, which may be an emitting layer or another layer, comprises at least one compound of the formula (1) or a corresponding dimer, trimer, tetramer, pentamer, oligomer, polymer or dendrimer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Mg/Ag, Ca/Ag or Ba/Ag, are generally used. Preference is likewise given to metal alloys, in particular alloys comprising an alkali metal or alkaline-earth metal and silver, particularly preferably an alloy of Mg and Ag. It may also be preferred to introduce a thin interlayer of a material having a high dielectric constant between a metallic cathode and the organic semiconductor. Suitable for this purpose are, for example, alkali-metal or alkaline-earth metal fluorides, but also the corresponding oxides or carbonates (for example LiF, $Li_2O$, CsF, $Cs_2CO_3$, $BaF_2$, MgO, NaF, etc.). Organic metal compounds, such as, for example, lithium quinolinate, can also be used. The layer thickness of this layer is preferably between 0.5 and 5 nm.

The anode preferably comprises materials having a high work function.

The anode preferably has a work function of greater than 4.5 eV against vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to enable either the irradiation of the organic material (O-SCs) or the coupling-out of light (OLEDs/PLEDs, O-lasers). Preferred anode materials for transparent or partially transparent anodes are conductive mixed metal oxides. Particular preference is given to indium tin oxide (ITO) or indium zinc oxide (IZO). Preference is furthermore given to conductive, doped organic materials, in particular conductive, doped polymers, for example PEDOT or PANI.

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers and/or organic or inorganic p/n junctions. Furthermore, the layers, in particular the charge-transport layers, may also be doped. The doping of the layers may be advantageous for improved charge transport. However, it should be pointed out that each of these layers does not necessarily have to be present, and the choice of layers is always dependent on the compounds used and in particular also on whether the electroluminescent device is fluorescent or phosphorescent.

In a further preferred embodiment of the invention, the organic electroluminescent device comprises a plurality of emitting layers, where at least one organic layer comprises at least one compound of the formula (1). These emission layers particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where at least one of these layers comprises at least one compound of the formula (1) and where the three layers exhibit blue, green and orange or red emission (for the basic structure, see, for example, WO 05/011013). Emitters which have broad-band emission bands and thus exhibit white emission are likewise suitable for white emission. For white-emitting electroluminescent devices, it is likewise preferred for one or more emitting layers to be phosphorescent and one or more emitting layers to be fluorescent.

In a preferred embodiment of the invention, the compounds of the formula (1) are employed as matrix material for fluorescent or phosphorescent compounds in an emitting layer, in particular as matrix material for phosphorescent compounds.

A matrix material in a system comprising matrix and dopant is taken to mean the component which is present in the higher proportion in the system. In a system comprising a matrix and a plurality of dopants, the matrix is taken to mean the component whose proportion in the mixture is the highest.

In an embodiment, the compound of the formula (1) is employed as the only matrix material in the mixture with the emitter. In a further embodiment of the invention, the compound of the formula (1) is employed as a mixture together with a further matrix material and an emitter. Preferably, one component of this mixture of matrix materials is a hole-transport compound and the other is an electron-transport compound of the formula (1).

Suitable materials with which the compound of the formula (1) can be employed as a mixture are selected from the group consisting of aromatic ketones, aromatic phosphine oxides or aromatic sulfoxides or sulfones, for example in accordance with WO 04/013080, WO 04/093207, WO 06/005627 or WO 2010/006680, triarylamines, carbazole derivatives, for example CBP (N,N-biscarbazolylbiphenyl), mCBP or the carbazole derivatives disclosed in WO 05/03924, US 2005/0069729, JP 2004/288381, EP 1205527 or WO 08/086851, indolocarbazole derivatives, for example in accordance with WO 07/063754 or WO 08/056746, indenocarbazole derivatives, for example in accordance with the unpublished applications DE 102009023155.2 or DE 102009031021 0.5, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with WO 2010/015306, WO 07/063754 or WO 08/056746, zinc complexes, for example in accordance with EP 652273 or WO 09/062578, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779 or the unpublished application DE 102009048791.3. A further phosphorescent emitter which emits at shorter wavelength than the actual emitter may likewise be present in the mixture as co-host. It is furthermore possible to use mixtures of two or more compounds of the formula (1) as matrix materials.

If the compound of the formula (1) is employed as matrix material for an emitting compound in an emitting layer, it can be employed in combination with one or more phosphorescent materials (triplet emitters). Phosphorescence in the sense of this invention is taken to mean the luminescence from an excited state of relatively high spin multiplicity, i.e. a spin state >1, in particular from an excited triplet state. For the purposes of this invention, all luminescent transition-metal complexes and all luminescent lanthanide complexes, in particular luminescent iridium, platinum, osmium, gold and copper compounds, are referred to as phosphorescent materials. The mixture of the compound of the formula (1) and the emitting compound then comprises between 99 and 1% by weight, preferably between 98 and 10% by weight, particularly preferably between 97 and 60% by weight, in particular between 95 and 75% by weight, of the compound of the formula (1), based on the entire mixture of emitter and matrix material. Correspondingly, the mixture comprises between 1 and 99% by weight, preferably between 2 and 90% by weight, particularly preferably between 3 and 40% by weight, in particular between 5 and 25% by weight, of the emitter, based on the entire mixture of emitter and matrix material.

Suitable phosphorescent compounds (=triplet emitters) are, in particular, compounds which emit light, preferably in the visible region, on suitable excitation and in addition contain at least one atom having an atomic number of greater than 20, preferably greater than 38 and less than 84, particularly preferably greater than 56 and less than 80. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373, US 2005/0258742, WO 09/146770, WO 10/015307, WO 10/031485, WO 10/054731 and WO 10/054728. Furthermore suitable are the complexes in accordance with the unpublished applications DE 102009007038.9, DE 102009011223.5 and DE 102009013041.1. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

If the compound of the formula (1) is employed as matrix material for fluorescent compounds, the proportion of the matrix material in the emitting layer is between 50.0 and 99.9% by weight, preferably between 80.0 and 99.5% by weight, particularly preferably between 90.0 and 99.0% by weight. Correspondingly, the proportion of the dopant is between 0.1 and 50.0% by weight, preferably between 0.1 and 20.0% by weight, particularly preferably between 0.5 and 15% by weight, very particularly preferably between 1.0 and 10.0% by weight.

Preferred dopants are selected from the class of the monostyrylamines, the distyrlamines, the trstrylamines, the tetrastyrlamines, the styrylphosphines, the styryl ethers and the arylamines. A monostyramine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styrl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups on the pyrene are preferably bonded in the 1-position or in the 1,6-position. Further preferred dopants are selected from indenofluorenamines or indenofluorenediamines, for example in accordance with WO 06/122630, benzoindenofluorenamines or benzoindenofluorenediamines, for example in accordance with WO 08/006449, and dibenzoindenofluorenamines or dibenzoindenofluorenediamines, for example in accordance with WO 07/140847. Examples of dopants from the class of the styrylamines are substituted or unsubstituted tistilbenamines or the dopants described in WO 06/000388, WO 06/058737, WO 06/000389, WO 07/065549 and WO 07/115610. Further suitable fluorescent dopants are the condensed aromatic hydrocarbons disclosed in WO 2010/012328.

In still a further embodiment of the invention, the compounds of the formula (1) are employed as electron-transport material or as hole-blocking material in an electron-transport layer or hole-blocking layer. Due to the presence of the electron-deficient heteroaromatic groups $R^1$ and/or $R^2$, these compounds have very good electron-transport properties. It may furthermore be preferred for the compound to be doped with electron-donor compounds. A hole-blocking layer in the sense of this invention is a layer which is located between an emitting layer and an electron-transport layer and is directly adjacent to the emitting layer. If the compound of the formula (1) is employed as electron-transport material, it may be preferred to employ this as a mixture with a further compound. Preferred mixture components are alkali-metal compounds, preferably lithium compounds, particularly preferably Liq (lithium quinolinate) or Liq derivatives.

In a further embodiment of the invention, the compounds of the formula (1) are employed as hole-transport material or as hole-injection material or as electron-blocking material or as exciton-blocking material. Preferred groups which improve hole transport are, for example, the groups $N(R^1)$, S or O, in particular $N(R^1)$, as bridge Y or electron-rich heteroaromatic groups, in particular thiophene, pyrrole or furan, as group $R^1$. The compound is preferably employed in a hole-transport or hole-injection or electron-blocking or exciton-blocking layer. A hole-injection layer in the sense of this invention is a layer which is directly adjacent to the anode. A hole-transport layer in the sense of this invention is a layer which is located between a hole-injection layer and an emission layer. An electron-blocking or exciton-blocking layer in the sense of this invention is a layer which is directly adjacent to an emitting layer on the anode side. If the compounds of the formula (1) are used as hole-transport or hole-injection material, it may be preferred for them to be doped with electron-acceptor compounds, for example with $F_4$-TCNQ Or with compounds as described in EP 1476881 or EP 1596445.

Recurring units of the formula (1) can also be employed in polymers, either as polymer backbone, as hole-transporting unit and/or as electron-transporting unit. The preferred substitution patterns here correspond to those described above.

Preference is furthermore given to an organic electroluminescent device, characterised in that one or more layers are applied by means of a sublimation process, in which the materials are vapour-deposited in vacuum sublimation units at a pressure of less than $10^{-5}$ mbar, preferably less than $10^{-6}$ mbar. However, it should be noted that the pressure may also be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, LITI (light induced thermal imaging, thermal transfer printing, ink-jet printing, screen printing, flexographic printing, offset printing or nozzle printing. Soluble compounds are necessary for this purpose. High solubility can be achieved through suitable substitution of the compounds. It is possible here to apply not only solutions of individual materials, but also solutions which comprise a plurality of compounds, for example matrix material and dopant.

The organic electroluminescent device may also be produced as a hybrid system by applying one or more layers from solution and applying one or more other layers by vapour deposition. Thus, for example, it is possible to apply an emitting layer comprising a compound of the formula (1) and a phosphorescent dopant from solution and to apply a hole-blocking layer and/or an electron-transport layer on top by vacuum vapour deposition. The emitting layer comprising a compound of the formula (1) and a phosphorescent dopant can likewise be applied by vacuum vapour deposition, and one or more other layers can be applied from solution. Alternatively or additionally, it is, for example, also possible to apply an emitting layer from solution and to apply an electron-transport layer comprising a compound of the formula (1), optionally in combination with an organic alkali-metal compound, on top by vacuum vapour deposition.

These processes are generally known to the person skilled in the art and can be applied by him without problems to organic electroluminescent devices comprising compounds of the formula (1) or the preferred embodiments mentioned above.

The compounds according to the invention have the following surprising advantages over the prior art on use in organic electroluminescent devices:

1. The compounds according to the invention have high thermal stability.

2. The compounds according to the invention have high solubility in common organic solvents and very good film-formation properties and are therefore particularly highly suitable for processing from solution.
3. The OLEDs produced using the compounds according to the invention generally have a very long lifetime.
4. The OLEDs produced using the compounds according to the invention generally have very high quantum efficiency.

The invention is described in greater detail by the following examples without wishing it to be restricted thereby. The person skilled in the art will be able, without being inventive, to prepare further compounds according to the invention and to use them in electronic devices and will thus be able to carry out the invention throughout the range claimed.

BRIEF DESCRIPTION OF THE DRAWINGS

FIG. 1 shows the structure of an organic electroluminescent device.

EXAMPLES

The following syntheses are carried out, unless indicated otherwise, under a protective-gas atmosphere in dried solvents. Starting material 8 and solvents are commercially available, for example from ALDRICH. Compounds 1 and 5 can be prepared in accordance with WO 09/124627. Compound 2 can be prepared analogously to *J. Mater. Chem.* 2007, 17, 3714-3719.

Example 1

Preparation of Compound 4

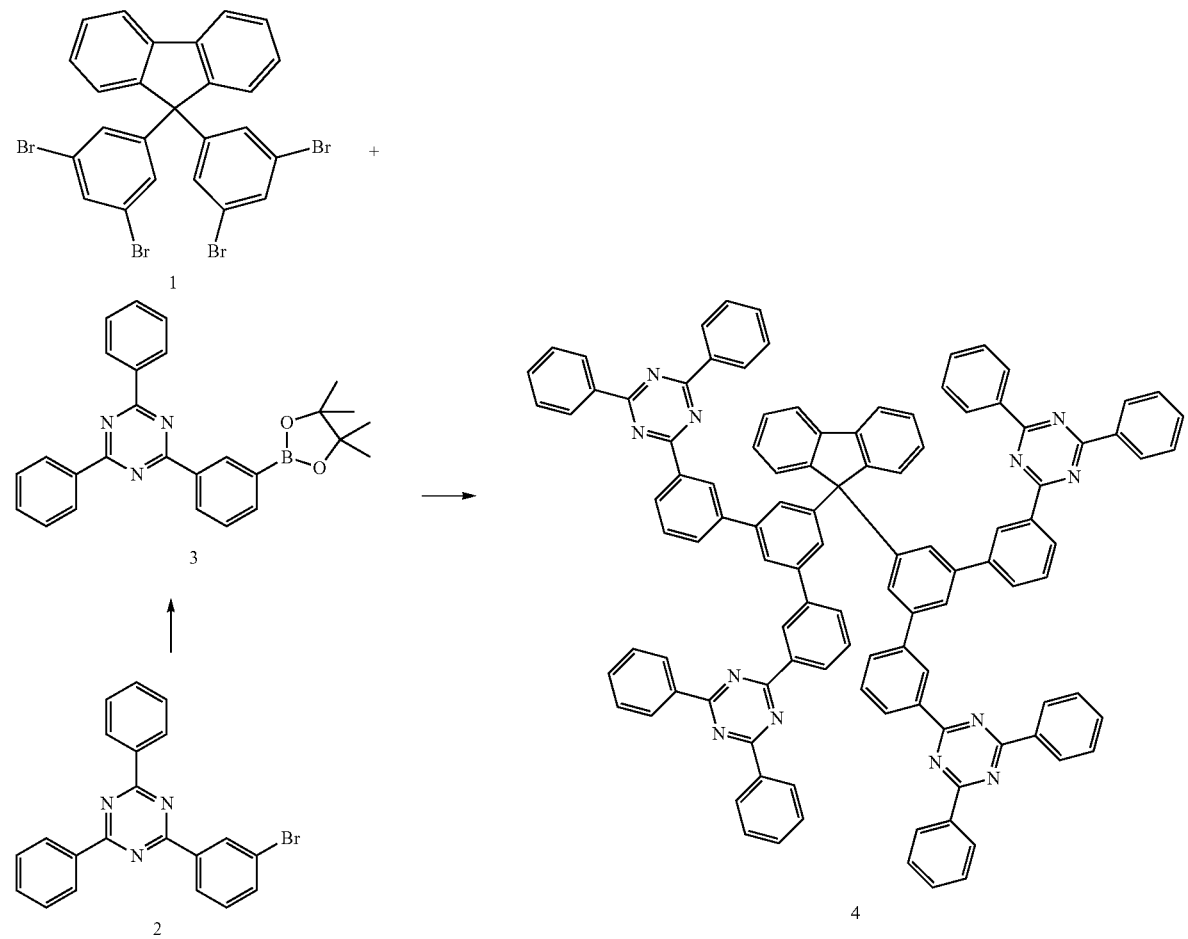

a) Preparation of Compound 3

850 ml of dimethyl sulfoxide, 25.18 g (1.1 molar equivalents, 0.099 mol) of bis(pinacolato)diborane and 25.66 g (2.9 molar equivalents, 0.261 mol) of potassium acetate are added to 35.0 g (1 molar equivalent, 0.090 mol) of compound 2. 2.25 g (3 mmol) of 1,1-bis(diphenylphosphino) ferrocene-palladium(II) chloride (complex with dichloromethane (1:1), Pd 13%) are subsequently added. The batch is heated at 100° C. for 3 h, then cooled to room temperature, and 400 ml of water are added. The mixture is extracted with ethyl acetate, and the combined organic phases are then dried over sodium sulfate and evaporated under reduced pressure. Purification is carried out by recrystallisation (heptane) and gives a beige solid (81.3%).

b) Preparation of Compound 4

10.97 g (1 molar equivalent, 0.017 mol) of compound 1, 33.14 g (4.4 molar equivalents, 0.076 mol) of compound 3 and 29.42 g (8.0 molar equivalents, 0.139 mol) of tripotassium phosphate are suspended in 250 ml of toluene, 125 ml of dioxane and 325 ml of water. 1.270 g (4.2 mmol) of tri-o-tolylphosphine and then 0.156 g (0.7 mmol) of palladium(II) acetate are added to this suspension, and the reaction mixture is heated under reflux for 40 h. After cooling, the organic phase is separated off. The aqueous phase is extracted with dichloromethane, and the combined organic phases are then dried over sodium sulfate, filtered and evaporated under reduced pressure. The residue is recrystallised from dimethylformamide and extracted with hot toluene. The yield is 9.4 g (6.1 mmol), corresponding to 35.1% of theory.

a) Preparation of Compound 6

20 g (32.1 mmol) of compound 5 are suspended in 10 ml of chloroform and 50 ml of glacial acetic acid with 3.4 g (19.2 mmol) of iodic acid and 4.9 g (19.2 mmol) of iodine, and the mixture is heated at 80° C. After a TLC check, the batch is cooled to room temperature and 250 ml of water are added. The mixture is extracted with methylene chloride, and the combined organic phases are then dried using sodium sulfate, filtered and evaporated under reduced pressure. Purification is carried out by washing (ethanol) and recrystallisation (toluene/ethyl acetate) and gives a colourless solid (15.3 g; 64% of theory).

b) Preparation of Compound 7

The synthesis of compound 7 is carried out analogously to that of compound 3. The yield is 7.0 g (9.2 mmol), corresponding to 46% of theory.

c) Preparation of Compound 9

The synthesis of compound 9 is carried out analogously to that of compound 4. The yield is 4.48 g (5.2 mmol), corresponding to 57% of theory.

Example 2

Preparation of compound 9

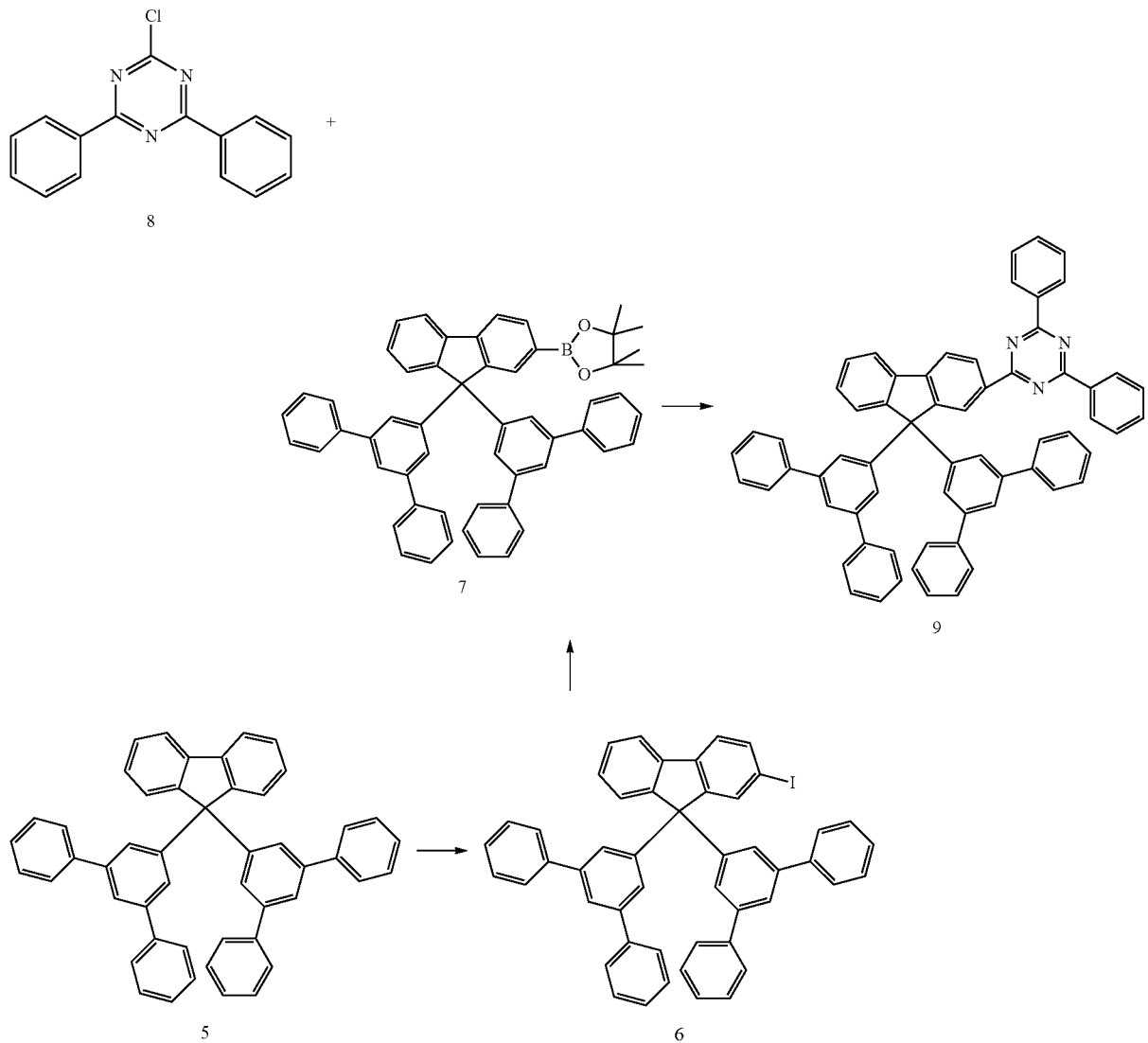

Example 3

Preparation of Compound 11

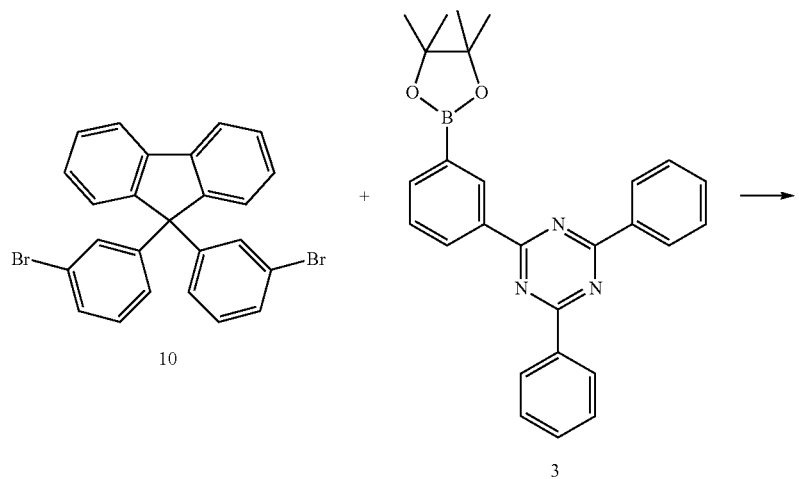

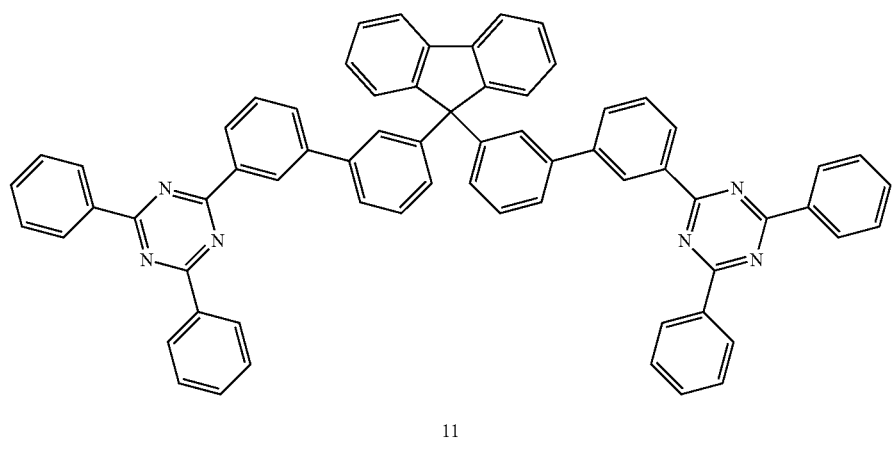

11 a) Preparation of Compound 10

The synthesis of compound 10 is carried out analogously to that of compound 1. 79.8 g (91.9% of theory) of a solid are obtained.

b) Preparation of Compound 11

10.0 g (1 molar equivalent, 21 mmol) of compound 10, 20.1 g (2.2 molar equivalents, 46 mmol) of compound 3 and 53.3 g (11.9 molar equivalents, 251 mmol) of tripotassium phosphate are suspended in 200 ml of toluene, 200 ml of dioxane and 200 ml of water. This mixture is degassed using argon for 15 min, and 458 mg (1.50 mmol) of tri-o-tolylphosphine and then 230 mg (1.03 mmol) of palladium (II) acetate are then added. The reaction mixture is heated under reflux for 16 h, during which a white precipitate deposits. After cooling, 0.60 l of water and 1 l of dichloromethane are added, and the organic phase is separated off. The organic phase is extracted three times with water. The combined organic phases are freed from solvents under reduced pressure. The residue obtained is stirred with 200 ml of hot ethanol, filtered off with suction and washed with further ethanol, leaving a virtually colourless solid. Recrystallisation from dioxane gives 1.90 g (2.04 mmol, 96.5% of theory) of a colourless solid.

Example 4

Preparation of Compound 15

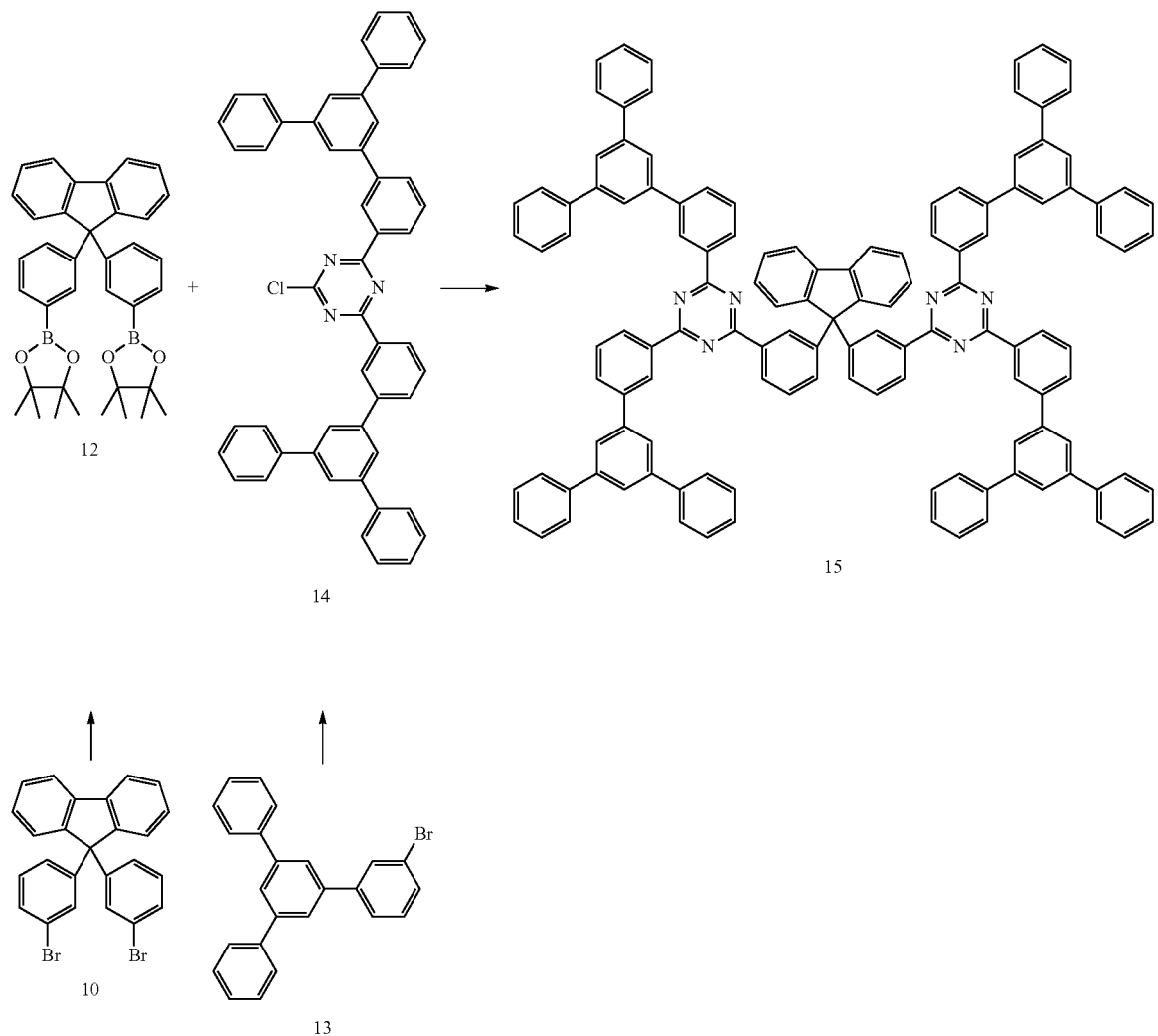

a) Preparation of Compound 12

The synthesis of compound 12 is carried out analogously to that of compound 3. The yield is 590 mg (1.04 mmol), corresponding to 25% of theory.

b) Preparation of Compound 14

The synthesis of compound 14 is carried out analogously to that of compound 8. 6.80 g (9.39 mmol, 27% of theory) of a beige solid are obtained.

c) Preparation of Compound 15

The synthesis of compound 15 is carried out analogously to that of compound 11. The yield is 8.00 g (47.0 mmol), corresponding to 66% of theory.

Example 5

Production and Characterisation of Organic Electroluminescent Devices Comprising the Compounds According to the Invention The structures of TEG (synthesised in accordance with WO 04/026886), TMM-1 (synthesised in accordance with DE 102008036982.9) and TMM-2 (synthesised in accordance with WO 09/124627), and compounds TMM-3 to 6 according to the invention are depicted below for clarity.

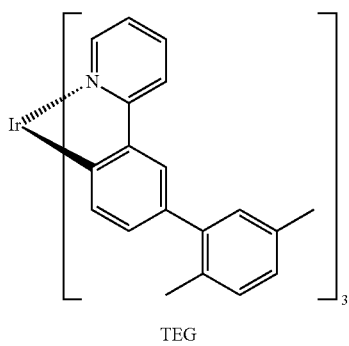

TEG

-continued

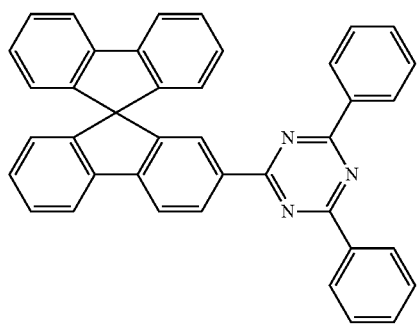

TMM-1

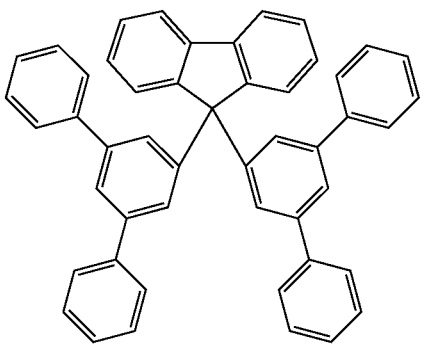

TMM-2

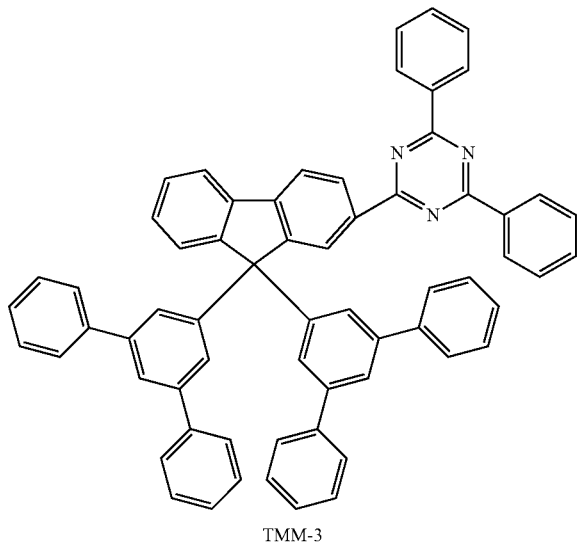

TMM-3

-continued

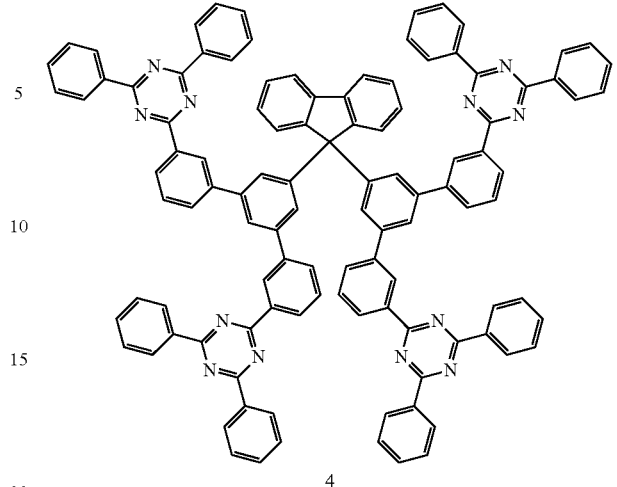

TMM-4

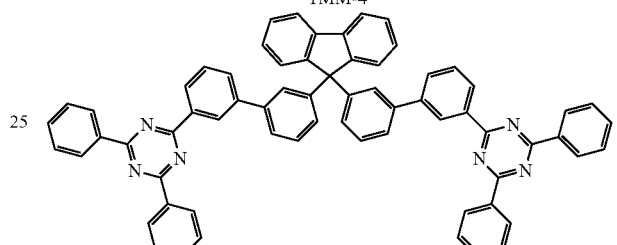

TMM-5

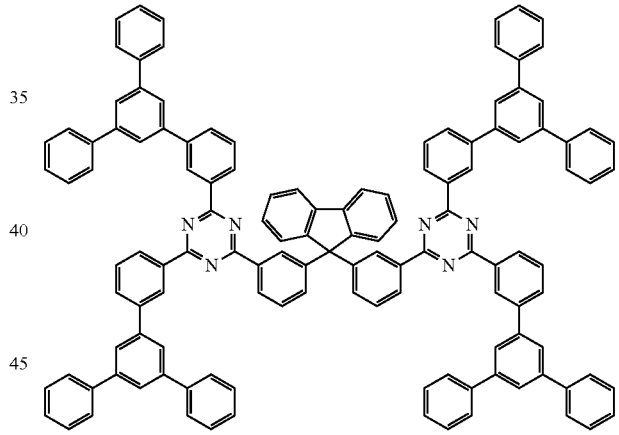

TMM-6

Materials according to the invention can be used from solution, where they result in significantly simpler devices which nevertheless have good properties. The production of such components is based on the production of polymeric light-emitting diodes (PLEDs), which has already been described a number of times in the literature (for example in WO 04/037887). In the present case, the compounds according to the invention or likewise soluble comparative compounds (TMM-1 and TMM-2) are dissolved in toluene or chlorobenzene. The typical solids content of such solutions is between 16 and 25 g/l if, as here, the layer thickness of 80 nm which is typical for a device is to be achieved by means of spin coating. FIG. 1 shows the typical structure of a device of this type. Structured ITO substrates and the material for the so-called buffer layer (PEDOT, actually PEDOT:PSS) are commercially available (ITO from Technoprint and others, PEDOT:PSS as Clevios Baytron P aqueous dispersion from H.C. Starck). The interlayer used serves for hole injection; in this case, HIL-012 from Merck is used. The emission layer is applied by spin coating in an inert-gas atmosphere, in the present case argon, and dried by heating at 120° C. for 10 min. Finally, a cathode comprising barium and aluminium is applied by vacuum vapour deposition. A hole-blocking layer and/or an electron-transport layer can also be applied between the emitting layer and the cathode by vapour deposition, and the interlayer may also be replaced by one or more layers, which merely have to satisfy the condition that they are not detached again by the subsequent processing step of deposition of the emitting layer from solution.

The devices are characterised by standard methods; the OLED examples mentioned have not yet been optimised. Table 1 summarises the data obtained. The two triplet matrix materials are present in the ratio 1:1 (based on the weight of the compounds) in each of Examples 8, 13 and 14. In the case of the processed devices, it is evident here that the materials according to the invention are superior to those previously available in terms of efficiency and/or lifetime.

The structure of the organic electroluminescent device is shown in FIG. 1.

TABLE 1

Results using solution-processed materials in the device configuration of FIG. 1

| Ex. | EML 80 nm | ax. eff. [cd/A] | Voltage [V] at 100 cd/m² | CIE (x, y) | Lifetime [h], initial luminance 1000 cd/m² |
|---|---|---|---|---|---|
| 6 (comp.) | TMM-2:TEG | | 5.7 | 0.34/0.66 | 1200 |
| 7 (comp.) | TMM-1:TEG | 4 | 3.8 | 0.35/0.68 | 9200 |
| 8 (comp.) | TMM-1:TMM-2:TEG | 0 | 3.6 | 0.32/0.63 | 12000 |
| 9 | TMM-3:TEG | 2 | 3.7 | 0.33/0.63 | 15000 |
| 10 | TMM-4:TEG | 3 | 3.5 | 0.33/0.63 | 18000 |
| 11 | TMM-5:TEG | 9 | 3.6 | 0.34/0.62 | 22000 |
| 12 | TMM-6:TEG | 8 | 3.5 | 0.33/0.63 | 20000 |
| 13 | TMM-5:TMM-2:TEG | 3 | 4.5 | 0.34/0.62 | 28000 |
| 14 | TMM-6:TMM-2:TEG | 2 | 4.2 | 0.33/0.62 | 29000 |

The invention claimed is:
1. A compound of formula (1)

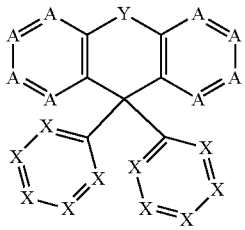

formula (1)

wherein
Y is CO, S, SO, $SO_2$, $PR^3$, or $P(O)R^3$;
X is on each occurrence, identically or differently, $CR^1$ or N, wherein a maximum of three groups X in each ring are N;
A is on each occurrence, identically or differently, $CR^2$ or N, where a maximum of three groups A in each ring are N;

$R^1$ and $R^2$
are on each occurrence, identically or differently, H, D, Cl, Br, I, F, CN, $NO_2$, $Si(R^4)_3$, $B(OR^4)_2$, $C(=O)R^4$, $P(=O)(R^4)_2$, $S(=O)R^4$, $S(=O)_2R^4$, $-CR^4=CR^4-$, $OSO_2R^4$, a straight-chain alkyl, alkoxy or thioalkoxy group having 1 to 40 C atoms or a branched or cyclic alkyl, alkoxy or thioalkoxy group having 3 to 40 C atoms or an alkenyl or alkynyl group having 2 to 40 C atoms, each of which are optionally substituted by one or more radicals $R^4$, where one or more non-adjacent $CH_2$ groups are optionally replaced by $R^4C=CR^4$, $C\equiv C$, $Si(R^4)_2$, $Ge(R^4)_2$, $Sn(R^4)_2$, $C=O$, $C=S$, $C=Se$, $C=NR^4$, $P(=O)(R^4)$, SO, $SO_2$, $NR^4$, O, S or $CONR^4$ and where one or more H atoms are optionally replaced by D, F, Cl, Br, I, CN or $NO_2$, or an aromatic or heteroaromatic ring system having 5 to 60 aromatic ring atoms, which in each case is optionally substituted by one or more radicals $R^4$, or an aryloxy or heteroaryloxy group having 5 to 60 aromatic ring atoms, which is optionally substituted by one or more radicals $R^4$, or aralkyl or heteroaralkyl group having 5 to 60 aromatic ring atoms, which are optionally substituted by one or more radicals $R^4$; wherein two or more adjacent substituents $R^1$ together with the atoms to which they are bonded or two or more adjacent substituents $R^2$ together with the atoms to which they are bonded optionally define a mono- or polycyclic, aliphatic or aromatic ring system with one another; wherein at least one $R^1$ which is bonded to X is triazine, which is optionally substituted by one or more radicals $R^4$, or in that at least one $R^2$ is a 6-membered heteroaromatic group, which is optionally substituted by one or more radicals $R^4$, and at least one radical $R^1$ simultaneously is an aromatic or heteroaromatic ring system having 5 to 60 aromatic ring atoms, which is optionally substituted by one or more radicals $R^4$;

$R^3$ is on each occurrence, identically or differently, an aromatic or heteroaromatic ring system having 5 to 60 ring atoms, which in each case is optionally substituted by one or more radicals $R^4$, or an aryloxy or heteroaryloxy group having 5 to 60 aromatic ring atoms, which is optionally substituted by one or more radicals $R^3$, or a combination of these systems;

$R^4$ is on each occurrence, identically or differently, H, D, F, Cl, Br, I, CN, $NO_2$, $N(R^5)_3$, $Si(R^5)_3$, $B(OR^5)_2$, $C(=O)R^5$, $P(=O)(R^5)_2$, $S(=O)R^5$, $S(=O)_2R^5$, $-CR^5=CR^5-$, $OSO_2R^5$, a straight-chain alkyl, alkoxy or thioalkoxy group having 1 to 40 C atoms or a branched or cyclic alkyl, alkoxy or thioalkoxy group having 3 to 40 C atoms or an alkenyl or alkynyl group having 2 to 40 C atoms, each of which is optionally substituted by one or more radicals $R^5$, where one or more non-adjacent $CH_2$ groups are optionally replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and where one or more H atoms may be replaced by D, F, Cl, Br, I, CN or $NO_2$, or an aromatic or heteroaromatic ring system having 5 to 60 aromatic ring atoms, which in each case are optionally substituted by one or more radicals $R^5$, or an aryloxy or heteroaryloxy group having 5 to 60 aromatic ring atoms, which are optionally substituted by one or more radicals $R^5$, or aralkyl or heteroaralkyl group having 5 to 60 aromatic ring atoms, which are optionally substituted by one or more radicals $R^5$; and wherein two or more radicals R⁴ optionally define a mono- or polycyclic, aliphatic or aromatic ring system with one another together with the atoms to which they are bonded;

R⁵ is on each occurrence, identically or differently, an aliphatic, aromatic and/or heteroaromatic hydrocarbon radical having 1 to 20 C atoms; wherein two or more radicals R⁵ optionally define a mono- or polycyclic, aliphatic or aromatic ring system with one another together with the atoms to which they are bonded.

2. The compound of claim 1, wherein it is a compound of the formula (2), (3), (4), (5), (6), (7), (8), (9), (10), (11), (12), (13), (14) or (15):

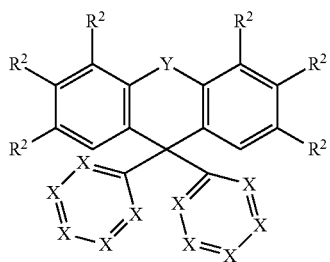

formula (2)

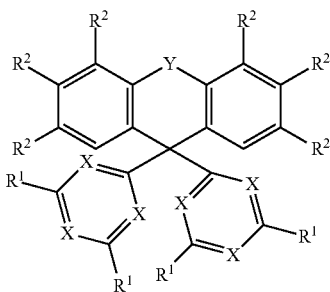

formula (3)

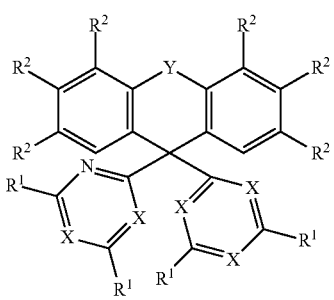

formula (4)

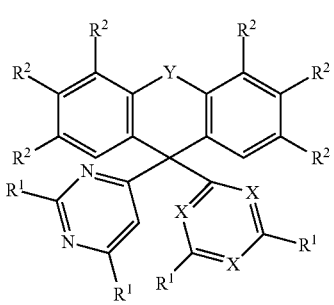

formula (5)

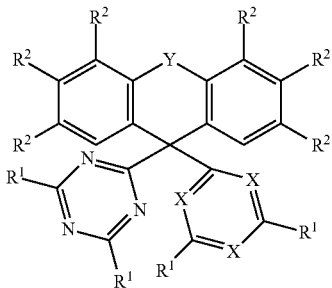

formula (6)

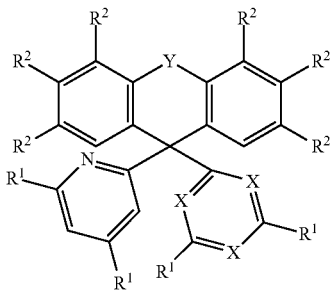

formula (7)

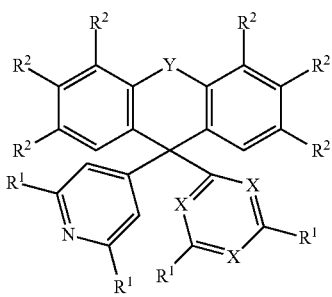

formula (8)

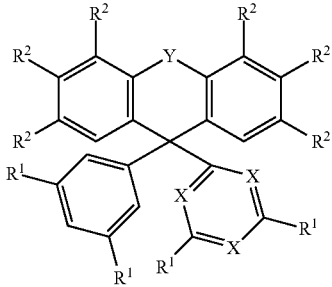

formula (9)

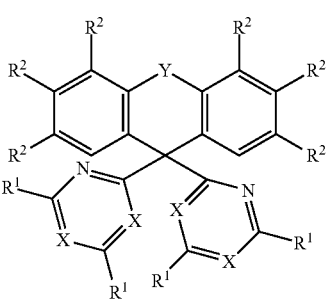

formula (10)

-continued

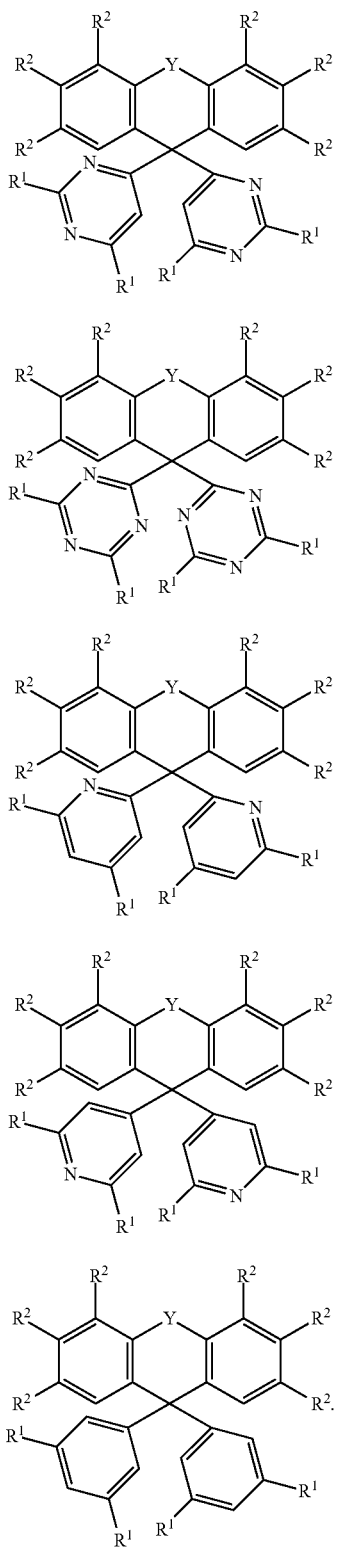

formula (11)

formula (12)

formula (13)

formula (14)

formula (15)

3. The compound of claim 1, wherein, if at least one group $R^1$ is triazine, it is 1,3,5-triazine or 1,2,4-triazine, which in each case is optionally substituted by one or more radicals $R^4$; or in that, if at least one group $R^2$ is a 6-membered heteroaro-matic group, it is selected from the group consisting of triazine, pyrimidine, pyrazine, pyridazine, and pyridine, each of which is optionally substituted by one or more radicals $R^4$.

4. The compound of claim 1, wherein the triazine substituents $R^1$ and $R^2$ and the pyrimidine substituents $R^2$ are selected from the group consisting of:

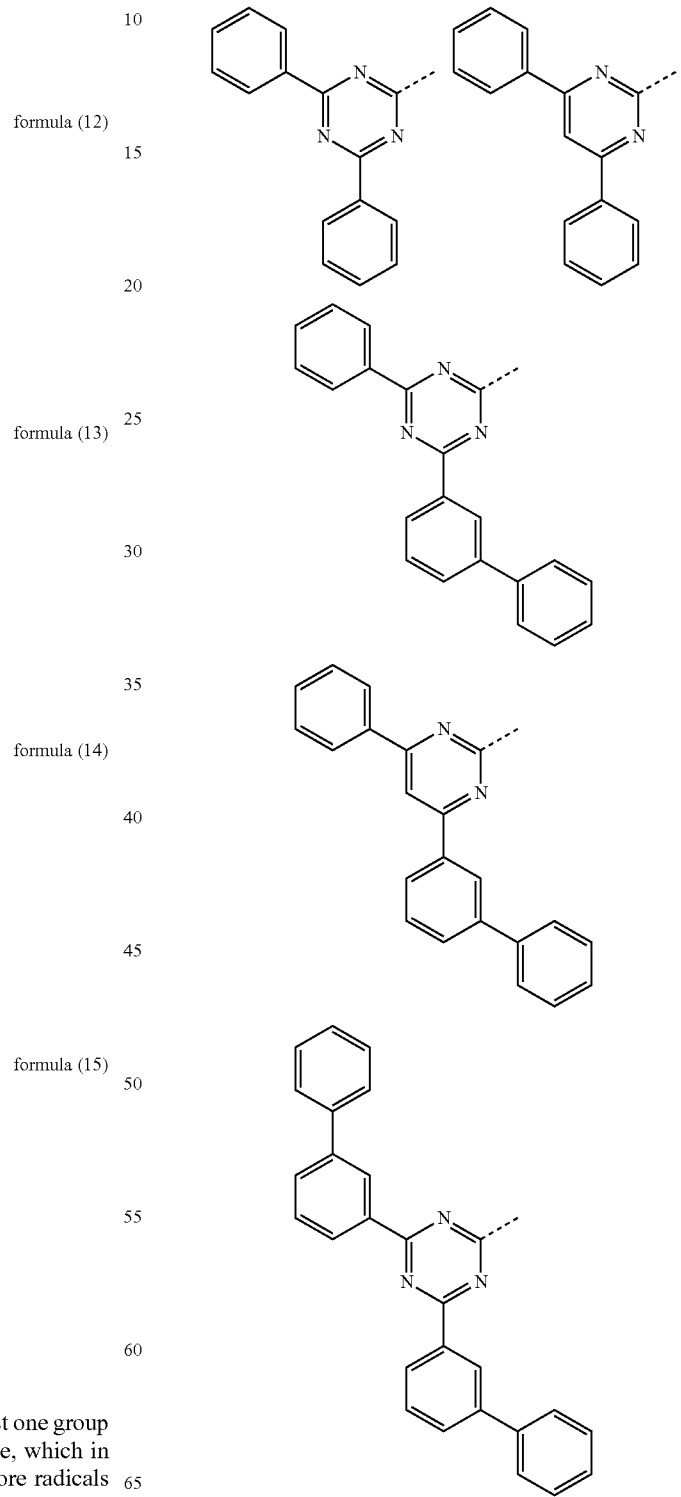

109
-continued
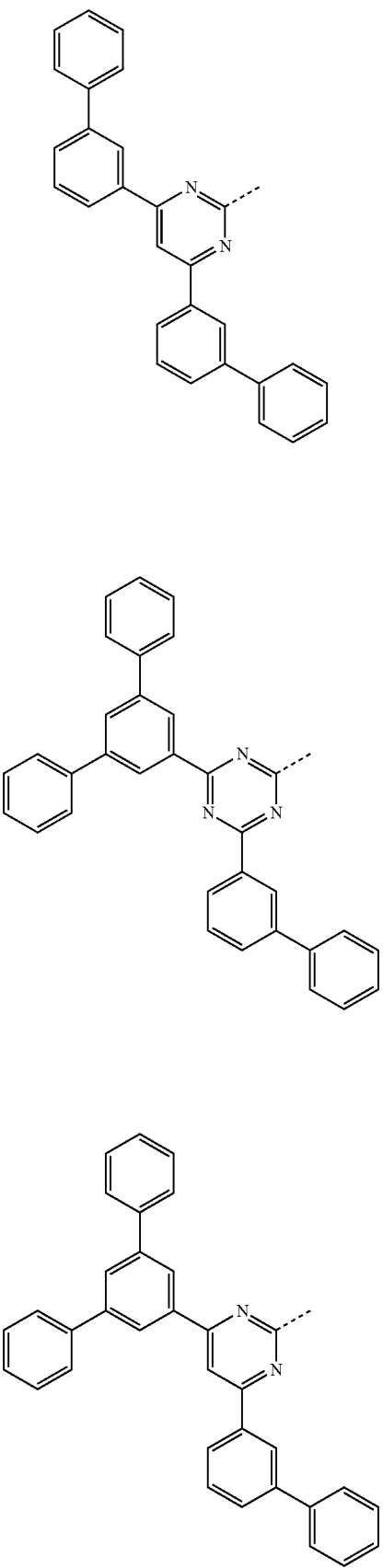
110
-continued
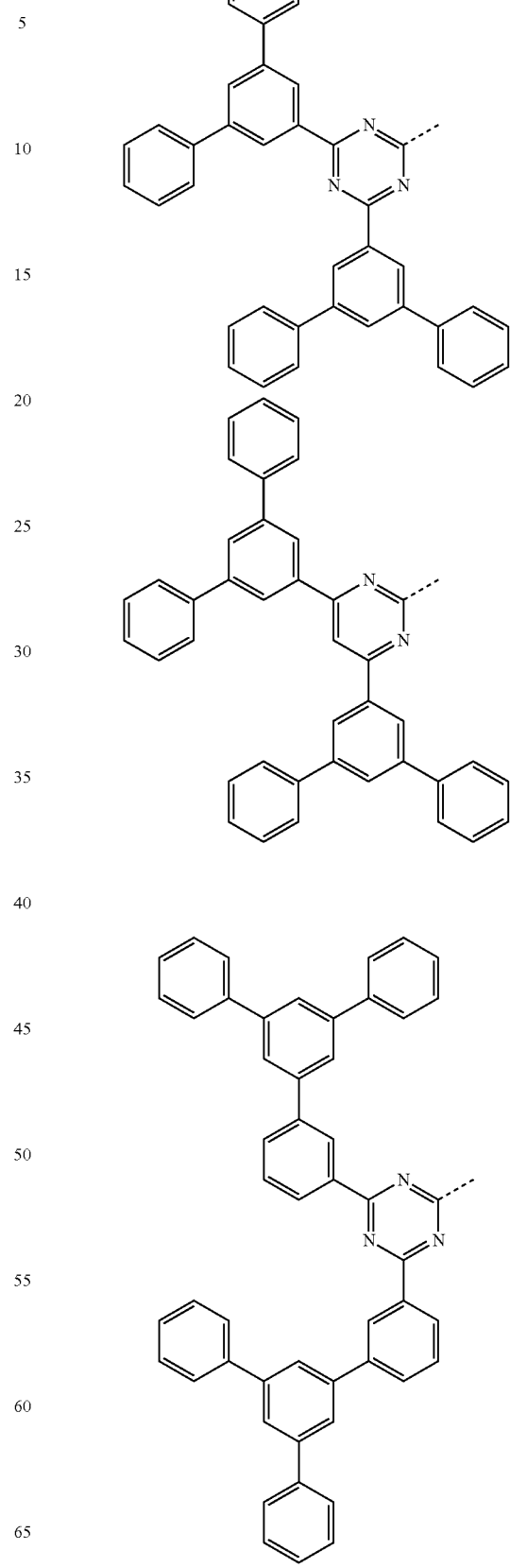

-continued

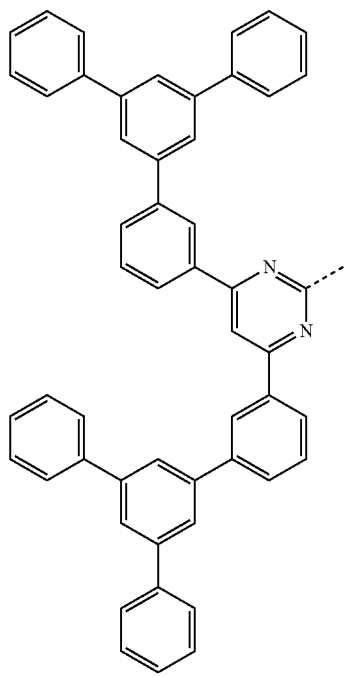

wherein the dashed bond indicates the link from this group to the skeleton.

5. The compound of claim 1, wherein said compound is a compound of formula (16) or (17):

formula (16)

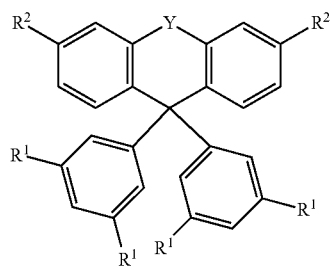

formula (17)

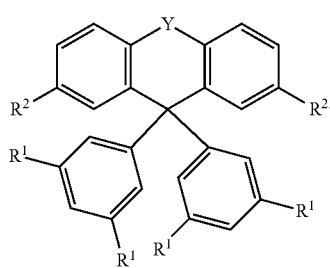

6. The compound of claim 1, wherein said compound is a compound of formulae (22), (23), (26) or (27):

formula (22)

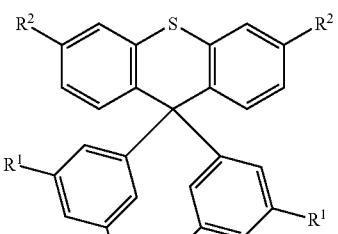

formula (23)

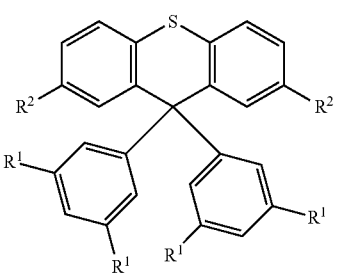

formula (26)

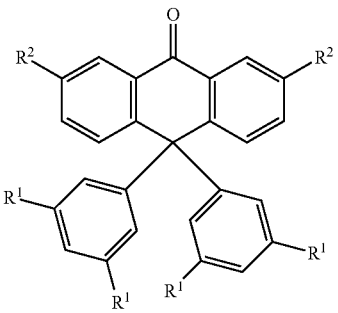

formula (27)

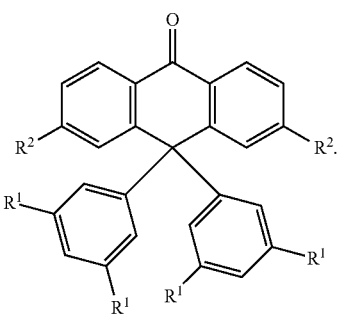

7. The compound of claim 1, wherein said compound is selected from compounds of formulae (30) and (32)

formula (30)

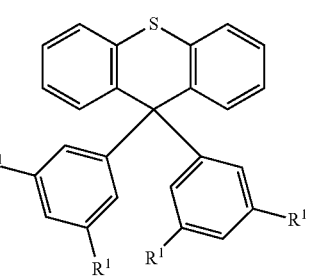

-continued formula (32)

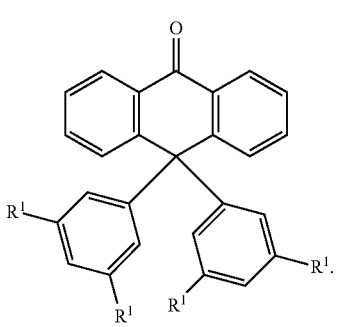

8. A process for preparing the compound of claim 1, comprising (1) reacting bis(3,5-dibromo)benzophenone with a substituted or unsubstituted 2-lithiobi-phenyl, 2-lithiodiphenyl ether, 2-lithiodiphenyl thioether, 2-(2-lithiophenyl)-2-phenyl-1,3-dioxolane, 2-lithiophenyldiphenylamine or a corresponding Grignard compound to give a triarylmethanol, (2) cyclising said triarylmethanol under acidic conditions, and (2) optionally reacting the bromine groups.

9. A dimer, trimer, tetramer, pentamer, oligomer, polymer, or den-drimer comprising one or more compounds of claim 1, wherein one or more radicals R1 or R2 or one or more H atoms of the compound of the formula (1) represent bonds between the compounds of formula (1) in the dimer, trimer, tetramer or pentamer or bonds from the compound of formula (1) to the polymer, oligomer or dendrimer.

10. A mixture comprising at least one compound of claim 1 and at least one further compound.

11. A mixture comprising at least one dimer, trimer, tetramer, pentamer, oligomer or polymer of claim 9 and at least one further compound.

12. A formulation comprising at least one compound of claim 1 and one or more solvents.

13. A formulation comprising at least one dimer, trimer, tetramer, pentamer, oligomer or polymer of claim 9 and one or more solvents.

14. A formulation comprising at least one mixture of claim 10 and one or more solvents.

15. An electronic device comprising at least one compound of claim 1.

16. The electronic device of claim 15, wherein said electronic device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic laser diodes, and organic photoreceptors.

17. The electronic device of claim 16, wherein said electronic device is an organic electroluminescent device, wherein the compound of claim 1 is employed as matrix material for fluorescent or phosphorescent compounds in an emitting layer, and/or in that the compound of claim 1 is employed as electron-transport material or as hole-blocking material in an electron-transport layer or hole-blocking layer.

* * * * *